US012702484B2

(12) United States Patent
Dreyer et al.

(10) Patent No.: US 12,702,484 B2
(45) Date of Patent: Aug. 11, 2026

(54) APPARATUS, SYSTEM, AND METHOD FOR GENERATING PATIENT-SPECIFIC IMPLANTS AND/OR INSTRUMENTATION

(71) Applicant: Treace Medical Concepts, Inc., Ponte Vedra, FL (US)

(72) Inventors: Mark A Dreyer, Bradenton, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 166 days.

(21) Appl. No.: 18/537,593

(22) Filed: Dec. 12, 2023

(65) Prior Publication Data

US 2024/0108414 A1 Apr. 4, 2024

Related U.S. Application Data

(63) Continuation-in-part of application No. 18/129,151, filed on Mar. 31, 2023.

(Continued)

(51) Int. Cl.

*A61B 34/10* (2016.01)
*A61B 17/16* (2006.01)

(Continued)

(52) U.S. Cl.

CPC .......... *A61B 34/10* (2016.02); *A61B 17/1682* (2013.01); *A61B 17/1775* (2016.11); *A61B 2017/568* (2013.01); *A61B 2034/108* (2016.02)

(58) Field of Classification Search

CPC ..... A61B 17/16; A61B 17/1682; A61B 17/17; A61B 17/1775; A61B 17/80;

(Continued)

(56) References Cited

U.S. PATENT DOCUMENTS 3,664,022 A 5/1972 Small
4,069,824 A 1/1978 Weinstock (Continued)

FOREIGN PATENT DOCUMENTS

AU 2009227957 B2 7/2014
AU 2009222469 B2 2/2015

(Continued)

OTHER PUBLICATIONS

Tricot et al., "3D-corrective osteotomy using surgical guides for posttraumatic distal humeral deformity," Acta Orthopaedica Belgica, vol. 78, No. 4, 2012, pp. 538-542.

(Continued)

*Primary Examiner* — Christopher J Beccia
(74) *Attorney, Agent, or Firm* — Fredrikson & Byron, P.A.

(57) ABSTRACT

An apparatus, system, and method are disclosed for remediating a condition present in a patient. In some implementations, the device may include one or more temporary fasteners configured to engage one or more bones of a patient's foot. In addition, the device may include a pivoting resection guide having: a first bone attachment feature configured to receive at least one of one or more temporary fasteners; a second bone attachment feature configured to receive at least one of one or more temporary fasteners; a cutter guide coupled between the first bone attachment feature and the second bone attachment feature, the cutter guide configured to guide a cutting tool as the cutter guide rotates about a pivot axis coupled to the first bone attachment feature and the second bone attachment feature.

20 Claims, 22 Drawing Sheets

Related U.S. Application Data

(60) Provisional application No. 63/387,080, filed on Dec. 12, 2022, provisional application No. 63/326,249, filed on Mar. 31, 2022.

(51) Int. Cl.
*A61B 17/17* (2006.01)
*A61B 17/56* (2006.01)

(58) Field of Classification Search
CPC ... A61B 17/8095; A61B 17/15; A61B 17/151; A61B 34/10
See application file for complete search history.

(56) References Cited

U.S. PATENT DOCUMENTS 4,159,716 A 7/1979 Borchers
4,187,840 A 2/1980 Watanabe
4,335,715 A 6/1982 Kirkley
4,338,927 A 7/1982 Volkov et al.
4,349,018 A 9/1982 Chambers
4,409,973 A 10/1983 Neufeld
4,436,684 A 3/1984 White
4,440,168 A 4/1984 Warren
4,509,511 A 4/1985 Neufeld
4,565,191 A 1/1986 Slocum
4,570,624 A 2/1986 Wu
4,628,919 A 12/1986 Clyburn
4,736,737 A 4/1988 Fargie et al.
4,750,481 A 6/1988 Reese
4,754,746 A 7/1988 Cox
4,757,810 A 7/1988 Reese
4,839,822 A 6/1989 Dormond et al.
4,895,141 A 1/1990 Koeneman et al.
4,959,066 A 9/1990 Dunn et al.
4,978,347 A 12/1990 Ilizarov
4,988,349 A 1/1991 Pennig
4,995,875 A 2/1991 Coes
5,049,149 A 9/1991 Schmidt
5,053,039 A 10/1991 Hofmann et al.
5,112,334 A 5/1992 Alchermes et al.
5,147,364 A 9/1992 Comparetto
5,171,244 A 12/1992 Caspari et al.
5,176,685 A 1/1993 Rayhack
5,207,676 A 5/1993 Canadell et al.
5,254,119 A 10/1993 Schreiber
5,312,412 A 5/1994 Whipple
5,358,504 A 10/1994 Paley et al.
5,364,402 A 11/1994 Mumme et al.
5,374,271 A 12/1994 Hwang
5,417,694 A 5/1995 Marik et al.
5,449,360 A 9/1995 Schreiber
5,470,335 A 11/1995 Du Toit
5,490,854 A 2/1996 Fisher et al.
5,529,075 A 6/1996 Clark
5,540,695 A 7/1996 Levy
5,578,038 A 11/1996 Slocum
5,586,564 A 12/1996 Barrett et al.
5,601,565 A 2/1997 Huebner
5,613,969 A 3/1997 Jenkins, Jr.
5,620,442 A 4/1997 Bailey et al.
5,643,270 A 7/1997 Combs
5,662,656 A 9/1997 White
5,667,510 A 9/1997 Combs
H1706 H 1/1998 Mason
5,722,978 A 3/1998 Jenkins, Jr.
5,749,875 A 5/1998 Puddu
5,779,709 A 7/1998 Harris, Jr. et al.
5,788,695 A 8/1998 Richardson
5,803,924 A 9/1998 Oni et al.
5,810,822 A 9/1998 Mortier
5,836,950 A 11/1998 Hansson
5,839,438 A 11/1998 Graettinger et al.
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Viegas et al.
5,951,556 A 9/1999 Faccioli et al.
5,957,927 A 9/1999 Magee et al.
5,980,526 A 11/1999 Johnson et al.
5,984,931 A 11/1999 Greenfield
6,007,535 A 12/1999 Rayhack et al.
6,030,391 A 2/2000 Brainard et al.
6,162,223 A 12/2000 Orsak et al.
6,171,309 B1 1/2001 Huebner
6,203,545 B1 3/2001 Stoffella
6,248,109 B1 6/2001 Stoffella
6,391,031 B1 5/2002 Toomey
6,416,465 B2 7/2002 Brau
6,478,799 B1 11/2002 Williamson
6,511,481 B2 1/2003 Von Hoffmann et al.
6,676,662 B1 1/2004 Bagga et al.
6,712,824 B2 3/2004 Millard et al.
6,719,773 B1 4/2004 Boucher et al.
6,743,233 B1 6/2004 Baldwin et al.
6,755,838 B2 6/2004 Trnka
6,780,190 B2 8/2004 Maroney
6,796,986 B2 9/2004 Duffner
6,859,661 B2 2/2005 Tuke
6,944,518 B2 9/2005 Roose
6,964,645 B1 11/2005 Smits
7,033,361 B2 4/2006 Collazo
7,097,647 B2 8/2006 Segler
7,153,310 B2 12/2006 Ralph et al.
7,182,766 B1 2/2007 Mogul
7,241,298 B2 7/2007 Nemec et al.
7,282,054 B2 10/2007 Steffensmeier et al.
7,351,203 B2 4/2008 Jelliffe et al.
7,377,924 B2 5/2008 Raistrick et al.
7,465,303 B2 12/2008 Riccione et al.
7,473,255 B2 1/2009 Mcgarity et al.
7,540,874 B2 6/2009 Trumble et al.
7,572,258 B2 8/2009 Stiernborg
7,641,660 B2 1/2010 Lakin et al.
D610,257 S 2/2010 Horton
7,670,345 B2 3/2010 Plassky et al.
7,686,811 B2 3/2010 Byrd et al.
7,691,108 B2 4/2010 Lavallee
7,763,026 B2 7/2010 Egger et al.
7,789,885 B2 9/2010 Metzger
D629,900 S 12/2010 Fisher
7,875,058 B2 1/2011 Holmes, Jr.
7,972,338 B2 7/2011 O'Brien
7,983,777 B2 7/2011 Melton et al.
D646,389 S 10/2011 Claypool et al.
8,057,473 B2 11/2011 Orsak et al.
8,057,478 B2 11/2011 Kuczynski et al.
D651,315 S 12/2011 Bertoni et al.
D651,316 S 12/2011 May et al.
8,080,010 B2 12/2011 Schulz et al.
8,080,045 B2 12/2011 Wotton, III
8,114,087 B2 2/2012 Long et al.
8,123,753 B2 2/2012 Poncet
8,147,530 B2 4/2012 Strnad et al.
8,167,918 B2 5/2012 Strnad et al.
8,172,848 B2 5/2012 Tomko et al.
8,187,280 B2 5/2012 May et al.
8,192,441 B2 6/2012 Collazo
8,197,487 B2 6/2012 Poncet et al.
8,206,153 B2 6/2012 Suttin et al.
8,231,623 B1 7/2012 Jordan
8,231,663 B2 7/2012 Kay et al.
8,246,561 B1 8/2012 Agee et al.
8,246,680 B2 8/2012 Betz et al.
D666,721 S 9/2012 Wright et al.
8,262,664 B2 9/2012 Justin et al.
8,262,665 B2 9/2012 Massoud
8,277,455 B2 10/2012 Couture et al.
8,282,644 B2 10/2012 Edwards
8,282,645 B2 10/2012 Lawrence et al.
8,287,541 B2 10/2012 Nelson et al.
8,292,966 B2 10/2012 Morton
8,303,596 B2 11/2012 Plaky et al.

(56) References Cited

U.S. PATENT DOCUMENTS 8,323,281 B2 12/2012 Hotchkiss et al.
8,323,289 B2 12/2012 Re
8,357,111 B2 1/2013 Caillouette et al.
8,377,105 B2 2/2013 Bscher
8,388,690 B2 3/2013 Singhatat et al.
D679,395 S 4/2013 Wright et al.
8,435,246 B2 5/2013 Fisher et al.
8,475,462 B2 7/2013 Thomas et al.
8,484,001 B2 7/2013 Glozman et al.
8,518,045 B2 8/2013 Szanto
8,523,870 B2 9/2013 Green, II et al.
8,529,568 B2 9/2013 Bouadi
8,532,807 B2 9/2013 Metzger
8,551,106 B2 10/2013 Harrold
D694,884 S 12/2013 Mooradian et al.
D695,402 S 12/2013 Dacosta et al.
8,641,721 B2 2/2014 Aram et al.
8,652,142 B2 2/2014 Geissler
8,657,820 B2 2/2014 Kubiak et al.
D701,303 S 3/2014 Cook
8,663,234 B2 3/2014 Grimm et al.
8,668,700 B2 3/2014 Catanzarite et al.
8,685,030 B2 4/2014 Gtte et al.
8,696,719 B2 4/2014 Lofthouse et al.
8,702,686 B2 4/2014 Geebelen et al.
8,702,712 B2 4/2014 Jordan et al.
8,715,289 B2 5/2014 Smith
8,715,363 B2 5/2014 Ratron et al.
8,728,084 B2 5/2014 Berelsman et al.
8,758,354 B2 6/2014 Habegger et al.
8,777,948 B2 7/2014 Bernsteiner
8,784,457 B2 7/2014 Graham
8,795,286 B2 8/2014 Sand et al.
8,808,298 B2 8/2014 Raub et al.
8,808,301 B1 8/2014 Nofsinger
8,808,302 B2 8/2014 Roose et al.
8,828,012 B2 9/2014 May et al.
8,838,263 B2 9/2014 Sivak et al.
8,858,602 B2 10/2014 Weiner et al.
8,864,773 B2 10/2014 Paul et al.
8,882,778 B2 11/2014 Ranft
8,882,816 B2 11/2014 Kartalian et al.
8,892,235 B2 11/2014 Choi et al.
8,898,043 B2 11/2014 Ashby et al.
D720,456 S 12/2014 Dacosta et al.
8,900,247 B2 12/2014 Tseng et al.
8,911,444 B2 12/2014 Bailey
8,920,428 B2 12/2014 Zakaria et al.
8,926,612 B2 1/2015 Graham
8,932,299 B2 1/2015 Bono et al.
8,939,982 B2 1/2015 Chellaoui
8,939,984 B2 1/2015 Budoff
8,945,132 B2 2/2015 Play et al.
8,965,075 B2 2/2015 Arnaud et al.
8,974,460 B2 3/2015 De La Fuente et al.
8,979,856 B2 3/2015 Catanzarite et al.
8,992,531 B2 3/2015 Chow et al.
8,992,532 B2 3/2015 Wong
8,998,903 B2 4/2015 Price et al.
8,998,904 B2 4/2015 Zeetser et al.
8,998,907 B2 4/2015 Myers
8,998,909 B2 4/2015 Gillman et al.
9,005,207 B2 4/2015 Dodds et al.
9,011,451 B2 4/2015 Long et al.
9,011,452 B2 4/2015 Iannotti et al.
9,011,456 B2 4/2015 Ranawat et al.
9,014,835 B2 4/2015 Azernikov et al.
9,017,329 B2 4/2015 Tyber et al.
9,017,336 B2 4/2015 Park et al.
9,023,052 B2 5/2015 Lietz et al.
9,044,250 B2 6/2015 Olsen et al.
9,060,788 B2 6/2015 Bollinger
9,060,822 B2 6/2015 Wright et al.
9,089,376 B2 7/2015 Medoff et al.
9,101,421 B2 8/2015 Blacklidge
9,107,715 B2 8/2015 Blitz et al.
9,113,915 B2 8/2015 Thomas et al.
9,113,957 B2 8/2015 Axelson, Jr. et al.
9,138,237 B2 9/2015 Meade et al.
9,138,332 B2 9/2015 Harris et al.
D740,424 S 10/2015 Dacosta et al.
9,173,665 B2 11/2015 Couture
9,173,691 B2 11/2015 Orbay et al.
9,186,154 B2 11/2015 Li
9,186,160 B1 11/2015 Song
9,198,678 B2 12/2015 Frey et al.
9,204,897 B2 12/2015 Jones et al.
9,211,128 B2 12/2015 Gillman et al.
9,220,509 B2 12/2015 Boyer et al.
9,220,518 B2 12/2015 Neal et al.
9,220,519 B2 12/2015 Kaneyama et al.
9,220,551 B2 12/2015 Waizenegger
9,232,951 B2 1/2016 Johannaber
9,232,955 B2 1/2016 Bonin, Jr. et al.
9,254,155 B2 2/2016 Iannotti et al.
9,295,497 B2 3/2016 Schoenefeld et al.
9,301,768 B2 4/2016 Buza et al.
9,301,783 B2 4/2016 Gerold et al.
9,308,006 B2 4/2016 Martin et al.
9,308,037 B2 4/2016 Richter et al.
9,320,609 B2 4/2016 Schon et al.
9,345,497 B2 5/2016 Gonzalvez et al.
9,351,738 B2 5/2016 Aram et al.
9,351,743 B2 5/2016 Kehres et al.
9,370,380 B2 6/2016 Riccione
9,375,220 B2 6/2016 Horan et al.
9,402,636 B2 8/2016 Collazo
9,402,640 B2 8/2016 Reynolds et al.
9,408,641 B2 8/2016 Zhang et al.
9,414,846 B2 8/2016 Gillman et al.
9,414,847 B2 8/2016 Kurtz
9,414,877 B2 8/2016 Helenbolt et al.
9,421,021 B2 8/2016 Keppler
9,427,240 B2 8/2016 Von Zabern et al.
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,433,452 B2 9/2016 Weiner et al.
9,445,823 B2 9/2016 Harris et al.
9,452,050 B2 9/2016 Miles et al.
9,456,902 B2 10/2016 Hacking et al.
9,463,034 B2 10/2016 Wong et al.
9,492,182 B2 11/2016 Keefer
9,517,145 B2 12/2016 Meridew et al.
9,522,023 B2 12/2016 Haddad et al.
9,526,514 B2 12/2016 Kelley et al.
9,545,276 B2 1/2017 Buchanan et al.
9,561,041 B2 2/2017 Snider et al.
9,566,103 B2 2/2017 Mayer
9,579,106 B2 2/2017 Lo et al.
9,579,107 B2 2/2017 Schoenefeld
9,579,112 B2 2/2017 Catanzarite et al.
9,592,084 B2 3/2017 Grant
9,603,605 B2 3/2017 Collazo
9,603,640 B2 3/2017 Palmer et al.
9,622,820 B2 4/2017 Baloch et al.
9,629,726 B2 4/2017 Reiley et al.
9,652,889 B2 5/2017 Young et al.
9,662,220 B2 5/2017 Warburton
9,668,746 B2 6/2017 Lee et al.
9,675,471 B2 6/2017 Bojarski et al.
9,687,261 B2 6/2017 Serbousek et al.
9,693,787 B2 7/2017 Ammann et al.
9,693,878 B2 7/2017 Kunz et al.
9,700,433 B2 7/2017 Myers
9,713,484 B2 7/2017 Sammarco
9,737,311 B2 8/2017 Lavallee et al.
9,737,367 B2 8/2017 Steines et al.
9,750,538 B2 9/2017 Soffiatti et al.
9,785,747 B2 10/2017 Geebelen
9,788,958 B2 10/2017 Melamed et al.
9,788,975 B2 10/2017 Li

(56) References Cited

U.S. PATENT DOCUMENTS 9,795,392 B2 10/2017 Zajac
9,795,394 B2 10/2017 Bonutti
9,814,474 B2 11/2017 Montoya et al.
9,820,868 B2 11/2017 Witt et al.
9,826,981 B2 11/2017 Schoenefeld et al.
9,839,438 B2 12/2017 Eash
9,848,929 B2 12/2017 Dacosta et al.
9,849,019 B2 12/2017 Miller et al.
9,877,754 B2 1/2018 Patel et al.
9,883,954 B1 2/2018 Murphy
9,888,931 B2 2/2018 Bake
9,888,950 B2 2/2018 Perez et al.
9,918,658 B2 3/2018 Mccaulley et al.
9,918,769 B2 3/2018 Provencher et al.
9,925,049 B2 3/2018 Goldstein et al.
9,925,068 B2 3/2018 Bays et al.
9,956,089 B2 5/2018 Kelman et al.
9,968,456 B2 5/2018 Song
9,980,760 B2 5/2018 Dacosta et al.
9,987,092 B2 6/2018 Hladio et al.
9,990,765 B2 6/2018 Ju et al.
9,993,256 B2 6/2018 Lipman et al.
10,002,227 B2 6/2018 Netravali et al.
10,004,516 B2 6/2018 Johannaber
10,010,431 B2 7/2018 Eraly et al.
10,016,177 B2 7/2018 Aram et al.
10,022,170 B2 7/2018 Leemrijse et al.
10,028,756 B2 7/2018 Liu
10,034,753 B2 7/2018 Dressler et al.
10,052,114 B2 8/2018 Keppler et al.
10,055,536 B2 8/2018 Maes et al.
10,058,335 B2 8/2018 Lee et al.
10,089,413 B2 10/2018 Wirx-Speetjens et al.
10,098,761 B2 10/2018 Sherman et al.
10,105,145 B2 10/2018 Lavallee
10,123,807 B2 11/2018 Geebelen
10,130,378 B2 11/2018 Bryan
10,149,722 B2 12/2018 Aram et al.
10,159,480 B2 12/2018 Tuten
10,159,499 B2 12/2018 Dacosta et al.
10,159,512 B2 12/2018 Robinson
10,201,357 B2 2/2019 Aram et al.
10,206,692 B2 2/2019 Sanders
10,217,530 B2 2/2019 Couture et al.
10,219,812 B2 3/2019 Torrie et al.
10,226,292 B2 3/2019 Lundquist et al.
10,231,745 B2 3/2019 Geebelen et al.
10,238,382 B2 3/2019 Terrill et al.
10,251,654 B2 4/2019 Fritzinger
10,251,690 B2 4/2019 Katrana et al.
10,262,084 B2 4/2019 Lavallee et al.
10,265,080 B2 4/2019 Hughes et al.
10,271,886 B2 4/2019 Abiven
10,278,713 B2 5/2019 Richter et al.
10,282,488 B2 5/2019 Eash
10,286,197 B2 5/2019 Pouliot et al.
10,325,065 B2 6/2019 Li et al.
10,327,829 B2 6/2019 Dacosta et al.
10,342,529 B2 7/2019 Fallin et al.
10,350,022 B2 7/2019 Jansen et al.
10,357,261 B2 7/2019 Kugler et al.
10,357,299 B2 7/2019 Weiner et al.
10,363,052 B2 7/2019 Park et al.
10,398,510 B2 9/2019 Goto
10,420,613 B2 9/2019 Azevedo Da Silva et al.
10,456,205 B2 10/2019 Meridew et al.
10,512,470 B1 12/2019 Bays et al.
10,524,808 B1 1/2020 Hissong et al.
10,524,845 B2 1/2020 Orsak et al.
10,537,392 B2 1/2020 Millahn et al.
10,543,100 B2 1/2020 Couture et al.
10,548,667 B2 2/2020 Flett et al.
10,548,668 B2 2/2020 Furrer et al.
10,582,969 B2 3/2020 Couture et al.
10,610,241 B2 4/2020 Wagner et al.
10,631,878 B2 4/2020 Fritzinger
10,631,902 B2 4/2020 Weiner et al.
10,653,432 B2 5/2020 Luttrell et al.
10,653,464 B2 5/2020 Hill et al.
10,653,467 B2 5/2020 Brumfield et al.
10,675,096 B2 6/2020 Utz et al.
10,682,147 B2 6/2020 Grant et al.
10,709,567 B2 7/2020 Welker et al.
10,716,581 B2 7/2020 Fritzinger et al.
10,722,309 B2 7/2020 Gillman
10,722,310 B2 7/2020 Luby
10,779,867 B2 9/2020 Penzimer et al.
10,779,890 B2 9/2020 Weir
10,786,291 B2 9/2020 Weiner et al.
10,792,081 B2 10/2020 Weiner et al.
10,806,469 B2 10/2020 Fiechter et al.
10,849,665 B2 12/2020 Singh et al.
10,849,670 B2 12/2020 Santrock et al.
10,856,891 B2 12/2020 Rhodes et al.
10,856,925 B1 12/2020 Pontell
10,869,722 B2 12/2020 Caldwell et al.
10,874,408 B2 12/2020 Couture
10,881,416 B2 1/2021 Couture et al.
10,881,417 B2 1/2021 Mahfouz
10,888,340 B2 1/2021 Awtrey et al.
10,905,444 B2 2/2021 Siccardi et al.
10,912,574 B2 2/2021 Kim et al.
10,925,622 B2 2/2021 Kehres et al.
10,939,926 B2 3/2021 Kam et al.
10,939,939 B1 3/2021 Gil et al.
10,973,529 B2 4/2021 Lavallee et al.
11,000,327 B2 5/2021 Schlotterback et al.
11,020,128 B2 6/2021 Guilloux et al.
11,033,336 B2 6/2021 Bohl
11,065,011 B2 7/2021 Bake et al.
11,074,688 B2 7/2021 Chabin et al.
11,090,069 B2 8/2021 Park
11,090,161 B2 8/2021 Hodorek
11,112,770 B2 9/2021 Roh et al.
11,116,518 B2 9/2021 Hafez
11,129,625 B2 9/2021 Song et al.
11,129,678 B2 9/2021 Park
11,154,362 B2 10/2021 Kim et al.
11,158,047 B2 10/2021 Shah
11,160,567 B2 11/2021 Fallin et al.
11,160,568 B1 11/2021 Park
11,166,732 B2 11/2021 Maxson et al.
11,172,945 B1 11/2021 Lian
11,179,165 B2 11/2021 Schoenefeld
11,179,168 B2 11/2021 Dacosta et al.
11,207,134 B2 12/2021 Hafez
11,213,305 B2 1/2022 Iannotti et al.
11,213,406 B2 1/2022 Rodriguez et al.
11,219,526 B2 1/2022 Mahfouz
11,224,448 B2 1/2022 Bailey
11,259,817 B2 3/2022 Fallin et al.
11,284,909 B2 3/2022 Castricini et al.
11,304,705 B2 4/2022 Fallin et al.
11,304,735 B2 4/2022 Sayger et al.
11,324,522 B2 5/2022 Metzger et al.
11,324,607 B2 5/2022 Mauldin et al.
11,331,148 B2 5/2022 Fritzinger
11,331,205 B2 5/2022 Parr
11,344,347 B2 5/2022 Treace et al.
11,389,221 B2 7/2022 Tyber et al.
11,399,849 B2 8/2022 Larche et al.
11,419,726 B2 8/2022 Miller et al.
11,426,184 B2 8/2022 Rivet-Sabourin et al.
11,432,931 B2 9/2022 Lang
11,436,801 B2 9/2022 Haslam et al.
11,439,412 B2 9/2022 Woodard et al.
11,457,980 B2 10/2022 Bonny et al.
11,484,354 B2 11/2022 Singh et al.
11,497,557 B2 11/2022 Haslam et al.
11,508,102 B2 11/2022 Su et al.
11,510,738 B2 11/2022 Stifter et al.
11,532,402 B2 12/2022 Farley et al.
11,557,036 B2 1/2023 Mansi et al.
11,583,298 B2 2/2023 Robichaud et al.

(56) References Cited

U.S. PATENT DOCUMENTS 11,596,421 B2 3/2023 Saltzman et al.
11,596,443 B2 3/2023 Treace et al.
11,602,386 B2 3/2023 Smith et al.
11,607,250 B2 3/2023 Treace et al.
11,627,954 B2 4/2023 May et al.
11,628,003 B2 4/2023 Nachtrab et al.
11,633,195 B2 4/2023 Dhillon
11,648,019 B2 5/2023 Bays et al.
11,653,938 B2 5/2023 Siegler
11,684,423 B2 6/2023 Jaramaz et al.
11,690,725 B2 7/2023 Gemon et al.
11,717,359 B2 8/2023 Chi
11,741,277 B2 8/2023 Dayal et al.
11,751,892 B2 9/2023 Woodard et al.
11,756,051 B2 9/2023 Indani et al.
11,766,268 B2 9/2023 Iannotti et al.
11,779,467 B2 10/2023 Mimnaugh et al.
11,786,257 B2 10/2023 Dayton et al.
11,793,549 B2 10/2023 Rhodes et al.
11,812,978 B2 11/2023 Trabish et al.
11,819,223 B2 11/2023 Lee
11,819,224 B2 11/2023 Allard et al.
11,849,933 B2 12/2023 Denham et al.
11,849,957 B2 12/2023 Couture et al.
11,849,961 B2 12/2023 Khatibi et al.
11,849,962 B2 12/2023 Singh et al.
11,854,683 B2 12/2023 Casey et al.
D1,011,524 S 1/2024 Santrock et al.
11,857,206 B2 1/2024 Robichaud et al.
11,864,778 B2 1/2024 Mcginley et al.
11,864,959 B2 1/2024 Basta
11,911,046 B2 2/2024 Carroll et al.
11,925,417 B2 3/2024 Mosnier et al.
11,931,106 B2 3/2024 Perler et al.
11,944,546 B2 4/2024 Puncreobutr et al.
11,950,786 B2 4/2024 Courtis et al.
11,963,687 B2 4/2024 Langhorn et al.
11,963,703 B2 4/2024 Dayton et al.
11,963,729 B2 4/2024 Aljuri et al.
11,980,377 B2 5/2024 Mauldin et al.
12,004,789 B2 6/2024 Mcaleer et al.
12,004,814 B2 6/2024 Ryan et al.
D1,034,985 S 7/2024 Hartson et al.
12,035,929 B2 7/2024 Athwal et al.
12,045,943 B2 7/2024 Chaoui et al.
12,048,600 B2 7/2024 Azernikov et al.
12,050,999 B2 7/2024 Poltaretskyi et al.
12,053,242 B2 8/2024 Landon et al.
12,062,183 B2 8/2024 Chaoui et al.
12,097,129 B2 9/2024 Deransart et al.
12,115,083 B2 10/2024 Mullen et al.
12,121,272 B2 10/2024 Marien et al.
2002/0107519 A1 8/2002 Dixon et al.
2003/0236522 A1 12/2003 Long et al.
2004/0010259 A1 1/2004 Keller et al.
2004/0039394 A1 2/2004 Conti et al.
2004/0039396 A1 2/2004 Couture et al.
2004/0097946 A1 5/2004 Dietzel et al.
2004/0138669 A1 7/2004 Horn
2005/0059978 A1 3/2005 Sherry et al.
2005/0080424 A1 4/2005 Cuckler et al.
2005/0267482 A1 12/2005 Hyde
2005/0273112 A1 12/2005 Mcnamara
2006/0129163 A1 6/2006 Mcguire
2006/0206044 A1 9/2006 Simon
2006/0229621 A1 10/2006 Cadmus
2006/0241607 A1 10/2006 Myerson et al.
2006/0241608 A1 10/2006 Myerson et al.
2006/0264961 A1 11/2006 Murray-Brown
2007/0010818 A1 1/2007 Stone et al.
2007/0123857 A1 5/2007 Deffenbaugh et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0039850 A1 2/2008 Rowley et al.
2008/0091197 A1 4/2008 Coughlin
2008/0140081 A1 6/2008 Heavener et al.
2008/0161815 A1 7/2008 Schoenefeld et al.
2008/0172054 A1 7/2008 Claypool et al.
2008/0288004 A1 11/2008 Schendel
2009/0036931 A1 2/2009 Pech et al.
2009/0089081 A1 4/2009 Haddad
2009/0093849 A1 4/2009 Grabowski
2009/0105767 A1 4/2009 Reiley
2009/0198244 A1 8/2009 Leibel
2009/0216089 A1 8/2009 Davidson
2009/0222047 A1 9/2009 Graham
2009/0254092 A1 10/2009 Albiol Llorach
2009/0254126 A1 10/2009 Orbay et al.
2009/0265012 A1 10/2009 Engh et al.
2009/0287309 A1 11/2009 Walch et al.
2010/0069910 A1 3/2010 Hasselman
2010/0130981 A1 5/2010 Richards
2010/0168799 A1 7/2010 Schumer
2010/0185202 A1 7/2010 Lester et al.
2010/0217270 A1 8/2010 Polinski et al.
2010/0256687 A1 10/2010 Neufeld et al.
2010/0274253 A1 10/2010 Ure
2010/0318088 A1 12/2010 Warne et al.
2011/0009865 A1 1/2011 Orfaly
2012/0065689 A1 3/2012 Prasad et al.
2012/0116203 A1 5/2012 Vancraen et al.
2012/0123420 A1 5/2012 Honiball
2012/0130383 A1* 5/2012 Budoff ................ A61B 17/152 606/87
2012/0130434 A1 5/2012 Stemniski
2012/0150242 A1 6/2012 Mannion
2012/0191199 A1 7/2012 Raemisch
2012/0234329 A1 9/2012 Vancraen et al.
2012/0253350 A1 10/2012 Anthony et al.
2012/0265301 A1 10/2012 Demers et al.
2012/0277745 A1 11/2012 Lizee
2013/0211410 A1 8/2013 Landes et al.
2013/0236874 A1 9/2013 Iannotti et al.
2013/0237989 A1 9/2013 Bonutti
2013/0274778 A1 10/2013 Mercier et al.
2013/0289570 A1 10/2013 Chao
2013/0292870 A1 11/2013 Roger
2014/0005672 A1 1/2014 Edwards et al.
2014/0039501 A1 2/2014 Schickendantz et al.
2014/0074099 A1 3/2014 Vigneron et al.
2014/0094861 A1 4/2014 Fallin
2014/0163568 A1 6/2014 Wong et al.
2014/0257402 A1 9/2014 Barsoum
2014/0259629 A1 9/2014 Dion et al.
2014/0263674 A1 9/2014 Cerveny
2014/0343555 A1 11/2014 Russi et al.
2014/0371866 A1 12/2014 Chao et al.
2014/0371897 A1 12/2014 Lin et al.
2015/0032215 A1 1/2015 Slamin et al.
2015/0045903 A1 2/2015 Neal
2015/0066094 A1 3/2015 Anderson et al.
2015/0081029 A1 3/2015 Bojarski et al.
2015/0088142 A1 3/2015 Gibson
2015/0093283 A1 4/2015 Miller et al.
2015/0112348 A1 4/2015 Schoenefeld et al.
2015/0142000 A1 5/2015 Seedhom et al.
2015/0182342 A1 7/2015 Hafez
2015/0227679 A1 8/2015 Kamer et al.
2015/0230843 A1 8/2015 Palmer et al.
2015/0305752 A1 10/2015 Eash
2015/0342616 A1 12/2015 Fryman
2015/0351780 A1 12/2015 Anderson et al.
2015/0351916 A1 12/2015 Kosarek et al.
2016/0015426 A1 1/2016 Dayton
2016/0038161 A1 2/2016 Gibson
2016/0100773 A1 4/2016 Ching et al.
2016/0100847 A1 4/2016 Maxson
2016/0151165 A1 6/2016 Fallin et al.
2016/0175089 A1 6/2016 Fallin et al.
2016/0192951 A1 7/2016 Gelaude et al.
2016/0199198 A1 7/2016 Dietz et al.
2016/0256176 A9 9/2016 Lowery et al.

(56) References Cited

U.S. PATENT DOCUMENTS

2016/0270829 A1 9/2016 Duggal et al.
2016/0270855 A1 9/2016 Kunz et al.
2016/0287395 A1 10/2016 Khalili et al.
2016/0338715 A1 11/2016 Bojarski et al.
2016/0354128 A1 12/2016 Jeng et al.
2016/0367270 A1 12/2016 Garlock et al.
2017/0014169 A1 1/2017 Dean et al.
2017/0020537 A1 1/2017 Tuten
2017/0027593 A1 2/2017 Bojarski et al.
2017/0079803 A1 3/2017 Lang
2017/0143511 A1 5/2017 Cachia
2017/0209189 A9 7/2017 Hatch et al.
2017/0231645 A1 8/2017 Metzger et al.
2017/0245906 A1 8/2017 Kugler et al.
2017/0245935 A1 8/2017 Kugler et al.
2017/0249440 A1 8/2017 Lang et al.
2017/0281353 A1 10/2017 Al Hares et al.
2017/0360578 A1 12/2017 Shin et al.
2018/0021145 A1 1/2018 Seavey et al.
2018/0028325 A1 2/2018 Bojarski et al.
2018/0049758 A1 2/2018 Amis et al.
2018/0116804 A1 5/2018 Hafez et al.
2018/0221071 A1 8/2018 Isch
2018/0235706 A1 8/2018 Asseln et al.
2018/0242987 A1 8/2018 Lintula et al.
2018/0289423 A1 10/2018 Singh et al.
2018/0317986 A1 11/2018 Jackman et al.
2018/0344326 A1 12/2018 Chan et al.
2019/0000629 A1 1/2019 Winslow
2019/0008532 A1 1/2019 Fitz et al.
2019/0117239 A1 4/2019 Verma
2019/0175277 A1 6/2019 Chav et al.
2019/0175351 A1 6/2019 Bojarski et al.
2019/0307495 A1 10/2019 Geldwert
2019/0365543 A1 12/2019 Slamin et al.
2020/0008813 A1 1/2020 Bonny et al.
2020/0046425 A1 2/2020 Lopes et al.
2020/0100909 A1 4/2020 Lang et al.
2020/0155323 A1 5/2020 Lang et al.
2020/0163721 A1 5/2020 Aghazadeh
2020/0214719 A1 7/2020 Fraone et al.
2020/0337714 A1 10/2020 Hafez et al.
2020/0356073 A1 11/2020 Tokushima
2020/0405322 A1 12/2020 Brailovski et al.
2021/0007760 A1 1/2021 Reisin
2021/0022781 A1 1/2021 Dacosta et al.
2021/0030429 A1 2/2021 Rose et al.
2021/0045756 A1 2/2021 Zakhary et al.
2021/0059691 A1 3/2021 Zille
2021/0059837 A1 3/2021 Rhodes
2021/0077120 A1 3/2021 Hatch et al.
2021/0077192 A1* 3/2021 Perler .................... G16H 30/40
2021/0085338 A1 3/2021 Dacosta et al.
2021/0090248 A1 3/2021 Choi et al.
2021/0106427 A1 4/2021 Mahfouz
2021/0113223 A1 4/2021 Schaumann et al.
2021/0121297 A1 4/2021 Cavanagh et al.
2021/0137537 A1 5/2021 Zille
2021/0161543 A1 6/2021 Mcauliffe et al.
2021/0186704 A1 6/2021 Fitz et al.
2021/0192759 A1 6/2021 Lang
2021/0196290 A1 7/2021 Iannotti et al.
2021/0212705 A1 7/2021 Reynolds et al.
2021/0219989 A1 7/2021 Chao
2021/0244477 A1 8/2021 Singh et al.
2021/0256171 A1 8/2021 Hosseini
2021/0275196 A1 9/2021 Wodajo
2021/0282790 A1 9/2021 Sellman et al.
2021/0282823 A1 9/2021 Day et al.
2021/0290250 A1 9/2021 Denham et al.
2021/0298766 A1 9/2021 Loring et al.
2021/0307833 A1 10/2021 Farley et al.
2021/0307834 A1 10/2021 Gillman et al.
2021/0346038 A1 11/2021 Fiechter et al.
2021/0378752 A1 12/2021 Paul et al.
2021/0386437 A1 12/2021 Dacosta et al.
2021/0391058 A1 12/2021 Kostrzewski et al.
2021/0393304 A1 12/2021 Geldwert
2022/0039965 A1 2/2022 Casey et al.
2022/0087822 A1 3/2022 Radermacher et al.
2022/0096157 A1 3/2022 Pollock et al.
2022/0133484 A1 5/2022 Lang
2022/0160405 A1 5/2022 Casey et al.
2022/0167998 A1 6/2022 Siccardi et al.
2022/0192685 A1 6/2022 Gazonnet et al.
2022/0202495 A1 6/2022 Pack
2022/0211387 A1 7/2022 Perler et al.
2022/0233203 A1 7/2022 Rhodes et al.
2022/0249106 A1 8/2022 Akallal et al.
2022/0249143 A1 8/2022 Hollis et al.
2022/0270762 A1 8/2022 Crawford et al.
2022/0273450 A1 9/2022 Steines et al.
2022/0296285 A1 9/2022 Le Besque et al.
2022/0313284 A1 10/2022 Korman
2022/0323086 A1 10/2022 Stemniski et al.
2022/0338934 A1 10/2022 Perler et al.
2022/0346806 A1 11/2022 Leemrijse et al.
2023/0013727 A1 1/2023 Korman et al.
2023/0014384 A1 1/2023 Cordonnier et al.
2023/0077222 A1 3/2023 Awtrey
2023/0157705 A1 5/2023 Reynolds
2023/0190306 A1 6/2023 Kowalczyk et al.
2023/0281842 A1 9/2023 Ribeiro et al.
2023/0310013 A1 10/2023 Perler et al.
2023/0310051 A1 10/2023 Hafez et al.
2023/0363773 A1 11/2023 Perler et al.
2023/0371966 A1 11/2023 Spitler
2023/0389937 A1 12/2023 Penner et al.
2023/0404673 A1 12/2023 Spitler et al.
2024/0005504 A1 1/2024 Ribeiro et al.
2024/0008880 A1 1/2024 Spitler et al.
2024/0099778 A1 3/2024 Hlad et al.

FOREIGN PATENT DOCUMENTS

AU 2015203808 B2 9/2017
AU 2020220169 A1 9/2020
AU 2021286392 A1 1/2022
CA 2491824 A1 9/2005
CA 2608464 C 7/2012
CA 2854997 A1 5/2013
CA 2713309 C 7/2013
CH 695846 A5 9/2006
CN 2930668 Y 8/2007
CN 201558162 U 8/2010
CN 201572172 U 9/2010
CN 201586060 U 9/2010
CN 201912210 U 8/2011
CN 101237835 B 11/2012
CN 202801773 U 3/2013
CN 103462675 A 12/2013
CN 103505276 A 1/2014
CN 203458450 U 3/2014
CN 102860860 B 5/2014
CN 203576647 U 5/2014
CN 104490460 A 4/2015
CN 104510523 A 4/2015
CN 104523327 A 4/2015
CN 104546102 A 4/2015
CN 204379413 U 6/2015
CN 204410951 U 6/2015
CN 204428143 U 7/2015
CN 204428144 U 7/2015
CN 204428145 U 7/2015
CN 204446081 U 7/2015
CN 106236185 A 12/2016
CN 205924106 U 2/2017
CN 206151532 U 5/2017
CN 105105853 B 7/2017
CN 108030532 A 5/2018
CN 207721902 U 8/2018
CN 112914724 B 2/2022
CN 117297772 B 2/2024
CN 117322951 B 2/2024

(56) References Cited

FOREIGN PATENT DOCUMENTS

| | | | |
|---|---|---|---|
| CN | 109223098 | B | 5/2024 |
| DE | 2910627 | A1 | 9/1980 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124832 | B1 | 8/2012 |
| EP | 2750617 | A1 | 7/2014 |
| EP | 2856951 | A1 | 4/2015 |
| EP | 2624764 | B1 | 12/2015 |
| EP | 3000443 | A3 | 7/2016 |
| EP | 2083758 | B1 | 11/2017 |
| EP | 2632349 | B1 | 3/2018 |
| EP | 3013256 | B1 | 11/2018 |
| EP | 3171795 | B1 | 11/2018 |
| EP | 3672535 | A1 | 7/2020 |
| EP | 2558010 | B1 | 5/2021 |
| EP | 3948895 | A1 | 2/2022 |
| EP | 3740141 | B1 | 4/2022 |
| EP | 2844162 | B1 | 7/2022 |
| FR | 2362616 | A1 | 3/1978 |
| FR | 2764183 | A1 | 12/1998 |
| FR | 2953120 | B1 | 1/2012 |
| FR | 3030221 | A1 | 6/2016 |
| FR | 3117328 | B1 | 3/2023 |
| GB | 2154143 | A | 9/1985 |
| GB | 2154144 | A | 9/1985 |
| GB | 2334214 | B | 1/2003 |
| GB | 2589960 | A | 6/2021 |
| JP | S635739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| KR | 1020160090006 | A | 7/2016 |
| KR | 1020180118476 | A | 10/2018 |
| KR | 101952368 | B1 | 2/2019 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| RU | 2789960 | C2 | 2/2023 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009001083 | A1 | 12/2008 |
| WO | 2009029798 | A1 | 3/2009 |
| WO | 2009032101 | A2 | 3/2009 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012176077 | A1 | 12/2012 |
| WO | 2013026786 | A1 | 2/2013 |
| WO | 2013041618 | A1 | 3/2013 |
| WO | 2013134387 | A1 | 9/2013 |
| WO | 2013156816 | A2 | 10/2013 |
| WO | 2014020561 | A1 | 2/2014 |
| WO | 2014020562 | A1 | 2/2014 |
| WO | 2014022055 | A1 | 2/2014 |
| WO | 2014085882 | A1 | 6/2014 |
| WO | 2014147099 | A1 | 9/2014 |
| WO | 2014152219 | A2 | 9/2014 |
| WO | 2014200017 | A1 | 12/2014 |
| WO | 2015003284 | A2 | 1/2015 |
| WO | 2015094409 | A1 | 6/2015 |
| WO | 2015127515 | A2 | 9/2015 |
| WO | 2016012731 | A1 | 1/2016 |
| WO | 2016102025 | A1 | 6/2016 |
| WO | 2017031000 | A1 | 2/2017 |
| WO | 2017122076 | A2 | 7/2017 |
| WO | 2017151833 | A1 | 9/2017 |
| WO | 2018167369 | A1 | 9/2018 |
| WO | 2019060780 | A2 | 3/2019 |
| WO | 2019052622 | A4 | 5/2019 |
| WO | 2019180747 | A1 | 9/2019 |
| WO | 2020060349 | A1 | 3/2020 |
| WO | 2021054518 | A1 | 3/2021 |
| WO | 2021091071 | A1 | 5/2021 |
| WO | 2021118733 | A1 | 6/2021 |
| WO | 2021127625 | A1 | 6/2021 |
| WO | 2021240290 | A1 | 12/2021 |
| WO | 2022155208 | A1 | 7/2022 |
| WO | 2022182312 | A1 | 9/2022 |
| WO | 2023096516 | A1 | 6/2023 |
| WO | 2024025840 | A1 | 2/2024 |

OTHER PUBLICATIONS

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D Med, "Anatomical Model: Calcaneus" , 2022, pp. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, "Cuboid Suspension in Charcot Reconstruction. Using 3D Imaging for Planning, Printing and Execution for Complex Deformity Correction" Downloaded Apr. 2021, pp. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

(56) References Cited

OTHER PUBLICATIONS

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Santrock et al., "Hallux Valgus Deformity and Treatment: A Three-Dimensional Approach: Lapiplasty," Foot & Ankle Clinics, vol. 23, No. 2, 2018, pp. 281-295.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus," The Foot and Ankle, Second Edition, Chapter 8, 2002, pp. 99-117.
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Shima et al., "Operative Treatment for Hallux Valgus With Moderate to Severe Metatarsus Adductus," Foot & Ankle International, vol. 40, No. 6, 2019, pp. 641-647.
Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Stryker, "PROstep Minimally Invasive Surgery" https://www.stryker.com/us/en/foot-and-ankle/products/prostep.html, Downloaded Jun. 23, 2023, pp. 10.
Synergy 3D Med, "Anatomical Model: Calcaneus" Downloaded Mar. 2, 2023, pp. 2.
Synopsys, "Medical Image Segmentation with Machine Learning—Simpleware Automated Solution Modules", https://www.synopsys.com/simpleware/software/auto-segmenter-modules.html#simpleware-as-ortho, 2022, pp. 12.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Tornier Technology, "Tornier Blueprint 3D Planning + PSI", https://www.wrightemedia.com/ProductFiles/Files/PDFs/CAW-8609_EN_HR_LE.pdf, Feb. 2017, pp. 12.
Total Ankle Institute, "Prophecy: Preoperative Navigation Guides", https://www.totalankleinstitute.com/infinity-products/prophecy-preoperative-navigation-guides/, 2019, pp. 6.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Treace "FastGrafter Autograft Harvesting System" Downloaded from https://www.lapiplasty.com/surgeons/other-products/fastgrafter/, Dec. 4, 2024, pp. 8.
Treace Medical Concepts, "Adductoplasty Midfoot Correction System", https://www.lapiplasty.com/surgeons/other-products/adductoplasty-system/, Downloaded May 2, 2022, pp. 9.
Use for BME Speed Nitinol Staple Fixation for the Lapidus Procedure, "date unknown, 1 page."
Virzi et al. "Comprehensive Review of 3D Segmentation Software Tools for MRI Usable for Pelvic Surgery Planning", Journal of Digital Imaging (2020) 33, pp. 99-110.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Decarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
Disior, "Bonelogic Foot & Ankle Module", https://www.disior.com/foot--ankle.html, Downloaded Jun. 1, 2022, pp. 6.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

(56) References Cited

OTHER PUBLICATIONS

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Fibretuff, "3D Printing, CNC Machining, Molding and Extruding Biocompatible material's with "bone like" Qualities for 3D Printing" https://fibretuff.us, Downloaded Feb. 24, 2023, pp. 22.
Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.
Hunt et al., "Locked Versus Nonlocked Plate Fixation for Hallux MTP Arthrodesis," Foot and Ankle International, vol. 32, No. 7, Jul. 2011, pp. 704-709.
Integra, "Integra Large Qwix Positioning and Fixation Screw, Surgical Technique," 2012, 16 pages.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
KLS Martin Group, "Individual Patient Solutions IPS Implants", https://www.klsmartin.com/en-na/products/individual-patient-solutions/ips-implants/, Downloaded: Jun. 1, 2022, pp. 8.
Kurup et al., "Midfoot arthritis—current concepts review," Journal of Clinical Orthopaedics and Trauma, vol. 11, 2020, pp. 399-405.

(56) References Cited

OTHER PUBLICATIONS

La Reaux et al., "Metatarsus adductus and hallux abducto valgus: their correlation," The Journal of Foot Surgery, vol. 26, No. 4, Jul. 1987, pp. 304-308, Abstract Only.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "A systematic approach to the surgical correction of combined hallux valgus and metatarsus adductus deformities," The Journal of Foot & Ankle Surgery, May 21, 2021, 6 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.
McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Michelangelo Bunion System, Surgical Technique ",Instratek Incorporated, publication date unknown, 4 pages."
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and the BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Novastep, "Pecaplasty Percutaneous Bunion Correction" Downloaded Jun. 29, 2022, pp. 24.
Novastep, "Pecaplasty Percutaneous Bunion Correction—Brochure Pecaplasty Targeting Guide" Downloaded Dec. 15, 2021, pp. 4.
Odenbring et al., "A guide instrument for high tibial osteotomy," Acta Orthopaedica Scandinavica, vol. 60, No. 4, 1989, pp. 449-451.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Instratek, "Michelangelo Bunion System, Surgical Technique", Instratek Incorporated, publication date unknown, 4 pages.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Weber et al., "A Simple System for Navigation of Bone Alignment Osteotomies of the Tibia," International Congress Series, vol. 1268, Jan. 2004, pp. 608-613, (Abstract Only).
Wukich et al., "Hypermobility of the First Tarsometatarsal Joint," Foot and Ankle Clinics, vol. 10, No. 1, Mar. 2005, pp. 157-166.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

(56) References Cited

OTHER PUBLICATIONS

Vitek, "Neue Techniken in der Fuchirurgie Das V-tek-System," ABW Wissenschaftsverlag GmbH, 2009, 11 pages, including English Abstract.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation for Nonunions: What the Evidence Reveals," Podiatry Today, vol. 24, No. 9, Sep. 2011, pp. 52-57.
Williams et al., "Metatarsus adductus: Development of a non-surgical treatment pathway," Journal of Paediatrics and Child Health, vol. 49, 2013, pp. E428-433.
Yasuda et al., "Proximal Supination Osteotomy of the First Metatarsal for Hallux Valgus," Foot and Ankle International, vol. 36, No. 6, Jun. 2015, pp. 696-704.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Wright Medical, "How BLUEPRINT Works—from CT to 3D [CAW-9389]", https://www.wrightmeded.com/videos/how-blueprint-works-from-ct-to-3d-caw-9389, video time mark 32 seconds to 48 seconds, Dated May 26, 2022.
International Searching Authority, "International Search Report and Written Opinion", From Application No. PCT/US2023/017029, Mailed Jul. 19, 2023, pp. 9.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Acumed "Acumed Osteotomy System" with partial English Translation, 2014, pp. 19.
Additive Orthopaedics, "The First and Only FDA Approved Patient Specific Talus Spacer" , https://totaltalusreplacement.com, Downloaded: Mar. 4, 2022, pp. 11.
Aiyer et al. "Prevalence of Metatarsus Adductus in Patients Undergoing Hallux Valgus Surgery" Foot & Ankle International 2014, vol. 35(12), pp. 1292-1297.
Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.
Alvine et al. "Peg and Dowel Fusion of the Proximal Interphalangeal Joint" Foot & Ankle vol. 1, No. 2, 1980 American Orthopaedic Foot Society, pp. 5.
Arthrex "Chevron Osteotomy" https://www.arthrex.com/foot-ankle/chevron-osteotomy, Retrieved Nov. 30, 2022, pp. 7.
Arthrex "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.
Arthrex, "Distal Tibia Allograft Workstation for Glenoid Bone Loss, Surgical Technique" Arthrex.com, 2018, pp. 8.
Baravarian, "Why the Lapidus Procedure is Ideal for Bunions" Podiatry Today, https://www.hmpgloballearningnetwork.com/site/podiatry/article/5542, May 2006 pp. 8.
Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.
Bednarz et al. "Modified Lapidus Procedure for the Treatment of Hypermobile Hallux Valgus" Foot & Ankle, American Orthopaedic Foot & Ankle Society, 2000, pp. 6.
Bennett et al. "Intraosseous Sliding Plate Fixation Used in Double Osteotomy Bunionectomy" Foot & Ankle International, 2019, vol. 40(1), pp. 85-88.
Biopro "Accu-Cut Osteotomy Guide System Accurate and consistent hallux valgus correction" Document Dates Sep. 16, 2019, pp. 2.
Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.
Bouaicha et al. "Fixation of Maximal Shift Scarf Osteotomy with Inside-Out Plating: Technique Tip" Foot & Ankle International, vol. 32, No. 5, May 2011, pp. 567-569.
Buda et al. "Effect of Fixation Type and Bone Graft on Tarsometatarsal Fusion" Foot & Ankle International 2018, vol. 39(12), pp. 1394-1402.
Carr et al. "Correctional Osteotomy for Metatarsus Primus Varus and Hallux Valgus*" The Journal of Bone and Joint Surgery, vol. 50-A, No. 7, Oct. 1968, pp. 1353-1367.
Catanese et al. "Measuring Sesamoid Position in Hallux Valgus When Is the Sesamoid Axial View Necessary?" Foot & Ankle Specialist, Downloaded Aug. 15, 2016, pp. 1-3.
Chesser et al. "New Advances With the Tarsometatarsal" Podiatry Today, vol. 30, Issue 10, Oct. 2017, pp. 28-36.
Chomej et al. "Lateralising DMMO (MIS) for simultaneous correction of a pes adductus during surgical treatment of a hallux valgus" Journal Pre-proof, The Foot, Accepted Jul. 16, 2020, pp. 33.
Cichero et al. "Different fixation constructs and the risk of non-union following first metatarsophalangeal joint arthrodesis" Foot and Ankle Surgery, 27, 2021, Accepted Oct. 15, 2020, pp. 789-792.
Coetzee et al., "Revision Hallux Valgus Correction," Operative Techniques in Foot and Ankle Surgery, Section I, Chapter 15, 2011, pp. 84-96.
Collan et al., "The biomechanics of the first metatarsal bone in hallux valgus: A preliminary study utilizing a weight bearing extremity CT," Foot and Ankle Surgery, vol. 19, 2013, pp. 155-161.
"Futura Forefoot Implant Arthroplasty Products," Tornier, Inc., 2008, 14 pages.
"Hat-Trick Lesser Toe Repair System, Foot and Ankle Technique Guide, Metatarsal Shortening Osteotomy Surgical Technique," Smith & Nephew, 2014, 16 pages.
"Hat-Trick Lesser Toe Repair System," Smith & Nephew, Brochure, Aug. 2014, 12 pages.
"Hoffmann II Compact External Fixation System", Stryker, Brochure, Literature No. 5075-1-500, 2006, 12 pages.
"Hoffmann II Micro Lengthener", Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Patient to Patient Precision, Accu-Cut, Osteotomy Guide System, BioPro, Foot & Ankle International Journal, vol. 23, No. 8, Aug. 2002, 2 pages.
Blomer "Problems and complications of knee endoprostheses from a manufacturer's point of view" Orthopade 200, 29, pp. 688-696, English Abstract.
"Prophecy Inbone Preoperative Navigation Guides", Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Smith & Nephew scores a Hat-Trick with its entry into the high-growth hammer toe repair market, Smith & Nephew, Jul. 31, 2014, 2 pages.

(56) References Cited

OTHER PUBLICATIONS

"Lag Screw Target Bow," Stryker Leibinger GmbH & Co. KG, Germany 2004, 8 pages.
Anderson et al., "Uncemented STAR Total Ankle Protheses" Journal of Bone Joint Surgery America, Sep. 2004, Abstract of Article, pp. 6.
Coetzee et al., "The Lapidus Procedure: A Prospective Cohort Outcome Study," Foot & Ankle International, vol. 25, No. 8, Aug. 2004, pp. 526-531.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
D'Amico et al., "Motion of the First Ray: Clarification Through Investigation," Journal of the American Podiatry Association, vol. 69, No. 1, Jan. 1979, pp. 17-23.
Dayton et al., "Biwinged Excision for Round Pedal Lesions," The Journal of Foot and Ankle Surgery, vol. 35, No. 3, 1996, pp. 244-249.
Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, pp. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.

(56) References Cited

OTHER PUBLICATIONS

Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.
Dayton "Evidence-Based Bunion Surgery: A Critical Examination of Current and Emerging Concepts and Techniques" Springer International Publishing, 2017, pp. 254.
Dayton et al. "Biomechanical Characteristics of Biplane Multiplanar Tension-Side Fixation for Lapidus Fusion" The Journal of Foot & Ankle Surgery, 2018, pp. 1-5.
Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al. "Comparison of Radiographic Measurements Before and After Triplane Tarsometatarsal Arthrodesis for Hallux Valgus" The Journal of Foot & Ankle Surgery 59, 2020, pp. 291-297.
Curran et al. "Functional Capabilities After First Metatarsal Phalangeal Joint Arthrodesis Using a Locking Plate and Compression Screw Construct" The Journal of Foot & Ankle Surgery, 2021, pp. 1-5.
De Carvalho, et al. "Automated Three-dimensional distance and coverage mapping of hallux valgus: a case-control study" Journal of Foot and Ankle, 2022;16(1), pp. 5.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
De Heer et al., "Procedure-Specific Hardware Removal After Evans Osteotomy" Journal of the American Podiatric Medical Association, vol. 110, No. 2, Mar./Apr. 2020, pp. 1-7.
DeCarbo et al., "Locking Plates: Do They Prevent Complications?," Podiatry Today, Apr. 2014, 7 pages.
DeCarbo et al., "Resurfacing Interpositional Arthroplasty for Degenerative Joint Disease of the First Metatarsalphalangeal Joint," Podiatry Management, Jan. 2013, pp. 137-142.

* cited by examiner

APPARATUS, SYSTEM, AND METHOD FOR GENERATING PATIENT-SPECIFIC IMPLANTS AND/OR INSTRUMENTATION

CROSS-REFERENCE TO RELATED APPLICATIONS

This application claims the benefit of U.S. Provisional Application No. 63/387,080, filed Dec. 12, 2022, entitled APPARATUS, SYSTEM, AND METHOD FOR GENERATING PATIENT-SPECIFIC IMPLANTS AND/OR INSTRUMENTATION. This application is also a continuation-in-part of U.S. patent application Ser. No. 18/129,151 filed on Mar. 31, 2023, entitled APPARATUS, SYSTEM, AND METHOD FOR PATIENT-SPECIFIC INSTRUMENTATION, which claims the benefit of U.S. Provisional Patent Application No. 63/326,249 filed Mar. 31, 2022, entitled PATIENT-SPECIFIC SURGICAL METHODS AND INSTRUMENTATION, which are hereby incorporated by reference in their entirety.

TECHNICAL FIELD

The present disclosure relates to surgical devices, systems, instruments, and methods. More specifically, the present disclosure relates to patient-specific guides, implants, instruments, and/or methods of designing and using the same.

BACKGROUND

Various bone conditions may be corrected using surgical procedures, in which one or more tendons, ligaments, and/or bones may be cut, replaced, repositioned, reoriented, reattached, fixated and/or fused. These surgical procedures require the surgeon to properly locate, position, and/or orient one or more osteotomy cuts, fixation guides, fixators, bone tunnels, points of attachment for ends of grafts or soft tissue and the like Planning, preparing for, and making these osteotomy cuts with conventional techniques and/or instruments can place pressure on a surgeon to make accurate cuts for an osteotomy that enable a successful outcome for a surgical procedure. Conventional cutting tools generally do not provide guidance or assistance to a surgeon in performing the osteotomy in a desired location and manner. Instead, a surgeon may be left to their own manual dexterity and experience in guiding a cutting tool. What is needed is one or more resection guides to orienting, planning, preparing for, initiating, and/or completing an osteotomy. In particular, a resection guide that facilitates precise and accurate cuts, resections, or dissections using a rotary cutting tool, such as a burr or drill is needed. Existing solutions for guiding orthopedic surgical procedures are inadequate and error prone.

SUMMARY

The various apparatus, devices, systems, and/or methods of the present disclosure have been developed in response to the present state of the art, and in particular, in response to the problems and needs in the art that have not yet been fully solved by currently available technology.

In one general aspect, an osteotomy system may include one or more temporary fasteners configured to engage one or more bones of a patient's foot. The osteotomy system may also include a pivoting resection guide having: a first bone attachment feature configured to receive at least one of one or more temporary fasteners, the first bone attachment feature having a patient-specific bone engagement surface configured to engage a cortical bone surface of the one or more bones, the patient-specific bone engagement surface is at least partially determined based on a bone model of a patient's foot, the bone model defined based on medical imaging of the patient's foot; a cutter guide coupled between the first bone attachment feature and the second bone attachment feature, the cutter guide configured to guide a cutting tool as the cutter guide rotates about a pivot axis coupled to the first bone attachment feature and the second bone attachment feature.

In one general aspect, an osteotomy system may include one or more temporary fasteners configured to engage one or more bones of a patient's foot. The osteotomy system may also include a pivoting resection guide having: a first bone attachment feature configured to receive at least one of one or more temporary fasteners; a second bone attachment feature configured to receive at least one of one or more temporary fasteners; a cutter guide coupled between the first bone attachment feature and the second bone attachment feature, the cutter guide configured to guide a cutting tool as the cutter guide rotates about a pivot axis coupled to the first bone attachment feature and the second bone attachment feature.

Implementations may include one or more of the following features. The osteotomy system having: a cutting tool having a proximal end and a distal end, the cutting tool configured to be deployed within an opening in the cutter guide; a handle having: a distal handle end having a handle coupler configured to engage with the cutter guide; a proximal handle end opposite the distal handle end; an opening that extends from the proximal handle end to the distal handle end and is coaxial with a longitudinal axis of the handle; where the handle is configured to pass the cutting tool through the opening and couple to the cutter guide to form a first-class lever that magnifies a load force applied to a bone in contact with the cutting tool near the distal end of the cutting tool based on an effort force applied by a user toward the proximal handle end.

The osteotomy system where the pivot axis may include a fulcrum of the first-class lever and the load force may include the effort force multiplied by a lever arm length, the lever arm length having a distance between the fulcrum and a point toward the proximal handle end where the effort force is applied.

The osteotomy system where the cutting tool may include: a body having: a drive section near the proximal end; a cutting section near the distal end, the cutting section having a predetermined length configured to extend from one cortex of a bone to an opposite cortex of the bone when the cutting tool is used to resect the bone; and a guide section between the drive section and the cutting section. The osteotomy system where the body of the cutting tool is an elongate body having a round cross section and where the cutting section has a first diameter and the guide section has a second diameter, the first diameter being smaller than the second diameter.

The osteotomy system where the cutter guide may include an opening that extends from a proximal end of the cutter guide to a distal end of the cutter guide, the opening of the cutter guide sized and shaped to accept the cutting tool and where the body of the cutting tool is an elongate body having a round cross section and the cutting tool may include a collar between the cutting section and the drive section, the collar having a diameter that permits a close fit of the collar within the opening of the cutter guide.

The osteotomy system where the handle coupler may include: a recess that extends from the distal handle end towards the proximal handle end, the recess having a cross-sectional shape and size configured to accept a proximal end of the cutter guide into the recess; at least one arm that extends radially from the handle near the distal handle end, the at least one arm configured to engage with one of the first bone attachment feature and the second bone attachment feature.

The osteotomy system where the first bone attachment feature may include: a body having: a superior side; an inferior side; a medial side; a lateral side; a proximal side; a distal side; an opening that extends from the superior side to the inferior side, the opening configured to receive one of the one or more temporary fasteners; and a first coupler configured to engage with the cutter guide between the first bone attachment feature and the second bone attachment feature; and a first height from the superior side to the inferior side.

The osteotomy system where the inferior side of the first bone attachment feature may include a bone engagement surface configured to engage a cortical bone surface of the one or more bones. The osteotomy system where the bone engagement surface is at least partially determined based on a bone model of a patient's foot, the bone model defined based on medical imaging of the patient's foot. The osteotomy system where the first coupler is configured to retain a pivot arm of the cutter guide and enable the cutter guide to rotate about the pivot arm.

The osteotomy system where the second bone attachment feature may include: a body having: a superior side; an inferior side; a medial side; a lateral side; a proximal side; a distal side; an opening that extends from the superior side to the inferior side, the opening configured to receive one of the one or more temporary fasteners; and a second coupler configured to engage with the cutter guide between the first bone attachment feature and the second bone attachment feature; a second height from the superior side to the inferior side; and where the first coupler, second coupler, first height, and second height correlate to define a trajectory for the cutter guide towards the one or more bones.

The osteotomy system where: the first coupler engages the cutter guide at a first angle that is perpendicular to the distal side of the first bone attachment feature; the second coupler engages the cutter guide at a second angle that is perpendicular to the distal side of the second bone attachment feature; and the first height and second height are defined such that the trajectory of the cutter guide extends substantially perpendicular to a longitudinal axis of one of the one or more bones to be resected.

The osteotomy system where the first angle is not a right angle with respect to the distal side of the first bone attachment feature and the second angle is not a right angle with respect to the distal side of the second bone attachment feature and the first height and second height are defined such that the trajectory of the cutter guide extends at an angle that is not perpendicular to the longitudinal axis of one of the one or more bones to be resected.

The osteotomy system where the first coupler may include: a proximal arm that extends from a first side of the cutter guide at a first arm angle towards the first bone attachment feature; a proximal arm groove toward a distal end of the proximal arm; a proximal arm retainer configured to engage with a body of the first bone attachment feature and engage with the proximal arm groove to couple the proximal arm to the first bone attachment feature; and where the second coupler may include: a distal arm that extends from a second side of the cutter guide at a second arm angle towards the second bone attachment feature; a distal arm groove toward a distal end of the distal arm; a distal arm retainer configured to engage with a body of the second bone attachment feature and engage with the distal arm groove to couple the distal arm to the second bone attachment feature. Implementations of the described techniques may include hardware, a method or process, or a computer tangible medium.

In one general aspect, an osteotomy system may include a cuneiform fastener configured to engage a medial cuneiform of a patient's foot. The osteotomy system may also include a metatarsal fastener configured to engage a first metatarsal of a patient's foot.

The system may furthermore include a pivoting resection guide configured to resect the medial cuneiform and the first metatarsal, the pivoting resection guide having: a cuneiform attachment feature an opening configured to receive the cuneiform fastener; a first metatarsal attachment feature configured to receive the metatarsal fastener; a cuneiform cutter guide configured to be removably coupled between the cuneiform attachment feature and the first metatarsal attachment feature, the cuneiform cutter guide configured to guide a cutting tool as the cuneiform cutter guide pivots about a pivot axis that extends between the cuneiform attachment feature and the first metatarsal attachment feature; a first metatarsal cutter guide configured to be removably coupled between the cuneiform attachment feature and the first metatarsal attachment feature, the first metatarsal cutter guide configured to guide a cutting tool as the first metatarsal cutter guide pivots about the pivot axis that extends between the cuneiform attachment feature and the first metatarsal attachment feature. System may in addition include a cutting tool having: an elongate body having a proximal end and a distal end; a drive section near the proximal end of the elongate body; a cutting section near the proximal end of the elongate body; and a guide section between the drive section and the cutting section, the cutting tool configured to be deployed within an opening in one of the cuneiform cutter guide and the first metatarsal cutter guide.

The system may moreover include a handle having: a distal handle end having a handle coupler configured to engage with one of the cuneiform cutter guide and the first metatarsal cutter guide; a proximal handle end opposite the distal handle end; an opening that extends from the proximal handle end to the distal handle end and is coaxial with a longitudinal axis of the handle.

The system may also include where the handle is configured to pass the cutting tool through the opening and couple to one of the cuneiform cutter guide and the first metatarsal cutter guide to form a first-class lever that magnifies a load force applied to a bone in contact with the cutting tool near the distal end of the cutting tool based on an effort force applied by a user near the proximal handle end.

Implementations may include one or more of the following features. The osteotomy system where the cuneiform cutter guide may include: a proximal arm that extends from a first side of the cuneiform cutter guide at a first arm angle towards the cuneiform attachment feature; a proximal arm groove toward a distal end of the proximal arm; a proximal arm retainer configured to engage with a body of the cuneiform attachment feature and engage with the proximal arm groove to couple the proximal arm to the cuneiform attachment feature; a distal arm that extends from a second side of the cuneiform cutter guide at a second arm angle towards the first metatarsal attachment feature; a distal arm groove toward a distal end of the distal arm; a distal arm retainer configured to engage with a body of the first metatarsal attachment feature and engage with the distal arm groove to couple the distal arm to the first metatarsal attachment feature; and where at least one of a length of the proximal arm, a length of the distal arm, a size of the first arm angle and a size of the second arm angle are defined such that operation of the cutting tool by way of the cuneiform cutter guide forms an osteotomy of a predefined trajectory in the cuneiform of the patient.

The osteotomy system where the first metatarsal cutter guide may include: a proximal arm that extends from a first side of the first metatarsal cutter guide at a first arm angle towards the cuneiform attachment feature; a proximal arm groove toward a distal end of the proximal arm; a proximal arm retainer configured to engage with a body of the cuneiform attachment feature and engage with the proximal arm groove to couple the proximal arm to the cuneiform attachment feature; a distal arm that extends from a second side of the first metatarsal cutter guide at a second arm angle towards the first metatarsal attachment feature; a distal arm groove toward a distal end of the distal arm; a distal arm retainer configured to engage with a body of the first metatarsal attachment feature and engage with the distal arm groove to couple the distal arm to the first metatarsal attachment feature; and where at least one of a length of the proximal arm, a length of the distal arm, a size of the first arm angle and a size of the second arm angle are defined such that operation of the cutting tool by way of the first metatarsal cutter guide forms an osteotomy of a predefined trajectory in the first metatarsal of the patient.

The osteotomy system where the cuneiform attachment feature and the first metatarsal attachment feature each couple to one of the cuneiform cutter guide and the first metatarsal cutter guide by a pair of toolless couplers. Implementations of the described techniques may include hardware, a method or process, or a computer tangible medium.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 4 illustrates an exemplary system configured to generate one or more patient-specific instruments configured to address a bone condition, according to one embodiment.

FIGS. 15A-15D illustrate views of an example pivot resection guide, according to one embodiment.

DETAILED DESCRIPTION

Figures 1A, 1B:
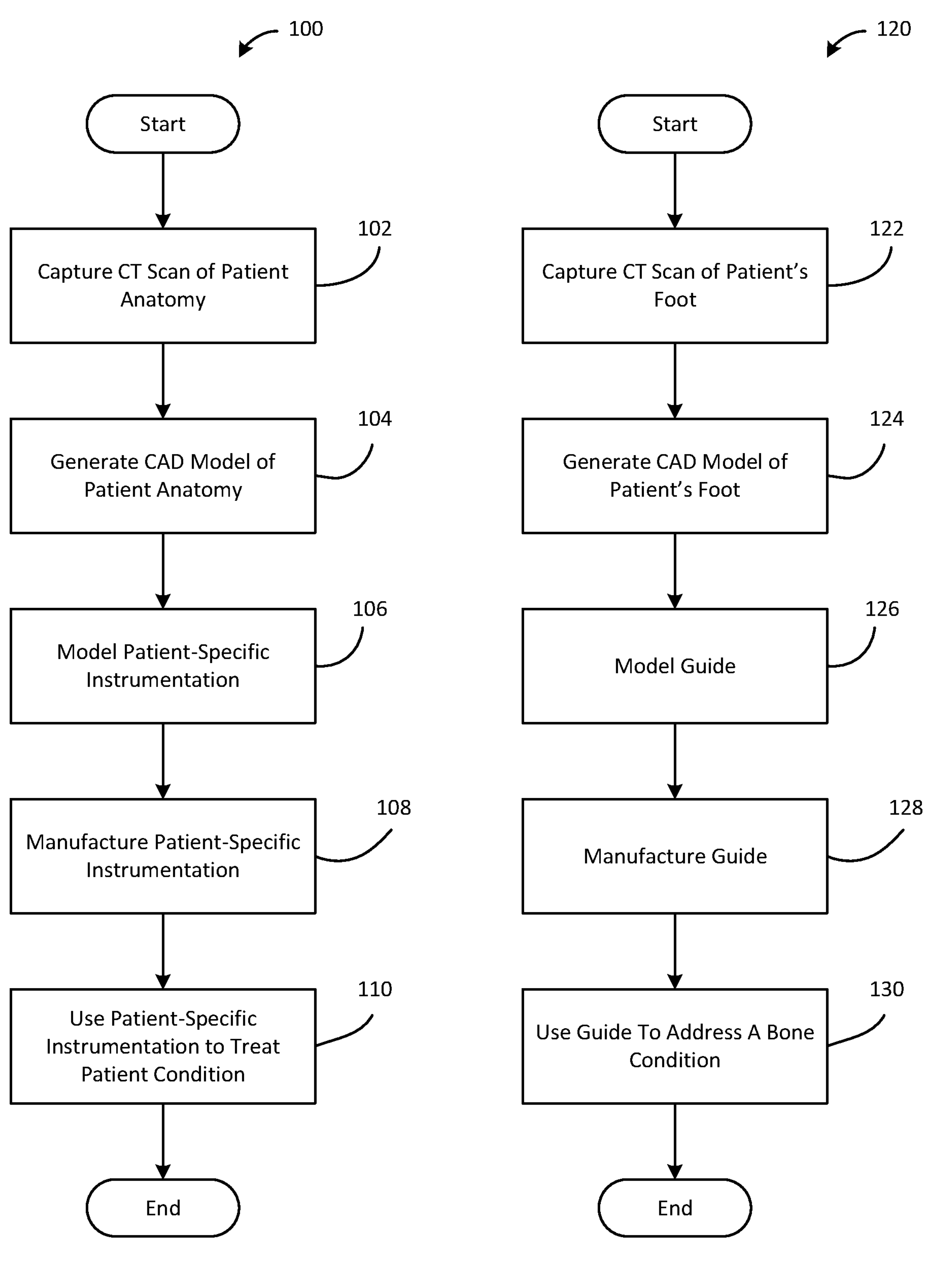
FIG. 1A is a flowchart diagram depicting a method for remediating a condition, according to one embodiment.
FIG. 1B is a flowchart diagram depicting a method for remediating a condition, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

"Patient-specific positioning guide" or "Patient-specific positioner" refers to an instrument, implant, positioner, structure, or guide designed, engineered, and/or fabricated for use as a positioner with a specific patient. In one aspect, a patient-specific positioning guide is unique to a patient and may include features unique to the patient such as patient-specific offsets, translation distances, openings, angles, orientations, anchor a surface contour or other features.

"Patient-specific cutting guide" refers to a cutting guide designed, engineered, and/or fabricated for use with a specific patient. In one aspect, a patient-specific cutting guide is unique to a patient and may include features unique to the patient such as a surface contour or other features.

"Patient-specific resection guide" refers to a guide designed, engineered, and/or fabricated for use in resection for a specific patient. In one aspect, a patient-specific resection guide is unique to a patient and may include features unique to the patient such as a surface contour or other features.

"Patient-specific trajectory guide" refers to a trajectory guide designed, engineered, and/or fabricated for use with a specific patient. In one aspect, a patient-specific trajectory guide is unique to a single patient and may include features unique to the patient such as a surface contour or other features.

"Patient specific instrument" (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient specific instrument is unique to a single patient and may include features unique to the patient such as a surface contour, component position, component orientation, and/or other features. In other aspects, one patient specific instrument may be useable with a number of patients having a particular class of characteristics.

As used herein, a "handle" or "knob" refers to a structure used to hold, control, or manipulate a device, apparatus, component, tool, or the like. A "handle" may be designed to be grasped and/or held using one or two hands of a user. In certain embodiments, a handle or knob may be an elongated structure. In one embodiment, a knob may be a shorter stubby structure.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases, implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g., PLLA) and/or others. In one embodiment, a body may include a housing or frame, or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces. In certain embodiments, a bone engagement surface is an implementation and/or part of a structure that implements a bone engagement feature.

"Bone engagement feature" refers to a structure, feature, component, aspect configured to contact, touch, abut, and/or engage with a bone, a bone part, bony topography (e.g., bone spurs and calcifications), anatomical bone feature, and/or a bone fragment. A bone engagement feature may enable temporary engagement with a bone or bone fragment or permanent engagement with a bone or bone fragment. A bone engagement feature may include a bone engagement surface and/or a body section that supports the bone engagement surface. In certain embodiments, a bone engagement feature may include a bone probe or a joint seeker. In one embodiment, a bone engagement feature may include a landmark registration feature. Alternatively, or in addition, a bone engagement feature can include a bone attachment feature configured to engage with bone and/or to cooperate with a fastener to engage with bone.

A patient-specific bone engagement feature is a bone engagement feature that includes one or more aspects that are patient-specific. The patient-specific aspects can include, but are not limited to, a surface contour, a contour for a part of a surface, a position for a resection feature, a size, shape and/or configuration of a resection feature, a position, size, shape, and/or number of bone attachment features, or the like.

"Frangible" refers to a type of material designed, engineered, and/or configured to break easily under an expected force. Frangible objects may be designed to break easily under the expected force to provide a safety feature, a convenience feature, or the like. Frangible objects can be made from metal, plastic, ceramics, wood, paper, or the like. Frangible also includes something that is breakable or fragile; especially something that is intentionally made so. (Search "frangible" on wordhippo.com. WordHippo, 2023. Web. Accessed 11 May 2023. Modified.)

As used herein, "side" refers to a structure or part of a structure including, but not limited to one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021.

Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant, instrument, anatomical structure, or other structure refers to a side that is anterior to other sides of the structure in relation to a patient when the structure is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Tissue" refers to a structure that makes up a one or more anatomical structures of a patient (i.e., human or animal). Tissue can be soft tissue or hard tissue. "Soft tissue" refers to tissue of a patient (i.e., human or animal). Examples of soft tissue include but are not limited to, skin, ligament, tendon, fascia, fat muscle, fibrous tissue, blood vessels, lymph vessels, brain tissue, and/or nerves. "Hard tissue" refers to any human or animal tissue that is not soft tissue. Examples of hard tissue include bone, teeth, tooth enamel, dentin, cementum, cartilage, or the like.

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

As used herein, an "indicator" refers to an apparatus, device, component, system, assembly, mechanism, hardware, software, firmware, circuit, module, set of data, text, number, code, symbol, a mark, or logic structured, organized, configured, programmed, designed, arranged, or engineered to convey information or indicate a state, condition, mode, context, location, or position to another apparatus, device, component, system, assembly, mechanism, hardware, software, firmware, circuit, module, and/or a user of an apparatus, device, component, system, assembly, mechanism, hardware, software, firmware, circuit, module that includes, or is associated with the indicator. The indicator can include one or more of an audible signal, a token, a presence of a signal, an absence of a signal, a tactile signal, a visual signal or indication, a visual marker, a visual icon, a visual symbol, a visual code, a visual mark, and/or the like. In certain embodiments, "indicator" can be used with an adjective describing the indicator. For example, a "mode indicator" is an indicator that identifies or indicates a mode.

"Boundary" refers to a structure, line, or area where an object, surface, line, area, or operation is or is expected to begin and/or end. A boundary can be similar to a border.

"Landmark registration feature" or "Landmark" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. In the context of bones of a patient a landmark registration feature can include any protuberance, void, divot, concave section, sesamoid, bone spur or other feature on, or extending from, a bone of a patient. A landmark refers to any structure of an anatomical structure that is referenced, contacted, engaged with and/or associated with a landmark registration feature.

"Probe bone engagement surface" refers to a bone engagement surface on one surface of a probe or part of a probe.

"Bone attachment feature" refers to a structure, feature, component, aspect configured to securely connect, couple, attach, and/or engage a structure, component, object, or body with a bone and/or a bone fragment. Examples of a bone attachment feature, include, but are not limited to, a pin, a spike, a tine, a K-wire, a screw, or other fastener alone, or in combination with, a hole, passage, and/or opening.

As used herein, "patient-specific osteotomy procedure" refers to an osteotomy procedure that has been adjusted, tailored, modified, or configured to specifically address the needs or desires or a particular patient. In certain aspects, one patient-specific osteotomy procedure may be useable in connection with only one patient. In other aspects, one patient-specific osteotomy procedure may be useable with a number of patients having a particular class of characteristics.

"Ankle fusion procedure" refers to a surgical procedure that seeks to immobilize an ankle joint of a patient. The surgery fuses two or more bones of the ankle of the patient. The surgery involves the use of screws, plates, medical nails, and other hardware or fasteners to achieve bone union. Ankle fusion is considered to be the gold standard for treatment of end-stage ankle arthritis. Ankle fusion trades joint mobility for relief from pain. (Search "ankle fusion" on Wikipedia.com Dec. 21, 2022. CC-BY-SA 3.0 Modified. Accessed Jun. 28, 2023.) An ankle fusion procedure may also be referred to as ankle arthrodesis, talocrural joint fusion, tibiotalar arthrodesis, and tibiotalocalcaneal arthrodesis. An ankle fusion procedure can be performed using a variety of approaches to the ankle including an anterior approach, a posterior approach, a lateral approach and a medial approach. Each approach may use common or different instrumentation or implants for the procedure.

"Deformity" refers to any abnormality in or of an organism, a part of an organism, or an anatomical structure of a patient that appears or functions differently than is considered normal, or is common, in relation to the same organism, a part of an organism, or an anatomical structure of other subjects of the same species as the patient. (Search "deformity" on Wikipedia.com Jun. 13, 2023. CC-BY-SA 3.0 Modified. Accessed Jun. 28, 2023.)

A "deformed position" refers to an anatomical structure positioned to form, include, or is at least part of a deformity. A "corrected position" refers to an anatomical structure positioned to remediate, correct, eliminate, and/or overcome a deformity.

"User directions" refers to any request, instruction, direction, input, feedback, prescription, designation, order, directive, or the like from a user of an apparatus, system, device, component, subsystem, or other object. User directions can be created, sent, and/or received in a variety of forms and/or formats, including, but not limited to, a user action in a user interface, a prescription, a form, a conversation, an electronic mail message, a text message, a gesture by the user, or the like. In the context of an osteotomy procedure, user directions can include a set of default settings or choices or instructions for fabrication of a patient-specific instrument or set of instruments, an online form completed by a user (e.g., surgeon), a set of modifications to an original set of user directions, and the like.

"Position" refers to a place or location. (Search "position" on wordhippo.com. WordHippo, 2022. Web. Modified. Accessed 9 Aug. 2022.) Often, a position refers to a place or location of a first object in relation to a place or location of another object. One object can be positioned on, in, or relative to a second object. In addition, a position can refer to a place or location of a first object in relation to a place or location of another object in a virtual environment. For example, a model of one object can be positioned relative to a model of another object in a virtual environment such as a modeling software program.

"Predetermined Position" refers to a position that is decided, determined, finalized, and/or defined earlier in time. In certain embodiments, a predetermined position is a desired, designed, and/or engineered position of a first object in relation to a second object. Thus, a predetermined position is a planned position for the two objects in relation to each other. In certain embodiments, one or both of the two objects may be moved relative to each other to accomplish the predetermined position and the predetermined position may become the final position. In other embodiments, the two objects may be moved towards the predetermined position but may not reach the exact predetermined position due to some impediment and/or interference or a decision to change the predetermined position to a new position. In certain aspects, a predetermined position may be a position that is decided after a process of recommendation, review, and/or analysis, and final approval such that a position may not become a predetermined position until the process is completed. For example, in a medical patient-specific instrument or technique design process a position may not become the predetermined position until a surgeon or other doctor provides final approval for the position.

"Contour" refers to an outline representing or bounding a shape or form of an object. Contour can also refer to an outside limit of an object, area, or surface of the object. (Search "contour" on wordhippo.com. WordHippo, 2023. Web. Modified. Accessed 13 Jun. 2023.)

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly. In one embodiment, a stop may be used to manage and/or control a cutting tool.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like. Fixation refers to the act of deploying or using a fixator to fix two structures together.

As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. In certain embodiments, the term anchor may be used as an adjective that describes a function, feature, or purpose for the noun the adjective 'anchor' describes. For example, an anchor hole is a hole that serves as or can be used as an anchor. In another embodiment, an anchor may be a hole or opening or a plurality of holes or openings.

"Connector" refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited to any fastener. A connector can be a slot, channel, tube, pipe, opening, or other structure the connects and/or joins two slots, channels, tubes, pipes, openings, or other structures.

"Clearance" refers to a space or opening that provides an unobstructed area to permit one object to move freely in relation to another object.

"Correction," in a medical context, refers to a process, procedure, device, instrument, apparatus, system, implant, or the like that is configured, designed, developed, fabricated, configured, and/or organized to adjust, translate, move, orient, rotate, or otherwise change an anatomical structure from an original position, location, and/or orientation to a new position, location, and/or orientation that provides a benefit to a patient. The benefit may be one of appearance, anatomical function, pain relief, increased mobility, increased strength, and the like.

"Uniplanar correction" refers to a medical correction, which can include an osteo correction, in one plane (e.g., one of a sagittal plane, a transverse plane, and a coronal/frontal plane) of an anatomical structure such as a foot, hand, or body of a patient.

"Biplanar correction" refers to a medical correction, which can include an osteo correction, in two planes (e.g., two of a sagittal plane, a transverse plane, and a coronal/frontal plane) of an anatomical structure such as a foot, hand, or body of a patient.

"Triplane correction" refers to a medical correction, which can include an osteo correction, in three planes (e.g., all three planes of a sagittal plane, a transverse plane, and a coronal/frontal plane) of an anatomical structure such as a foot, hand, or body of a patient.

"Wedge Angle" refers to an angle measured between two surfaces of a wedge shape. A wedge angle can also be an angle between two sides of a wedge shape.

"Bone Wedge" refers to a geometric shape of one or more bones characterized by having two flat, planar, and/or inclined sides or surfaces that converge to form an edge. A bone wedge resembles a triangular prism, with one end wider or thicker than the other. (© ChatGPT August 3 Version, Modified, accessed chat.openai.com/chat Sep. 28, 2023). In certain implementations, the edge formed by the two converging sides is within a bone or set of bones from which the bone wedge is formed. In other implementations, the edge formed by the two converging sides is outside of a bone or set of bones from which the bone wedge is formed.

"Window" refers to an opening and/or a plurality of openings in a body, side, wall, side door, roof, vehicle, system, component, or other structure that allows the passage of electromagnetic radiation including radio ways, x-rays, visible light, light, and the like. A window may also permit passage of sound, gases, fluids, liquids, or other elements. (Search "window" on Wikipedia.com Aug. 31, 2022. Modified. Accessed Sep. 21, 2022.). A window can be opaque, semi-opaque, translucent, radiolucent, or transparent. A window can include a single opening having a single geometric shape or a plurality of openings each of a single geometric shape or combination of a variety of geometric shapes. In certain embodiments, a window may be referred to as a radiolucent window. A radiolucent window may permit passage of some or all radio ways through the window.

"Resection Window" refers to a window designed, engineered, configured, manufactured, developed, and/or fabricated to facilitate performing a resection step or procedure.

"Probe" refers to a medical instrument used to explore, identify, locate, or register to, wounds, organs, and/or anatomical structures including a joint or an articular surface. In certain embodiments, a probe can be thin and/or pointed. In one embodiment, a probe is connected, integrated with, and/or coupled to another structure or instrument. In such an embodiment, the probe may serve to facilitate proper positioning of the another structure or instrument. For example, the probe may be used to identify and/or locate a particular anatomical structure and the positioning of the probe may then cause the connected structure or instrument to also be positioned in a desired location relative to one or more anatomical structures.

As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

"Friction fit" refers to a type of joint or connection that is created between two components by means of friction. A joint or connection that is formed using a friction fit may or may not include the use of additional fasteners such as screws, bolts, or adhesives. In a friction fit, the components are designed or configured to fit tightly together, creating enough friction between the surfaces to hold them securely in place, at least temporarily. The friction force is generated by the compressive force that is experienced between the components and can be strong enough to prevent the components from separating under normal conditions. (© ChatGPT March 23 Version, Modified, accessed chat.openai.com/chat May 2, 2023).

As used herein, "osteotomy procedure" or "surgical osteotomy" or "osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy, a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

"Midfoot Bone" refers to any bone of a foot of a human or animal between the ankle and the toes. For example, in a human a midfoot bone can include any of the metatarsus including a first metatarsal bone, second metatarsal bone, third metatarsal bone, fourth metatarsal bone, and fifth metatarsal bone; a medial cuneiform bone, an intermediate cuneiform bone, a lateral cuneiform bone, a cuboid bone, a talus bone, and the like.

"Metatarsal" is a bone of a foot of a human or animal. In a human, a foot typically includes five metatarsals which are identified by number starting from the most medial metatarsal, which is referred to as a first metatarsal and moving laterally the next metatarsal is the second metatarsal, and the naming continues in like manner for the third, fourth, and fifth metatarsal. The metatarsal bone includes three parts a base which is a part that is at a proximal end of the metatarsal, a head which is a part that is at a distal end of the metatarsal, and a shaft or neck connects the base to the head.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

"Metaphyseal Diaphyseal Junction" or "MDJ" refers to an area of a long bone between the Metaphysis and the Diaphysis. This area can also include or be referred to as the epiphyseal plate (growth) plate. For certain surgical procedures, performing an osteotomy at or near the metaphyseal diaphyseal junction may be advantageous and desirable to promote rapid fusion of two cut faces formed in the osteotomy and bone growth to close the osteotomy, and/or may mitigate the risk of a nonunion of the osteotomy.

"Vertex" refers to a point at which lines, structures, trajectories, or pathways intersect. (Search "vertex" on wordhippo.com. WordHippo, 2023. Web. Modified. Accessed 13 Jun. 2023.)

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position. Certain bones such as a metatarsal bone can include a base as one structural component of the bone.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

"Positioner" or "positioning guide" refers to any structure, apparatus, surface, device, system, feature, or aspect configured to position, move, translate, manipulate, or arrange one object in relation to another. In certain embodiments, a positioner can be used for one step in surgical procedure to position, arrange, orient, and/or reduce one bone or bone fragment relative to another. In such embodiments, the positioner may be referred to as a bone positioner. In certain embodiments, the term positioner or positioning guide may be preceded by an adjective that identifies the structure, implement, component, or instrument that may be used with, positioned by, and/or guided by with the positioner. For example, a "pin positioner" may be configured to accept a pin or wire such as a K-wire and serve to position or place the pin relative to another structure such as a bone.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Rotation guide" or "rotator" refers to any structure, apparatus, surface, device, system, feature, or aspect configured, designed, engineered, or fabricated to rotate or aid a user in the rotation of one structure relative to another structure. In certain embodiments, a rotation guide or rotator may be used to help a surgeon rotate one or more bones, parts of bones, bone fragment, an implant, or other anatomical structure, either alone or in relation to another one or more bones, parts of bones, bone fragments, implants, or other anatomical structures.

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Trajectory" refers to a path a body travels or a path configured for a body to travel through space. (Search "trajectory" on wordhippo.com. WordHippo, 2023. Web. Modified. Accessed 13 Jun. 2023.)

"Metatarsal base resection guide" refers to a resection guide designed, engineered, fabricated, or intended for use with, one, in, or about a base part, section, surface, portion, or aspect of a metatarsal for one or more steps of a medical procedure. The metatarsal base resection guide may be used to form an osteotomy, to resect a wedge for a closing wedge procedure, resect a bone wedge that preserves a cortical layer of bone opposite the resected bone wedge, form an osteotomy that uniplanar wedge, a biplanar wedge, or a triplane wedge. Various embodiments of a metatarsal base resection guide may be used on a medial surface, a dorsal surface, a lateral surface, or a plantar surface of a single metatarsal. Alternatively, or in addition, various embodiments of a metatarsal base resection guide can be used on two or more metatarsals.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Fastener guide" or "reducer" refers to any structure, apparatus, surface, device, system, feature, or aspect configured, designed, engineered, or fabricated to guide or direct a fastener into a bone as part of deploying the fastener. Examples of a fastener guide include an opening in a structure that is sized and/or oriented for deployment of a fastener such as a bone screw, a reference pin for aligning a fastener for deployment at a desired orientation and/or trajectory, and the like.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers to the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while non-parametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g., physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

"Reference" refers to any apparatus, structure, device, system, component, marking, and/or indicator organized, configured, designed, engineered, and/or arranged to serve as a source of information or a point of comparison used to support or establish knowledge, truth, or quality. (© ChatGPT January 9 Version, Modified, accessed chat.openai.com/chat Jan. 28, 2023). In certain embodiments, a reference can serve as a starting point or initial position for one or more steps in a surgical procedure. A reference may be a type of fiducial. In certain embodiments, "reference" can be with an adjective describing the reference. For example, a "model reference" is a reference within a model such as a computer model. A model reference refers to any feature, aspect, and/or component within a model. Examples of a model reference include, but are not limited to, a point, a plane, a line, a plurality of points, a surface, an anatomical structure, a shape, or the like. An "anatomical reference" is a reference within, on, near, or otherwise associated with an anatomical structure such as a bone. A reference (e.g., model, actual, virtual, and/or real) may also be referred to as a reference feature.

"Reference feature" refers to a feature configured for use as a point, plane, axis, or line of reference (aka a reference). A reference or reference feature can be used to position, measure, orient, fixation, couple, engage, and/or align one object or structure with another object or structure. In certain embodiments, a reference or reference feature can serve as a baseline, a ground truth, a waypoint, a control point, a landmark, and/or the like. A reference feature can facilitate moving from one coordinate system or frame of reference in a virtual environment to a position, location, frame of reference, environment, or orientation on, or in, an actual object, structure, device, apparatus, anatomical structure, or the like. Advantageously, a reference feature can coordinate objects, models, or structures in a digital or virtual model or representation with corresponding objects or structures (e.g., anatomical structures) of actual physical objects or structures. Said another way, a reference feature can serve to map from a virtual or modeled object to an actual or physical object.

As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "alignment feature," "securing feature," "placement feature," "protruding feature," "engagement feature," "disengagement feature," "resection feature", "guide feature", "alignment feature," and the like.

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

As used herein, a "protrusion" refers to a structure or portion of a structure that protrudes or extends from at least one other structure such as a surface of the at least one other structure. Generally, the other structure is connected to, or in contact with, the protrusion.

"Set" refers to a collection of objects. A set can have zero or more objects in the collection. Generally, a set includes one or more objects in the collection.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo.com. WordHippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of manmade and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

"Fusion" refers to a natural process of bone growth and generation in which two separate bones and/or bone fragments grow together as new bone grows when the two separate bones and/or bone fragments contact each other. Often, fusion is facilitated by compression of the two separate bones and/or bone fragments towards each other.

As used herein, a "resection" refers to a method, procedure, or step that removes tissue from another anatomical structure or body. A resection can include an osteotomy that cuts through a bone or other tissue because the osteotomy still removes at least a minimal amount of tissue. A resection is typically performed by a surgeon on a part of a body of a patient. A resection is one type of osteotomy. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is "resected".

As used herein, "image registration" refers to a method, process, module, component, apparatus, and/or system that seeks to achieve precision in the alignment of two images. As used here, "image" may refer to either or both an image of a structure or object and another image or a model (e.g., a computer-based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

"Register" or "Registration" refers to an act of aligning, mating, contacting, engaging, or coupling one or more parts and/or surfaces of one object in relation to one or more parts and/or surfaces of another object. Often, the one or more parts and/or surfaces of one object include protrusions and/or depressions that are the inverse or mirror configuration of protrusions and/or depressions of one or more parts and/or surfaces of the other object.

"Registration key" refers to a structure, surface, feature, module, component, apparatus, and/or system that facilitates, enables, guides, promotes, precision in the alignment of two objects by way of registration. In one aspect a registration key can include a surface and one or more recesses and/or features of that surface that are configured to fit within corresponding recesses, projections, and/or other features of another structure such as another surface. In one aspect a registration key can include a surface and one or more projections and/or features of, extending from, or connected to that surface that are configured to fit within corresponding recesses, projections, and/or other features of another structure such as another surface. In certain aspects, the features of the registration key may be configured to fit within, or in contact, or in close contact with those of the another structure. In one embodiment, when the two structures align the registration key has served its purpose.

"Anatomical structure" or "Anatomy" refers to any part or portion of a part of a body of a person, animal, or other patient. Examples of anatomical structures, include but are not limited to, a bone, bones, soft tissue, a joint, joints, a tissue surface, a protrusion, a recess, an opening, skin, hard tissue, teeth, mouth, eyes, hair, nails, fingers, toes, legs, arms, torso, vertebrae, ligaments, tendons, organs, or the like.

"Anatomical reference" refers to any reference(s) that is, or is on, or is in, or is otherwise associated, with an anatomical structure. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, a hole, a post, a plurality of holes, a plurality of posts, a fastener, a suture, a clamp, an instrument, an implant, or the like.

As used herein, a "condition" refers to a state of something with regard to its appearance, quality, or working order. In certain aspects, a condition may refer to a patient's state of health or physical fitness or the state of health or physical fitness of an organ or anatomical part of a patient. In certain embodiments, a condition may refer to an illness, pain, discomfort, defect, disease, or deformity of a patient or of an organ or anatomical part of a patient. (Search "condition" on wordhippo.com. WordHippo, 2021. Web. Accessed 8 Dec. 2021. Modified.)

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" or "cutter guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "navigation guide" that guides a user in navigating a course or process or procedure such as a surgical procedure, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide."

Those of skill in the art will appreciate that a resection feature may take a variety of forms and may include a single feature or one or more features that together form the resection feature. In certain embodiments, the resection feature may take the form of one or more slots or cut channels. Alternatively, or in addition, a resection feature may be referenced using other names including, but not limited to, channel, cut channels, and the like.

"Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure.

"Cross section" or "cross-section" refers to the non-empty intersection of a body in three-dimensional space with a plane, or the analog in higher-dimensional spaces. (Search "cross section" on Wikipedia.com Mar. 7, 2022. Modified. Accessed Sep. 21, 2022.)

"Cut channel" refers to a channel, slot, hole, or opening, configured to facilitate making a cut. In certain embodiments, a cut channel is one example of a resection feature, resection member, and/or resection guide. "Rotation slot" refers to a channel, slot, hole, or opening, configured to facilitate rotating one structure in relation to another structure.

As used herein, "slot" refers to a narrow opening or groove. (search "slot" on Merriam-Webster.com. Merriam-Webster, 2021. Web. 4 Aug. 2021. Modified.)

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Resection interface" refers to an interface between a resected portion of tissue and another object, structure, or thing. Often a resection interface is an interface or boundary between one resected portion of an anatomical structure and another resected portion of another anatomical structure. The two anatomical structures can be portions, parts, or fragments of one anatomical structure or two different anatomical structures. A resection interface can be embodied in a variety of shapes and/or configurations, including a point, a line, a plane, a contour, a boundary, or the like. In one embodiment, a resection interface is an interface between two or more cut planes or two or more cut surfaces or two or more cut faces.

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Cortex" refers to an area of bone that extends from an external surface of the bone towards a center part of the bone. The cortex is typically comprised of cortical bone.

"Transosseous placement feature" refers to a placement feature that extends through one or more bones and that enables, or facilitates, placement of another device, apparatus, or instrument.

"Patient-specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features.

"Prescription" or "Prescribed" refers to a written order, as by a physician or nurse practitioner, for the administration of a medicine, preparation of an implant, preparation of an instrument, or other intervention. Prescription can also refer to the prescribed medicine or intervention. (Search "prescription" on wordhippo.com. WordHippo, 2023. Web. Accessed 3 May 2023. Modified.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two-dimensional structure that joins two adjacent structures or surfaces. Furthermore, an edge may be at a perimeter of an object or within a perimeter or boundary of an object.

"Bone fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search "joint" on Wikipedia.com Dec. 19, 2021. CC-BY-SA 3.0 Modified. Accessed Jan. 20, 2022.)

"Articular surface" refers to a surface of a structure that is coupled to, and may cooperate with, other structures of a joint of a human or animal to enable movement of structures of the joint.

"Tarso-metatarsal joint" or "TMT joint" refers to a joint of a patient between a metatarsal bone and one or more cuneiform/tarsal/cuboid bones. The TMT joint may also be referred to as a "Lis Franc" or "Lisfranc" joint after a French surgeon Lisfranc.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface (s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

As used herein, a "pivot axis" refers to an axis about which a structure pivots or rotates.

"Longitudinal axis" or "Long axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

"Mechanical axis" refers to an axis of a long bone such as a femur or tibia. The mechanical axis of a long bone is a straight line connecting the joint center points of the proximal and distal joint regions, whether in the frontal or sagittal plane. A mechanical axis can be useful in defining how the mechanical (weight, gait, flexion, extension, etc.) forces impact the morphology of the bone structure. A mechanical axis and anatomical axis can both help in the surgical planning in relation to deformed bones. (Search "axes of the long bones" on appropedia.com; Amit Dinanath Maurya, OpenSurgiSim (2021-2023). "Axes of the long bones—Mechanical and Anatomical". SELF. Modified. Accessed Jun. 28, 2023.)

"Pivot arm" refers to a structure that extends from another structure. Often, a pivot am) has similar size, shape, dimensions, and/or orientation as an am) of a person or animal. A pivot arm is a structure about which the structure connected to the pivot am) pivots or rotates. In certain embodiments, an axis that runs through the center of a pivot am) is also a pivot axis and can be a fulcrum where the pivot am) is part of a lever.

As used herein, a "drive", "drive feature", or "drive recess" refers to an apparatus, instrument, structure, member, device, component, system, or assembly structured, organized, configured, designed, arranged, or engineered to receive a torque and transfer that torque to a structure connected or coupled to the drive. At a minimum, a drive is a set of shaped cavities and/or protrusions on a structure that allows torque to be applied to the structure. Often, a drive includes a mating tool, known as a driver. For example, cavities and/or protrusions on a head of a screw are one kind of drive and an example of a corresponding mating tool is a screwdriver, that is used to turn the screw, the drive. Examples of a drive include but are not limited to screw drives such as slotted drives, cruciform drives, square drives, multiple square drives, internal polygon, internal hex drives, penta lobular sockets, hex lobular sockets, combination drives, external drives, tamper-resistant drives, and the like. (Search 'list of screw drives' on Wikipedia.com Mar. 12, 2021. Modified. Accessed Mar. 19, 2021.)

"Thread" or "threads" refers to a helical structure used to convert between rotational and linear movement or force. A thread is a ridge wrapped around a cylinder or cone in the form of a helix, with the ridge wrapped around the cylinder being called a straight thread and the ridge wrapped around the cone called a tapered thread. Straight threads or tapered threads are examples of external threads, also referred to as male threads. Threads that a correspond to male threads are referred to as female threads and are formed within the inside wall of a matching hole, passage, or opening of a nut or substrate or other structure. A thread used with a fastener may be referred to as a screw thread and can be a feature of a simple machine and also as a threaded fastener. The mechanical advantage of a threaded fastener depends on its lead, which is the linear distance the threaded fastener travels in one revolution. (Search 'screw thread' on Wikipedia.com Jul. 17, 2022. Modified. Accessed Aug. 1, 2022.)

"Cutting tool" refers to any tool that can be used to cut or resect another object. In particular, a cutting tool can refer to a manual or power tool for cutting or resecting tissue of a patient. Examples of cutting tools include, but are not limited to, a burr, rotary cutting tools such as a burr, router bit, drill bit, an oscillating saw, a reciprocating saw, a grater saw, a drill, a drill bit, a mill bit, a router bit, a side-cutting burr, or the like.

As used herein, a "shaft" refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

"Head" refers to a device, apparatus, member, component, system, assembly, module, subsystem, circuit, or structure, organized, configured, designed, arranged, or engineered to have a prominent role in a particular feature, function, operation, process, method, and/or procedure for a device, apparatus, member, component, system, assembly, module, subsystem, circuit, or structure the includes, is coupled to, or interfaces with the head. In certain embodiments, the head may sit at the top or in another prominent position when interfacing with and/or coupled to a device, apparatus, member, component, system, assembly, module, subsystem, circuit, or structure.

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cut surface" or "cut face" refers to a surface of an object that is created or formed by the removal of one or more parts of the object that includes the original surface. Cut surfaces or cut faces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface or cut face can include manual, mechanical, motorized, hydraulic, automated, robotic, and the like.

The present disclosure discloses surgical systems and methods by which a bone condition, that can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific instruments may be used for various other procedures on the foot, or on other bones of the musculoskeletal system. For example, patient-specific instruments and/or other instruments may be used for various procedures including resection and translation of a head of a long bone, determining where to perform an osteotomy on one or more joints or part of one or more bones, determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally, or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan and generate one or more instruments that are matched specifically to the size and/or shape of the patient's bone(s). In some embodiments, such instrumentation may include a targeting guide, trajectory guide, drill guide, resection guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, resection guide, dissection guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument (s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, an advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g., one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate predrilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

FIG. 1B is a flowchart diagram depicting a method 120 for correcting or remediating a bone condition, according to one embodiment. The method 120 may be used to prepare for an orthopedic procedure which corrects or remediates a bone, muscle, deformity, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally, or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

Figures 2A, 2B:
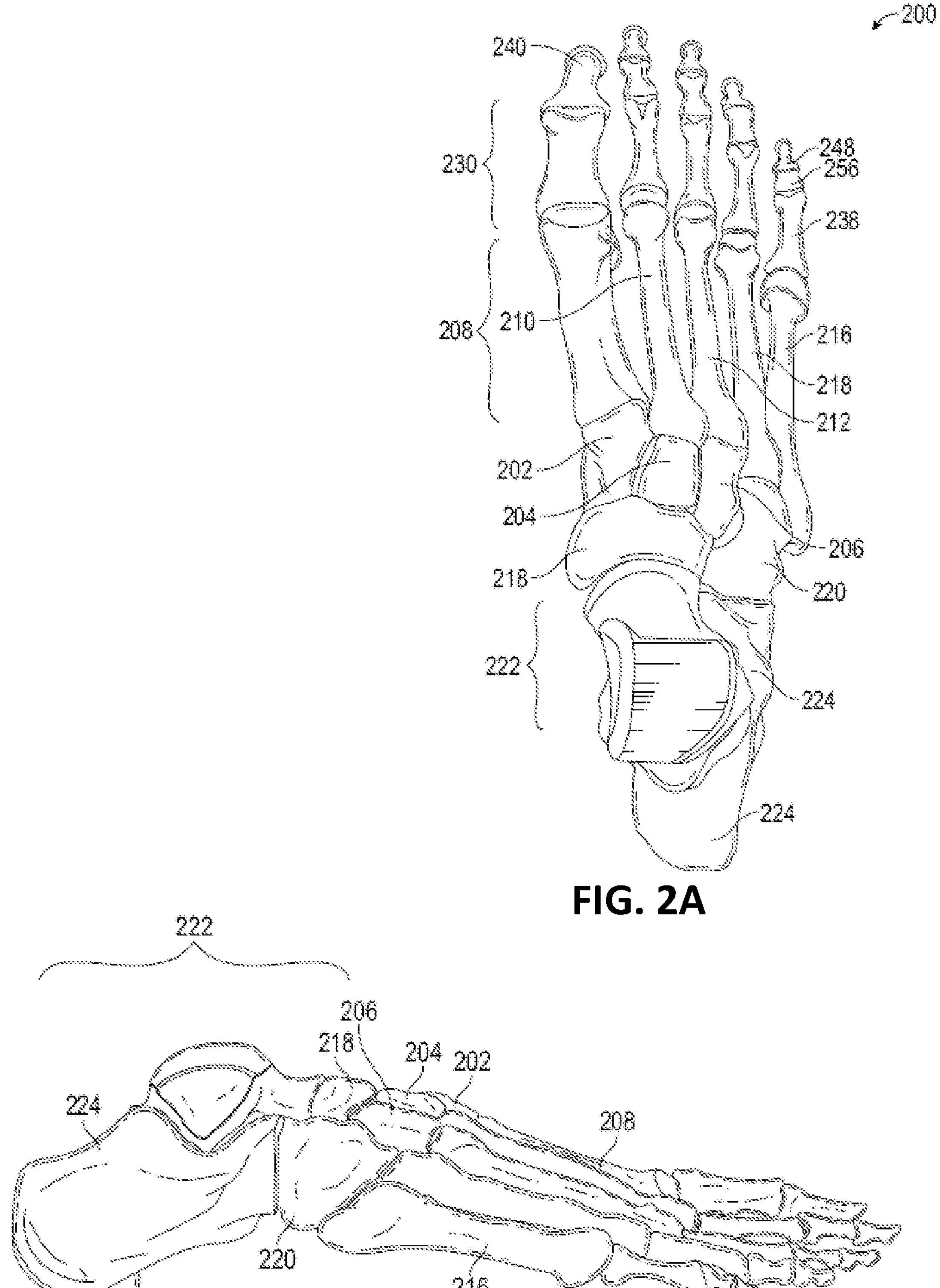
FIG. 2A is a dorsal perspective view of bones of a foot.
FIG. 2B is a lateral perspective view of bones of a foot.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

FIG. 2B is a perspective lateral view of a foot 200, with bones of the foot labeled.

Figure 2C:
FIG. 2C is a medial perspective view of bones of a foot.
Figure 2C:
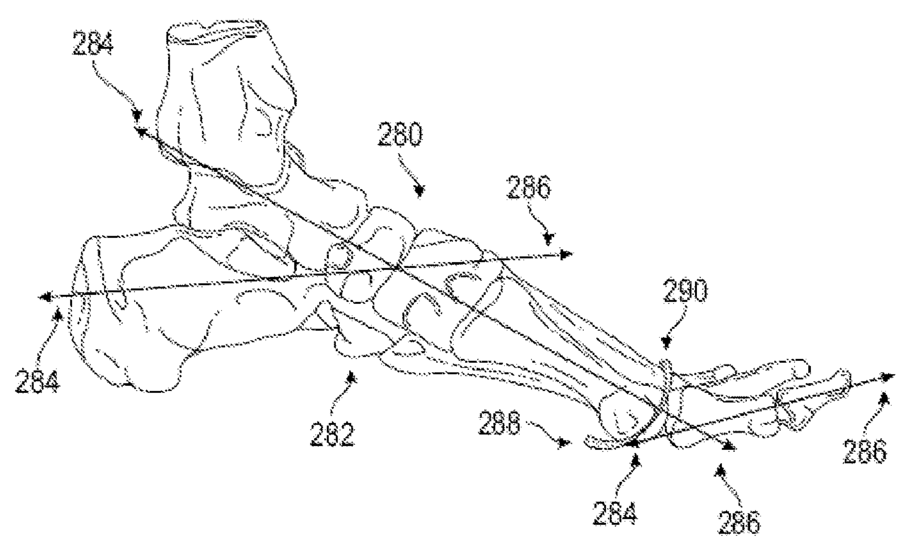
Figure 2D:
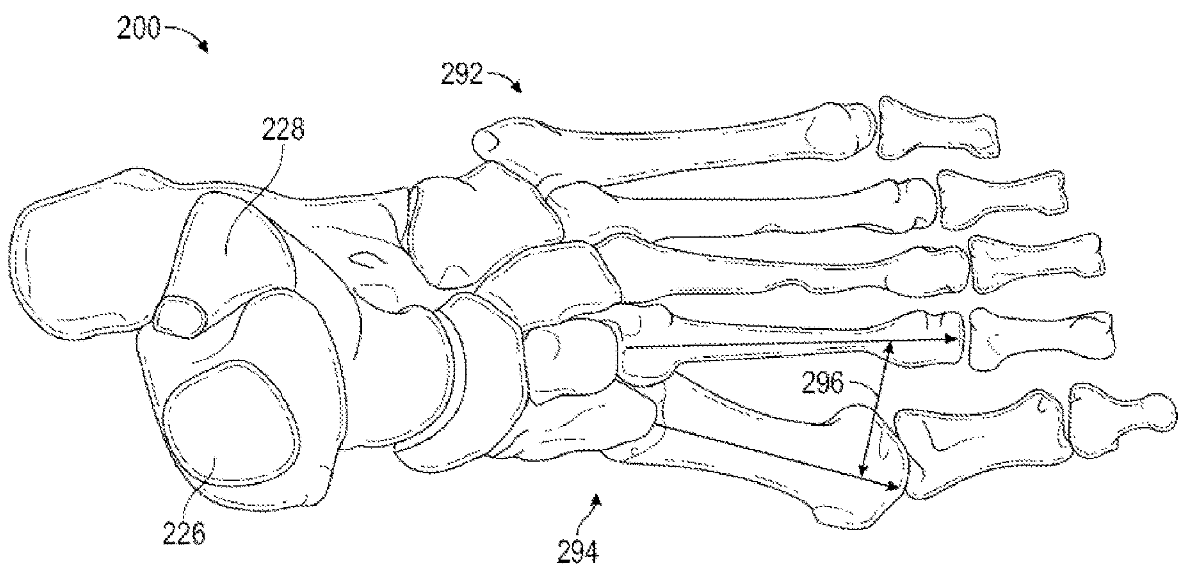
FIG. 2D is a dorsal perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion 290 means movement toward the dorsal side 280 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
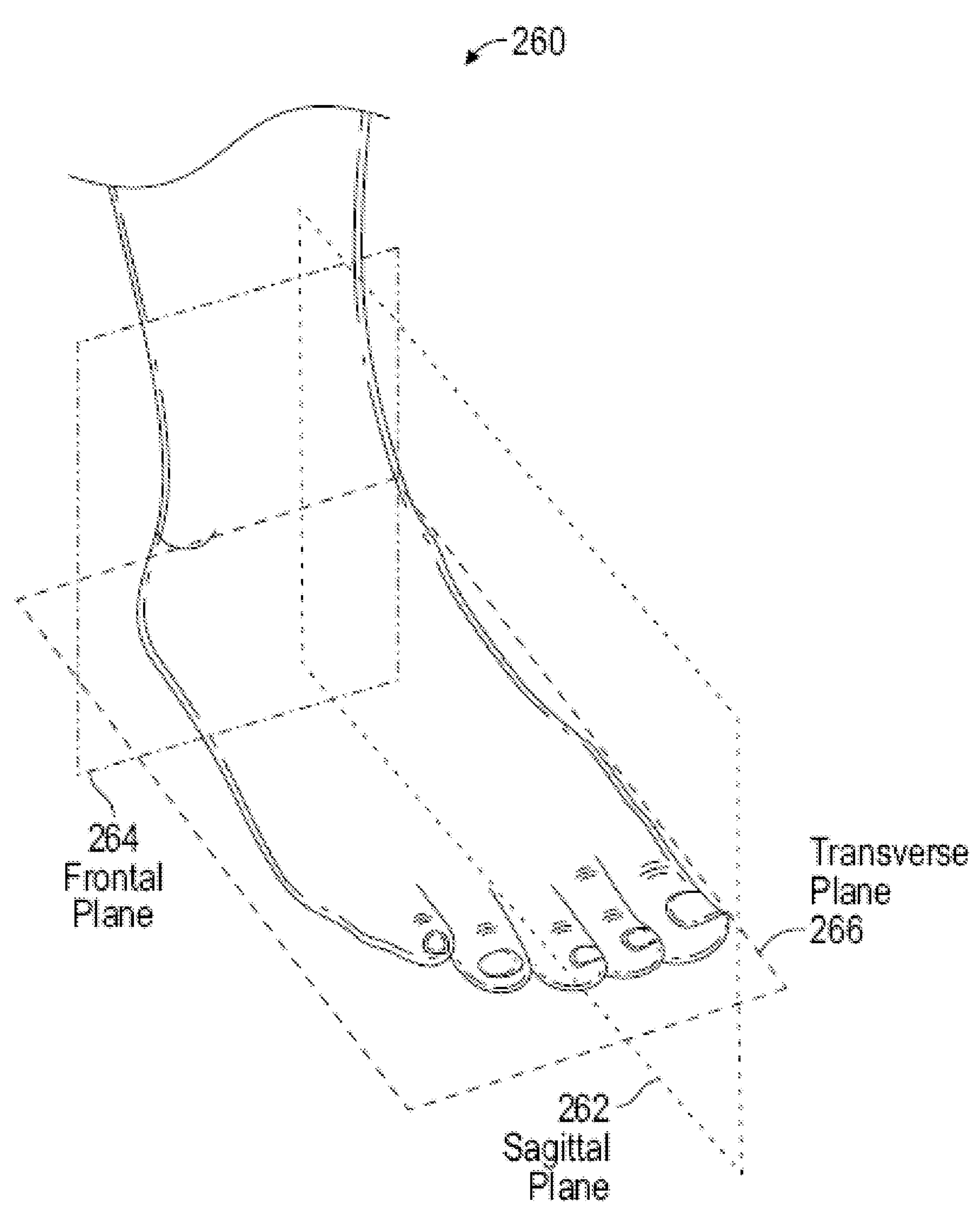
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
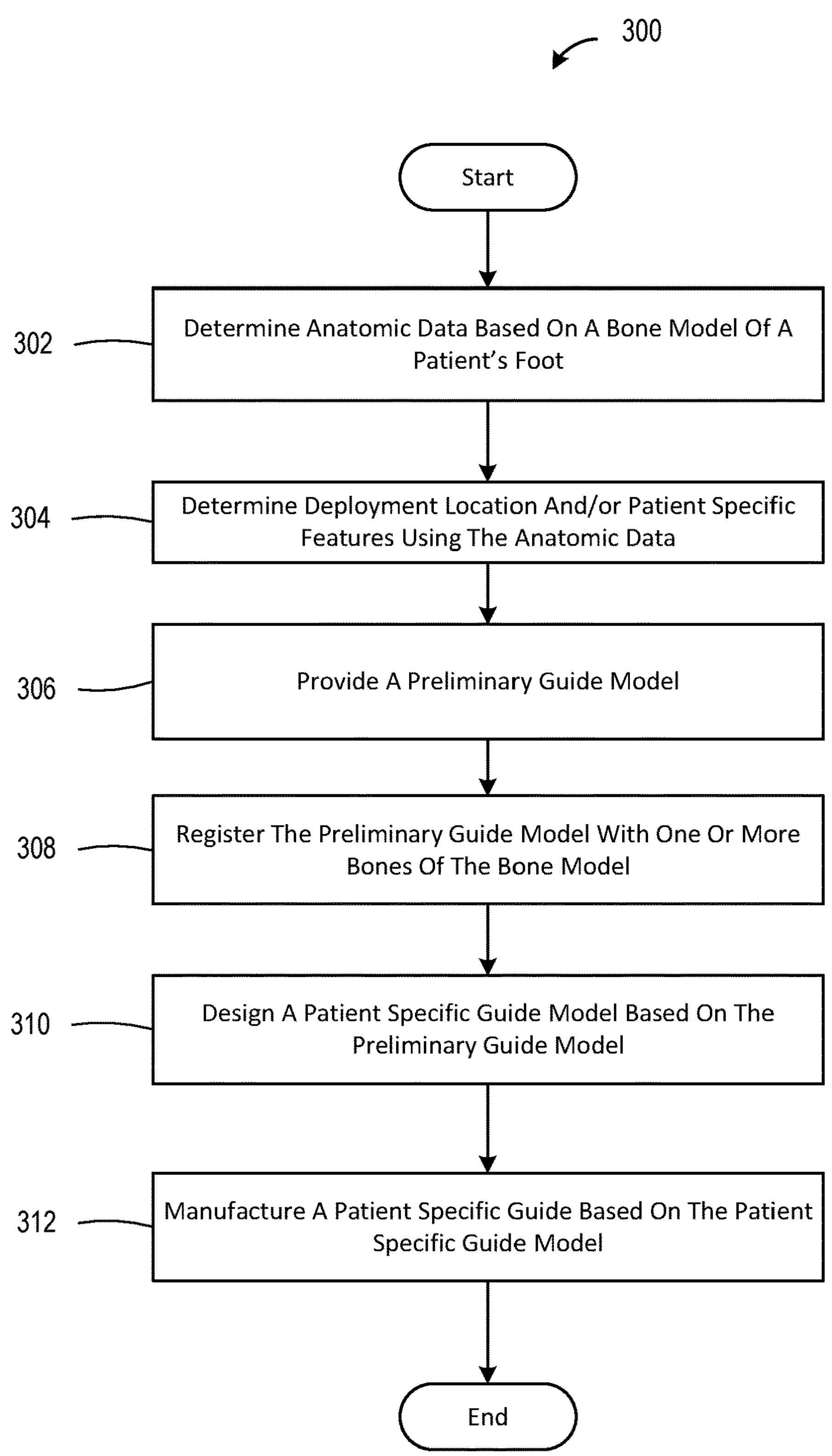
FIG. 3 is a flowchart diagram depicting a method for generating one or more patient-specific instruments configured to address a bone condition, according to one embodiment.

FIG. 3 illustrates a flowchart diagram depicting a method 300 for generating one or more patient-specific instruments configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 a recommended location and/or a trajectory angle and/or patient-specific features for a procedure using the anatomic data. "Recommended location" refers to a location for deployment of guide or instrument on, in, between, or within one or more body parts (e.g., bones) of a patient. "Trajectory angle" refers to a recommended angle for deployment of an instrument, graft, body part, or resection feature angle relative to a bone of a patient for a procedure. In certain embodiments, determining the recommended location may employ advanced computer analysis system, expert systems, machine learning, and/or automated/artificial intelligence. In another embodiment, the method 300 may include determining one or more alternative locations and/or trajectory angles for a surgical procedure.

Next, the method 300 may proceed and a preliminary guide model is provided 306 from a repository of template instrument models. A preliminary guide model is a model of a preliminary guide.

As used herein, "preliminary guide" refers to a guide configured, designed, and/or engineered to serve as a template, prototype, archetype, or starting point for creating, generating, or fabricating a patient-specific guide. In one aspect, the preliminary guide may be used, as-is, without any further changes, modifications, or adjustments and thus become a patient-specific guide. In another aspect, the preliminary guide may be modified, adjusted, or configured to more specifically address the goals, objectives, or needs of a patient or a surgeon and by way of the modifications become a patient-specific guide. The patient-specific guide can be used by a user, such as a surgeon, to guide steps in a surgical procedure, such as an osteotomy and/or a tendon transfer procedure. Accordingly, a preliminary guide model can be used to generate a patient-specific guide. The patient-specific guide model may be used in a surgical procedure to facilitate one or more steps of the procedure, and may be used to generate a patient-specific guide that can be used in a surgical procedure for the patient.

In certain embodiments, the preliminary guide model may be generated based on anatomic data and/or a bone model or a combination of these, and no model or predesigned structure, template, or prototype. Alternatively, or in addition, the preliminary guide model may be, or may originate from, a template guide model selected from a set of template guide models. Each model in the set of template guide models may be configured to fit for an average patient's foot. The template guide model may subsequently be modified or revised by an automated process or manual process to generate the preliminary guide model used in this disclosure.

As used herein, "template guide" refers to a guide configured, designed, and/or engineered to serve as a template for creating, generating, or fabricating a patient-specific guide. In one aspect, the template guide may be used, as-is, without any further changes, modifications, or adjustments and thus become a patient-specific guide. In another aspect, the template guide may be modified, adjusted, or configured to more specifically address the goals, objectives, or needs of a patient or a surgeon and by way of the modifications become a patient-specific guide. The patient-specific guide can be used by a user, such as a surgeon, to guide making one or more resections of a structure, such as a bone for a procedure. Accordingly, a template guide model can be used to generate a patient-specific guide model. The patient-specific guide model may be used in a surgical procedure to address, correct, or mitigate effects of the identified deformity and may be used to generate a patient-specific guide that can be used in a surgical procedure for the patient.

Next, the method 300 may register 308 the preliminary guide model with one or more bones of the bone model. This step 308 facilitates customization and modification of the preliminary guide model to generate a patient-specific guide model from which a patient-specific guide can be generated. The registration step 308 may combine two models and/or patient imaging data and positions both models for use in one system and/or in one model.

Next, the method 300 may design 310 a patient-specific guide model based on the preliminary guide model. The design step 310 may be completely automated or may optionally permit a user to make changes to a preliminary guide model or partially completed patient-specific guide model before the patient-specific guide model is complete. A preliminary guide model and patient-specific guide model are two examples of an instrument model. As used herein, "instrument model" refers to a model, either physical or digital, that represents an instrument, tool, apparatus, or device. Examples of an instrument model can include a cutting guide model, a resection guide model, a dissection guide model, an alignment guide model, a reduction guide model, a patient-specific tendon trajectory guide model, and the like. In one embodiment, a patient-specific guide and a patient-specific guide model may be unique to a particular patient and that patient's anatomy and/or condition.

The method 300 may conclude by a step 312 in which patient-specific guide may be manufactured based on the patient-specific guide model. Various manufacturing tools, devices, systems, and/or techniques can be used to manufacture the patient-specific guide.

Figure 4:
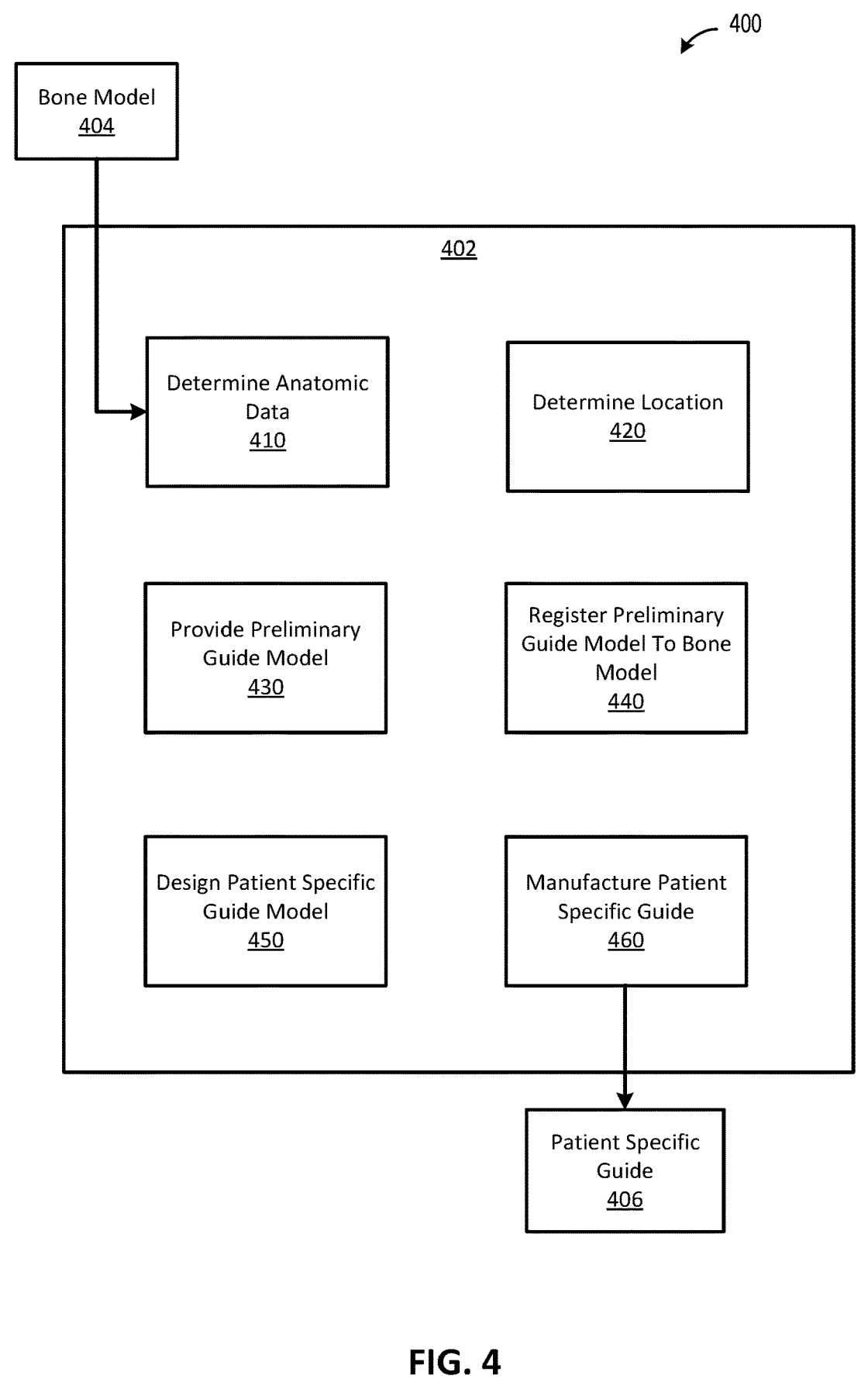

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific guide 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one or more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one or more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a "soft tissue envelope" (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, and bone density scans can be combined to effectively create an anatomic map that determines the structural integrity of the underlying bone.

Identifying the structural integrity of the underlying bone can help in determining where bone resections can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument, graft, and/or soft tissue based on the anatomic data 412 and/or the bone model 404. In one embodiment, the location module 420 may compare the anatomic data 412 to a general model that is representative of most patient's anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary guide model 438. The preliminary guide model 438 may serve as a model for an instrument to be used in a surgical procedure. The provision module 430 may use a variety of methods to provide the preliminary guide model. In one embodiment, the provision module 430 may generate a preliminary guide model. In the same, or an alternative embodiment, the provision module 430 may select a template guide model for a surgical procedure configured to enable locating the position and/or providing the trajectory provided by the location module 420. In one embodiment, the provision module 430 may select a template guide model from a set of template guide models (e.g., a library, set, or repository of template guide models).

The registration module 440 registers the preliminary guide model with one or more bones or other anatomical structures of the bone model 404. As explained above, registration is a process of combining medical imaging data, patient imaging data, and/or one or more models such that the preliminary guide model can be used with the bone model 404.

The design module 450 designs a patient-specific guide (or patient-specific guide model) based on the preliminary guide model. The design operation of the design module 450 may be completely automated, partially automated, or completely manual. A user may control how automated or manual the designing of the patient-specific guide (or patient-specific guide model) is.

The manufacturing module 460 may manufacture a patient-specific guide 406 using the preliminary guide model. The manufacturing module 460 may use a patient-specific guide model generated from the preliminary guide model. The manufacturing module 460 may provide the patient-specific guide model to one or more manufacturing tools and/or fabrication tool. The patient-specific guide model may be sent to the tools in any format such as an STL file or any other CAD modeling or CAM file or method for data exchange. In one embodiment, a user can adjust default parameters for the patient-specific guide such as types and/or thicknesses of materials, dimensions, and the like before the manufacturing module 460 provides the patient-specific guide model to a manufacturing tool.

Effective connection of the guide to one or more bones can ensure that surgical steps are performed in desired locations and/or with desired orientations and mitigate undesired surgical outcomes.

Figure 5:
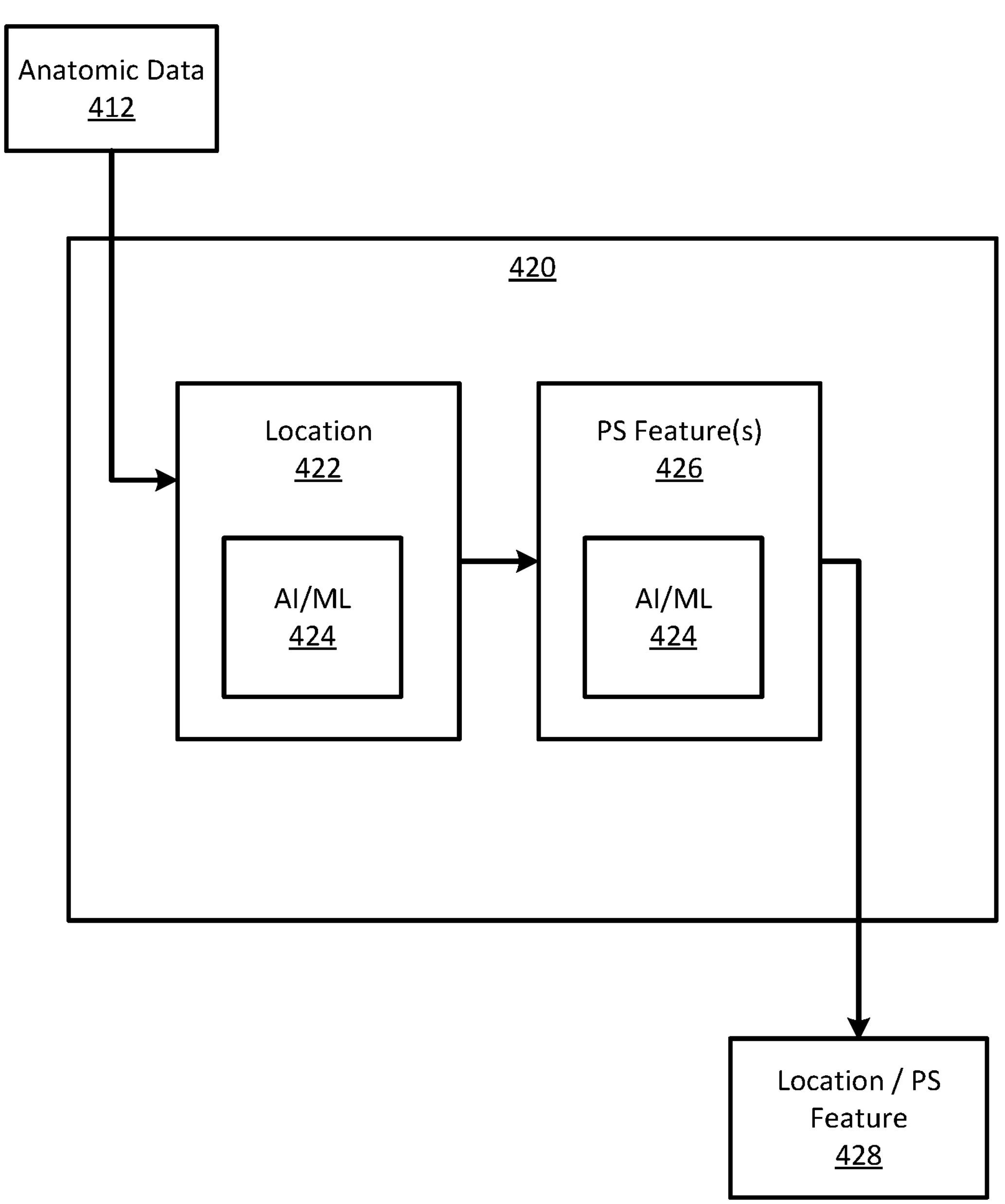
FIG. 5 illustrates an exemplary apparatus configured to facilitate generation of one or more patient-specific instruments, according to one embodiment.

FIG. 5 illustrates an exemplary location module 420 configured to determine a location and/or trajectory for an instrument (patient-specific or patient-matched), according to one embodiment. The location module 420 may factor in one or more landmarks on one or more surfaces of one or more bones of a patient of the bone model 404. The location module 420 may be completely automated, partially automated, or completely manual. A user may control how automated or manual the determination of the location is. The user may provide instructions to the location module 420 to facilitate automatic or partially automated determination of one or more locations.

The location module 420 may include a location module 422. The location module 422 may be configured for automated determination of a location for use of an instrument. For example, in one embodiment, the location module 422 includes an artificial intelligence or machine learning module 424. The artificial intelligence or machine learning module 424 is configured to implement one or more of a variety of artificial intelligence modules that may be trained for identifying bones in the bone model 404, determining surfaces and/or sides of one or more bones, determining landmarks (both natural and/or abnormalities), determining axes of a bone, such as a longitudinal axis and/or a horizontal axis of a bone based on anatomic data 412 and/or a bone model 404. In another embodiment, the location module 420 may receive patient imaging data, a bone model, a CAD model or the like and use these inputs to determine a location and/or trajectory in relation to one or more bones of a patient.

In one embodiment, the artificial intelligence or machine learning module 424 may be trained using a large data set of anatomic data 412 for healthy bones and a large data set of anatomic data 412 for bones with abnormalities and/or landmarks in which the abnormalities and/or landmarks have been previously identified and labeled in the dataset. The artificial intelligence or machine learning module 424 may implement, or use, a neural network configured according to the training such that as the artificial intelligence or machine learning module 424 accepts the anatomic data 412 for a particular patient, the artificial intelligence or machine learning module 424 is able to determine what one or more locations (e.g., a recommended location and one or more alternative locations for the guide.

The location module 422 may interact with a patient specific feature module 426. The patient specific feature module 426 may take one or more locations provided by the location module 422 and the bone model 404 and/or anatomic data 412 and determine suitable patient specific features. In certain embodiments, the patient specific features provided by the patient specific feature module 426 may include a number of resection features, an angle or trajectory for one or more resection features, a number, size, and/or position of bone attachment features, a number, size, or position of alignment guides or a combination of these. In certain embodiments, the patient specific feature module 426 may focus on resection features.

As with the location module 420, the patient specific feature module 426 may be completely automated, partially automated, or completely manual. A user may control how automated or manual the determination of the trajectory is. The user may provide instructions to the patient specific feature module 426 to facilitate automatic or partially automated determination of one or more trajectories. In one embodiment, the location module 422 includes an artificial intelligence or machine learning module 424 that facilitates determining one or more trajectories.

The location module 420 outputs a location/patient specific feature 428 for an orthopedic surgical procedure.

Figure 6:
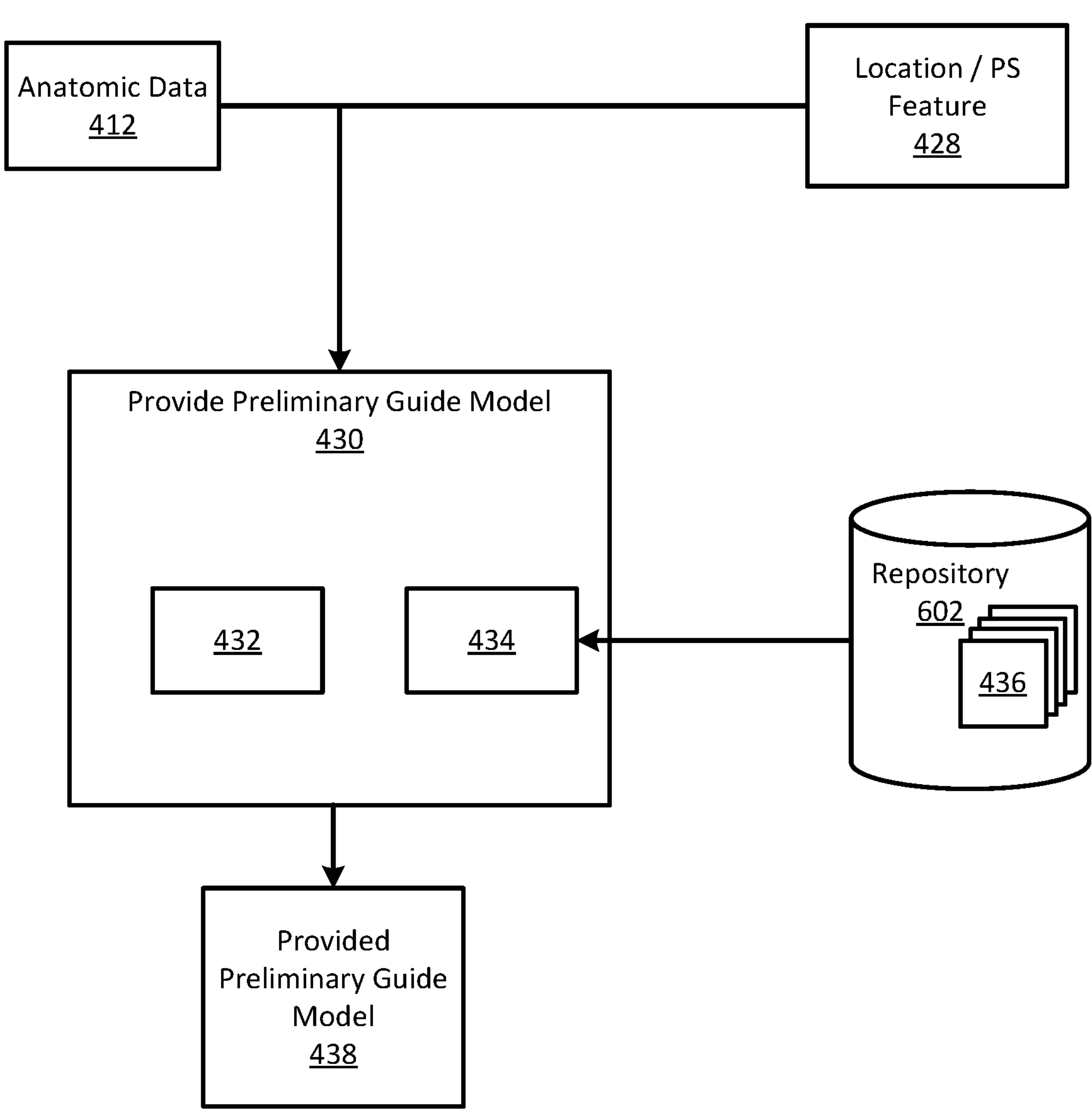
FIG. 6 illustrates an exemplary provision module configured to provide a preliminary guide model, according to one embodiment.

FIG. 6 illustrates an exemplary provision module 430 configured to provide a preliminary guide model, according to one embodiment. The provision module 430 may accept anatomic data 412 and a location/patient specific feature 428. In the illustrated embodiment, the provision module 430 may generate a preliminary guide model 438 (e.g., generate from 'scratch') or the provision module 430 may select a template guide model 436 automatically from a set of template guide models 436 stored in a repository 602. The provision module 430 may incorporate a variety of parameters in order to provision, generate, determine, or select a template guide model 436. For example, in addition to the anatomic data 412, the provision module 430 may include patient imaging data, deformity parameters for a variety of angular deformities (in all 3 planes) of the midfoot or hind foot and ankle where a surgical procedure could be used, patient preferences, and/or surgeon input parameters.

In one embodiment, the provision module 430 may include a generator 432 and/or a selection module 434. In one embodiment, the generator 432 is configured to generate a preliminary guide model 438. In certain embodiments, the generator 432 may generate or create the preliminary guide model based on anatomic data and/or a bone model or a combination of these and no other inputs. (e.g. no model or predesigned structure, template, or prototype). Alternatively, or in addition, the generator 432 may generate or create the preliminary guide model using a standard set of features or components that can be combined to form the preliminary guide model. The generated preliminary guide model may subsequently be modified or revised by an automated process, and/or manual process, to generate the preliminary guide model used in this disclosure.

The selection module 434 may be configured to select a template guide model 436 for an osteotomy procedure configured to correct the deformity identified by the location module 420. In one embodiment, the provision module 430 may select a template guide model 436 from a set of template guide models 436 (e.g., a library, set, or repository of template guide models 436). In one embodiment, the template guide model 436 may include digital models. In another embodiment, the template guide model 436 may include physical models. In such an embodiment, the repository 602 may be a warehouse or other inventory repository. Where the template guide model 436 are physical models, the systems, modules, and methods of this disclosure can be used and the physical model may be milled or machined (e.g., a CNC machine) to form a patient-specific guide that conforms to the bone surfaces of the patient.

Selection of a suitable template guide model 436 may be completely automated and/or may be partially automated and/or may depend on confirmation from a user before a generated preliminary guide model or a proposed template guide model 436 becomes the preliminary guide model 438. In another embodiment, the selection module 434 may facilitate a manual selection by a user of a template guide model 436 that would become the preliminary guide model 438. The selection module 434 may use the anatomic data 412 or the bone model 404 or a combination of these to select a suitable template guide model that would become the preliminary guide model 438.

In another embodiment, the generator 432 may facilitate revisions or edits by a user of a generated guide model that will become the preliminary guide model 438. The selection module 434 may use the anatomic data 412 or the bone model 404 or a combination of these to select a suitable template guide model that would become the preliminary guide model 438.

The repository 602 may include any number of, and/or a variety of template guide models 436. The template guide models 436 may be distinguished based on a gender or age of the patient, which joint of a midfoot, hind foot, or ankle will be cut, which material will be used for the template guide, and the like. The template guide model 436 may differ from each other in what degree of deformity correction the template guide model 436 is designed to provide. In addition, the template guide models 436 may be distinguished based on how one or more features of the template guide model 436 are positioned, arranged, and/or configured relative to each other. For example, in certain template guide models 436, the number, position, and/or configuration of alignment features and/or bone attachment features (e.g., holes) may vary based on needs or preferences of patients, the nature of the deformity, and/or surgeon preferences.

In certain embodiments, the template guide models 436 may vary in how the channels (e.g., resection features) for the cuts are positioned, angled, and oriented relative to each other and/or to a longitudinal axis of respective bones at a joint for use with the template guide model 436. For example, in one template guide model 436 a cut channel for a resection of a metatarsal bone may be perpendicular to a longitudinal axis of the metatarsal bone and the cut channel may be angled relative to a longitudinal axis of the cuneiform or cuboid bone such that once the two bones are brought together the deformity is corrected. Alternatively, in another template guide model 436 the slot for a resection of a metatarsal bone may be angled relative to a longitudinal axis of the metatarsal bone and the cut channel may be perpendicular to a longitudinal axis of the cuneiform or cuboid bone such that once the two bones are brought together the deformity is corrected.

The selection module 434 may be configured to automatically select a template guide model 436 and/or provide an automatic template guide model 436 recommendation that can be changed by a user, such as a surgeon. For example, in one embodiment, the provision module 430 and/or selection module 434 includes an artificial intelligence or machine learning module. The artificial intelligence or machine learning module is configured to implement one or more of a variety of artificial intelligence modules that may be trained for selecting a template guide model 436 based on anatomic data 412 and/or other input parameters. In one embodiment, the artificial intelligence or machine learning module may be trained using a large data set of anatomic data 412 for suitable template guide models 436 identified and labeled in the dataset by professionals for use to treat a particular deformity. The artificial intelligence or machine learning module may implement, or use, a neural network configured according to the training such that as the artificial intelligence or machine learning module is able to select a suitable template guide model 436. The template guide model 436 selected by the selection module 434 can become the preliminary guide model 438.

Figure 7:
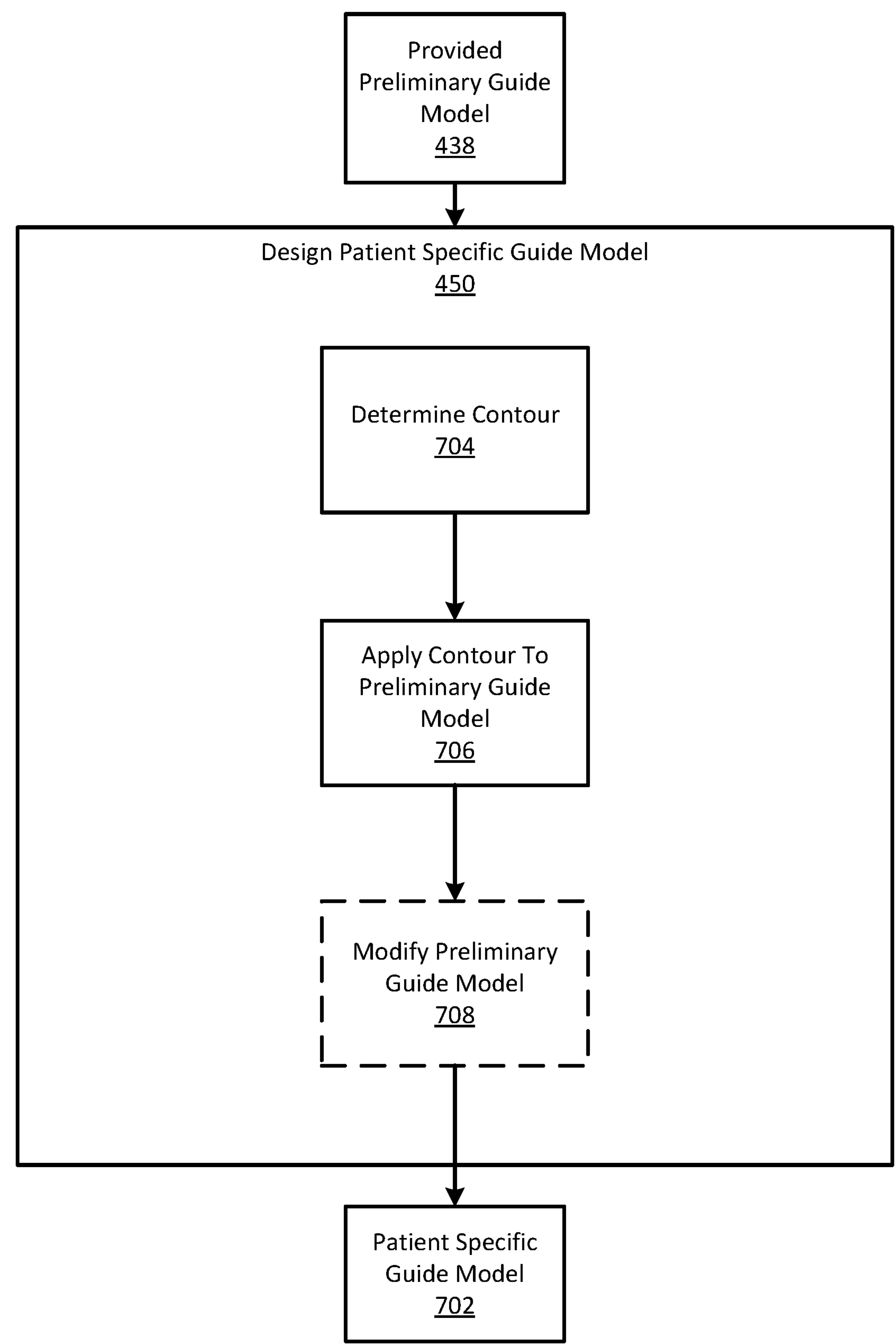
FIG. 7 illustrates an exemplary design module configured to design a patient-specific guide model, according to one embodiment.

FIG. 7 illustrates an exemplary design module 450 configured to design a patient-specific guide model, according to one embodiment. The design module 450 may accept a preliminary guide model 438 and generate a patient-specific guide model 702. In one embodiment, the design module 450 includes a contour module 704, an application module 706, and/or an optional modification module 708.

Referring now to FIG. 7, the design module 450 may modify the preliminary guide model 438 such that the bone-facing and/or bone-contacting surfaces of the preliminary guide model 438 match a contour of the surfaces and/or joint of one or more bones where a step of an orthopedic procedure will be performed using the preliminary guide model 438.

The contour module 704 may determine a contour of the bones that will contact the preliminary guide model 438. The contour module 704 may use a bone model 404 and/or anatomic data 412 to determine the contour. For example, the contour module 704 may determine the shape of a dorsal surface of a calcaneus 224.

The application module 706 may apply the contour to the provided preliminary guide model 438 to custom contour a bone engagement surface of the preliminary guide model 438 to match the shape, contour, and/or one or more landmarks of a bone, such as a dorsal surface of a calcaneus 224. Applying the contour to the preliminary guide model 438 may convert the preliminary guide model 438 to a patient-specific guide model 702.

Generation of the contours of bone engagement surface of the preliminary guide model 438 may be performed in various CAD programs. In some embodiments, the shapes of the corresponding surface dorsal surface of a calcaneus 224 may be obtained directly from the bone model 404, anatomic data 412, CAD models and/or CT scan data, and simply copied onto the preliminary guide model 438. Various operations may be used to copy surfaces from one object to another. Additionally, or alternatively, various Boolean operations, such as a Boolean subtraction operation, may be used to remove material from a model for the body of the preliminary guide model 438 with a shape that matches the dorsal surface of a calcaneus 224.

In certain embodiments, the design module 450 may include an optional module, such as a modification module 708. The modification module 708 may enable a user such as a technician or surgeon to make additional modifications to the design and configuration of the preliminary guide model 438. In one embodiment, the user can change any of the features, trajectories, fixation holes, handle engagement holes, angles, configurations, or parameters of the preliminary guide model 438. For example, a surgeon may be aware of other concerns or anatomic aspects of a patient, for example on an opposite foot or in connection with a hip or other orthopedic joint which motivate the surgeon to adjust an angle of one of more trajectories of the preliminary guide model 438.

Alternatively, or in addition, a user may use the modification module 708 to modify a predefined surgical procedure. The user may add, remove, or modify steps and the instrumentation used in the surgical procedure to create a patient-specific surgical procedure. In this manner, a user may configure features of a preliminary guide model 438 or modified preliminary guide model and/or surgical procedure specific to a patient-specific osteotomy procedure the surgeon is planning for the patient.

The user may review the preliminary guide model 438 and make adjustments or revisions or make no adjustments or revisions. The output of the modification module 708 and/or the application module 706 is a patient-specific guide model 702.

Figure 8:
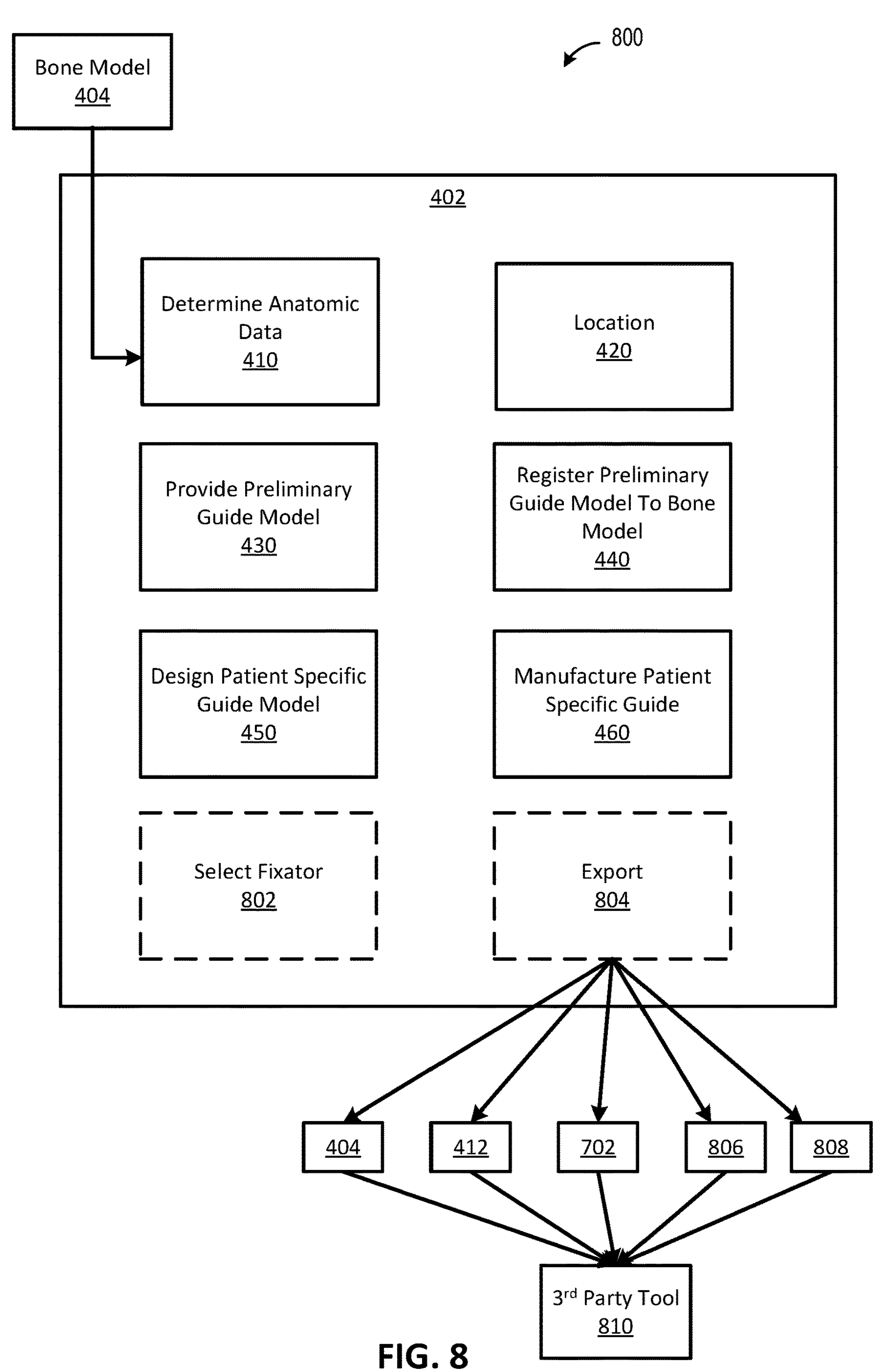
FIG. 8 illustrates an exemplary system configured to generate one or more patient-specific instruments configured to address a bone condition, according to one embodiment.

FIG. 8 illustrates an exemplary system 800 configured to generate one or more patient-specific instruments configured to correct a bone condition, according to one embodiment. The system 800 may include similar components or modules to those described in relation to FIG. 4. In addition, the system 800 may include a fixator selector 802 and/or an export module 804.

The fixator selector 802 enables a user to determine which fixator(s) to use for a surgical procedure planned for a patient. In one embodiment, the fixator selector 802 may recommend one or more fixators based on the bone model 404, the location, the trajectory, or input from a user or a history of prior surgical procedures performed. The fixator selector 802 may select a fixator model from a set of predefined fixator models or select a physical fixator from a set of fixators. The fixators may include a plate and associated accessories such as screws, anchors, and the like.

In one embodiment, the fixator selector 802 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that as the artificial intelligence or machine learning module is able to select or recommend suitable fixator(s).

The export module 804 is configured to enable exporting of a patient-specific guide model 702 for a variety of purposes including, but not limited to, fabrication/manufacture of a patient-specific guide 406 and/or fixator(s), generation of a preoperative plan, generation of a physical bone model matching the bone model 404, and the like. In one embodiment, the export module 804 is configured to export the bone model 404, anatomic data 412, a patient-specific guide model 702, a preoperative plan 806, a fixator model 808, or the like. In this manner the custom instrumentation and/or procedural steps for a surgical procedure can be used in other tools. The preoperative plan 806 may include a set of step-by-step instructions or recommendation for a surgeon or other staff in performing a surgical procedure such as an osteotomy. The preoperative plan 806 may include images and text instructions and may include identification of instrumentation to be used for different steps of the surgical procedure. The instrumentation may include the patient-specific guide 406 and/or one or more fixators. In one embodiment, the export module 804 may provide a fixator model which can be used to fabricate a fixator for the surgical procedure.

The exports (404, 412, 702, 806, and 808) may be inputs for a variety of 3rd party tools 810 including a manufacturing tool, a simulation tool, a virtual reality tool, an augmented reality tool, an operative procedure simulation tool, a robotic assistance tool, and the like. A surgeon can then use these tools when performing a surgical procedure or for rehearsals and preparation for the surgical procedure. For example, a physical model of the bones, patient-specific guide 406, and/or fixators can be fabricated, and these can be used for a rehearsal operative procedure. Alternatively, a surgeon can use the bone model 404, preliminary guide model 438, and/or a fixator model to perform a simulated surgical procedure using an operative procedure simulation tool.

Figure 9:
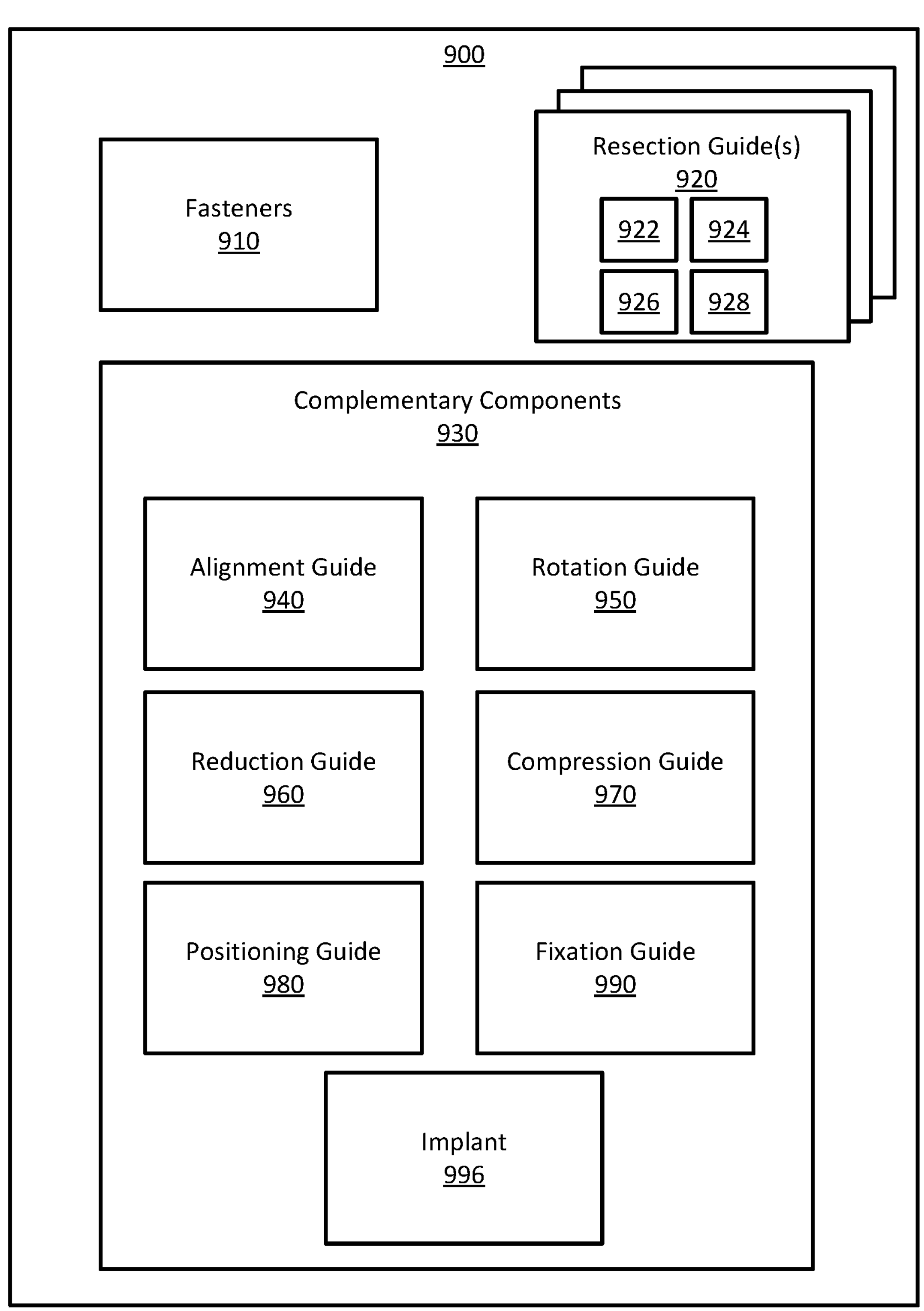
FIG. 9 illustrates an exemplary system, according to one embodiment.

FIG. 9 illustrates an exemplary system 900, according to one embodiment. The system 900 can include one or more fasteners 910, one or more resection guides 920, and one or more complementary components 930. While a system 900 can be used for a variety of procedures, one or more features, components, and/or aspects of the system 900 may be particularly suited for one or more osteotomies on one or more bones of a structure such as a patient's foot, ankle, wrist, hand, shoulder, or the like.

In certain embodiments, the one or more fasteners 910 can include one or more permanent fasteners and/or one or more temporary fasteners. Typically, the fasteners 910 may be used during a variety of different steps of a procedure. Temporary fasteners are often used because they can securely hold bone or parts/fragments of bones while steps of the procedure are conducted. A common temporary fastener that can be used with system 900 is a K-wire, also referred to as a pin or guide pin.

The one or more resection guides 920 assist a surgeon in performing different resection or dissection steps for an osteotomy or other procedure. In certain embodiments, a resection guide 920 includes one or more resection features 922 and one or more bone attachment features 924. The resection features 922 can take a variety of forms and/or embodiments. Similarly, the bone attachment features 924 can take a variety of forms and/or embodiments. The resection features 922 provide a guide for a surgeon using a cutting tool to resect a bone, one or more bones, or other tissues of a patient. In certain embodiments, the resection features 922 may guide a surgeon in performing a resection and/or a dissection. The bone attachment features 924 serve to secure the resection guide 920 to one or more bones and/or one or more other structures. Often, a bone attachment feature 924 can include a hole in the resection guide 920 together with a temporary fastener such as a K-wire or pin.

The bone attachment features 924 facilitate attachment of a resection guide 920 to one or more bones, or bone fragments, of a patient. The bone attachment features 924 may include any of a wide variety of fasteners including, but not limited to, holes, spikes, fastening devices, and/or the like. Effective connection of the resection guide 920 to one or more bones across a joint and/or to one or more bones can ensure that cut surfaces are formed in desired locations and orientations and mitigate removal of hard tissue and/or soft tissue in undesired locations and/or orientations.

In certain embodiments, a resection guide 920 may include one or more bone engagement surfaces 926 and/or one or more landmark registration features 928. In certain embodiments, a landmark registration feature 928 may extend from one or more sides of the resection guide 920 and engage with one or more landmarks of a bone or joint or anatomical structure of a patient. Registration of the landmark registration feature 928 to a landmark of a bone can serve to confirm that a surgeon has located a desired placement and/or orientation for a resection guide 920.

In certain embodiments, the bone engagement surfaces 926 are patient-specific: contoured to match a surface of: one or more bones the resection guide 920 contacts during the procedure or one or more joints proximal to the resection guide 920 during the procedure. Alternatively, or in addition, the bone engagement surface 926 may not be patient-specific, and may, or may not, contact a bone surface during use of the resection guide 920. In one embodiment, a skin contact surface may be used in addition to or in place of a bone engagement surface. Those of skill in the art appreciate that one or more sides of any of the members of the system 900 may include one or more bone engagement surfaces 926. Consequently, one or more sides of the fasteners 910, the resection guide(s) 920, the complementary components 930, and/or the implants 996 may include one or more bone engagement surfaces 926.

The complementary components 930 serve to assist a surgeon during one or more steps of a procedure. Those of skill in the art appreciate that a number of components can serve as complementary components 930. One or more of the features, functions, or aspects of the complementary components 930 can include patient-specific features.

Examples of complementary components 930 include, but are not limited to, an alignment guide 940, a rotation guide 950, a reduction guide 960, a compression guide 970, a positioning guide 980, a fixation guide 990, and/or one or more implants 996. In general, the complementary components 930 serve to assist a surgeon in performing the function included in the name of the complementary component 930. Thus, an alignment guide 940 can help a surgeon align bones, parts of bones, or other parts of a patient as part of a procedure. A rotation guide 950 can help a surgeon rotate one or more bones, parts of bones, or other parts of a patient as part of a procedure.

A reduction guide 960 can help a surgeon position and/or orient one or more bones, parts of bones, or other parts of a patient as part of a procedure in order to reduce the bone, bones, bone parts, or other parts and/or in order to position and/or orient the bone, bones, bone parts, or other parts to a desired position and/or orientation. A compression guide 970 can help a surgeon compress one or more bones, parts of bones, or other parts of a patient together or against an implant as part of a procedure. A positioning guide 980 can help a surgeon position one or more bones, parts of bones, or other parts of a patient as part of a procedure.

In certain embodiments, the positioning guide 980 may be designed and fabricated to be patient-specific. The patient-specific aspects can include a patient-specific bone engagement surface, a predefined angle for reorienting one or more bone or bone parts within one or more planes, a predefined position for bone attachment features 924 or fasteners 910, or the like. Alternatively, or in addition, the positioning guide 980 may be selected from a kit, collection, or repository of a number of positioning guides 980: each having a different configuration for one or more aspects/attributes of the positioning guide 980. For example, each member of the repository/kit may include a different positioning angle (repositioning or correction angle), the angles may differ by 2 degrees for example. In such an embodiment, each positioning guide 980 may not be patient-specific to a particular patient but may provide the desired amount of positioning to meet the goals of the surgeon. In certain embodiments, a preoperative plan generated based on the present disclosure may include a recommendation for the positioning guide 980 to be used, even if the recommended positioning guide 980 is not patient-specific to the particular patient.

A fixation guide 990 can help a surgeon in completing one or more temporary or permanent fixation steps for one or more bones, parts of bones, or other parts of a patient as part of a procedure. The fixation guide 990 may include and/or may use one or more components of a fastener or fixation system including implant hardware of the fastener or fixation system.

One example of a complementary components 930 may include a compressor/distractor. The compressor/distractor can be used to compress or distract bones or parts of bones involved in a procedure.

Advantageously, the system 900 can help a surgeon overcome one or more of the challenges in performing an osteotomy procedure, particularly on bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the fasteners 910, resection guide(s) 920, and/or complementary components 930 can be configured to assist in overcoming this challenge.

Advantageously, the system 900 can help a surgeon in positioning, placing, and/or orienting a resection guide accurately. Modern techniques may include preoperative planning, simulation, or even practice using computer models, 3D printed models, virtual reality systems, augmented reality systems or the like. However, simulations and models are still different from actually positioning a resection guide on a patient's bone, joint, or body part during the procedure. The system 900 can include a number of features, including patient-specific features, to assist the surgeon with the positioning. In one embodiment, the resection guide 920 can include one or more landmark registration features 928.

Advantageously, the system 900 can help a surgeon in securing guides of the osteotomy system 900, such as a resection guide, as well as how to readily remove the guide (e.g., resection guide) without disturbing a reduction, shifting, reorienting, or repositioning one or more bones or parts of bones while removing the guide. In certain embodiments, the system 900 is configured to permit removal of a guide while keeping temporary fasteners in place for use in subsequent steps of an osteotomy procedure. Alternatively, or in addition, the system 900 may facilitate positioning of temporary fasteners during one step of a wedge osteotomy procedure for use in a subsequent step of the wedge osteotomy procedure. Removal of a guide during an osteotomy procedure can be particularly challenging where translation and/or rotation of the bones involved in the osteotomy procedure is required for the success of the osteotomy procedure. Advantageously, the system 900 accommodates translation and/or rotation of the bones during the osteotomy procedure while facilitating a successful outcome for the osteotomy procedure.

Advantageously, the components of the system 900 can be specifically designed for a particular patient. Alternatively, or in addition, the components of the system 900 can be specifically designed for a class of patients. Each of the components of the system 900 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides an optimal osteotomy with minimal risk of undesirable resection. In one embodiment, the components of the system 900 can be configured such that an osteotomy is performed that enables a correction in more than one plane in relation to the parts of the body of the patient. For example, cut channels or resection features 922 in a resection guide 920 can be oriented and configured such that when the bones are fused/fixated the correction results from translation, rotation, and/or movement of bones or bone parts in two or more planes (e.g., sagittal and transverse) once the fragments or bones are reduced.

In certain embodiments, the exemplary system 900 may include a plurality of fasteners 910, resection guides 920, and/or complementary components 930. For example, a surgeon may plan to resect a plurality of osteotomies from the bone(s) in order to accomplish a desired correction. In one example, one or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

Additionally, a surgeon may use one or more components in an exemplary system 900 to make multiple cuts in the bone(s). The multiple cuts may be centered over or around an apex of a deformity or positioned at other locations within the foot such that when the multiple cuts are made, any resected segments removed, or added bone void fillers introduced, and/or bones and/or bone fragments translated and/or rotated the combined angles, surfaces, removed segments, and/or added portions cooperate to provide a desired correction. Each of the components of the exemplary system 900 can be identified, defined, and reviewed using the apparatuses, systems, and/or methods of the present disclosure.

In certain embodiments, the components of the system 900 may be made as small as possible to minimize the amount of soft tissue that is opened in the patient for the osteotomy procedure. Alternatively, or in addition, walls and/or sides of the components may be beveled and/or angled to avoid contact with other hard tissue or soft tissues in the operating field for the osteotomy procedure.

Those of skill in the art will appreciate that for certain osteotomy procedure a complementary component 930 may not be needed or a given complementary component 930 may be optional for use in the osteotomy procedure. Similarly, those of skill in the art will appreciate that certain features of the fasteners 910, resection guides 920, and/or complementary components 930 can be combined into one or more of apparatus or devices or may be provided using a plurality of separate devices.

Figures 10A, 10B:
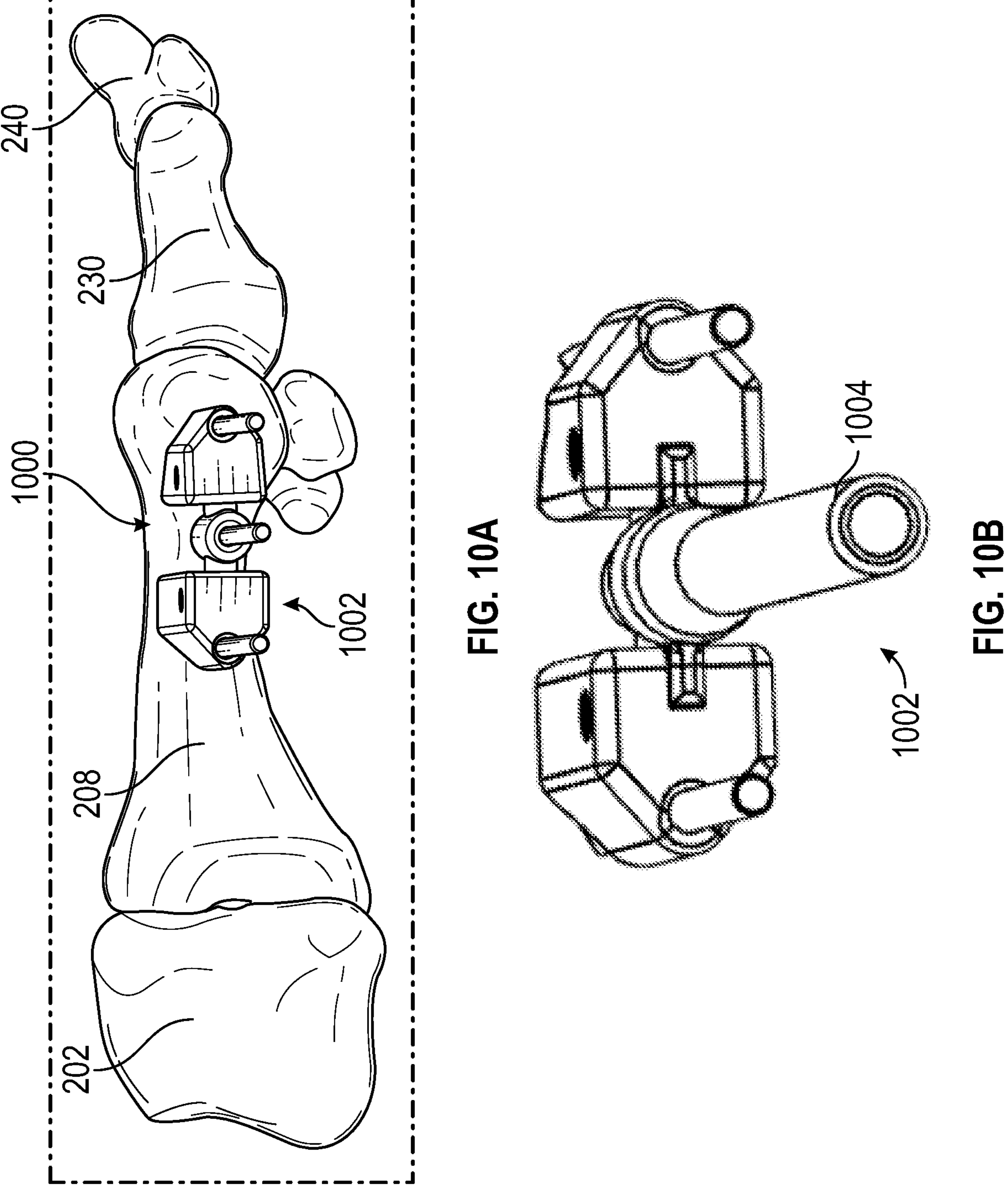
FIG. 10A is a side perspective view of a resection guide according to one embodiment, shown secured to a bone.
FIG. 10B is a perspective view of a resection guide according to one embodiment, that includes a handle.

FIG. 10A is a side perspective view of an osteotomy system 1000 according to one embodiment. The osteotomy system 1000 includes a pivoting resection guide 1002 (which may be also referred to as a swiveling resection guide, rotating resection guide, or pivoting burr guide) according to one embodiment, shown secured to a bone. The pivoting resection guide 1002 may also be referred to as a pivoting cut jig, swiveling resection guide, rotating resection guide, bone dissection guide, arc resection guide, or a pivoting cutting guide based on how the pivoting resection guide 1002 operates. In this example, the pivoting resection guide 1002 is secured to a metatarsal bone. Of course, the pivoting resection guide 1002 can be secured to other bones of a patient to guide a surgeon in making cuts in one or more bones.

In certain embodiments, the pivoting resection guide 1002 is used for dissecting one or more bones. For example, in a bunion surgical procedure a surgeon can use a pivoting resection guide 1002 to resect or dissect a distal end of a cuneiform (e.g., medial cuneiform 202). Alternatively, or in addition, the surgeon may use the same pivoting resection guide 1002, or a different pivoting resection guide 1002, to resect or dissect a proximal end of a metatarsal 208 (e.g., first metatarsal 208). Thus, embodiments of the present disclosure can be used for surgical procedures on a single bone, on multiple bones, and at or across the a joint of a patient.

When secured as illustrated in FIG. 10A, a user may operate the pivoting resection guide 1002 by inserting a cutting tool such as a burr, a burr drill bit, or a drill bit attached to a manual, mechanical, pneumatic, or electric driver into a hole in the guide 1002. A cutting tool may be referred to interchangeably herein as a drill bit. Next, the user may cut into the bone. In the case of a drill bit with longitudinal flutes or burr, the use may initially direct the cutting tool directly into the bone, drilling a hole in the bone. Alternatively, or in addition, the user may initiate an osteotomy of the bone by contacting a rotating cutting section of the cutting tool with a cortex of a bone. Next, a user can pivot the pivoting resection guide 1002 such that the cutting tool (specifically a distal end of the cutting tool) moves laterally in relation to the bone.

For example, in FIG. 10A, a user may pivot the pivoting resection guide 1002 and direct the cutting tool dorsally, as the cutter guide pivots, the cutting tool cuts bone in the dorsal direction. To move the cutting tool in the dorsal direction, the user moves a proximal end of the cutting tool plantarly. Similarly, the user can pivot the cutter guide such that the cutting tool moves plantarly in relation to the bone, as the cutter guide pivots, the cutting tool cuts bone in the plantar direction. To move the cutting tool in the plantar direction, the user moves a proximal end of the cutting tool dorsally. In this manner, a user can resection or dissect a bone.

A cutter guide is a guide of the pivoting resection guide 1002 that guides a cutting tool. Advantageously, such resections can be done using very small incisions, incisions just large enough to insert the cutting tool. Alternatively, or in addition, such resections can be done using incisions just large enough to insert the pivoting resection guide 1002 and engage the pivoting resection guide 1002 to the bone. In certain embodiments, the bone resection can be done subcutaneously. In other embodiments, bone resection can be done percutaneously through an incision (e.g., stab incision) made by, or made for, the cutting tool while the pivoting resection guide 1002 presses against a surface of the skin at the incision location. Accordingly, the pivoting resection guide 1002 provides a minimally invasive surgical (MIS) instrument for use in osteotomies.

FIG. 10B is a perspective view of a cutting guide, such as pivoting resection guide 1002, according to one embodiment, that includes a handle 1004. The handle 1004 is configured to engage a cutter guide and may serve to facilitate pivoting or swiveling the pivoting resection guide 1002 while resecting or dissecting. A surgeon may move the handle 1004 to direct the resection. Rotary cutting tools such as a drill bit, a mill bit, a router bit, a side-cutting burr, burrs, drill bits, and the like provide a high degree of flexibility in how they are oriented and used to resect or dissect bone. Rotary cutting tools rotate about a longitudinal axis of the cutting tool itself. The pivoting resection guide 1002 guides the rotating cutting tool for a dissection and/or resection. Advantageously, the pivoting resection guide 1002 constrains movement of the rotary cutting tool to motion within a single plane. In particular, where the surgeon has planned to form an osteotomy, such as a resection or dissection, having a particular trajectory and/or position on the bone, the pivoting resection guide 1002 assists the surgeon in making a very precision and accurate resection/dissection within a predetermined plane.

Figures 11A, 11B, 11C, 11D:
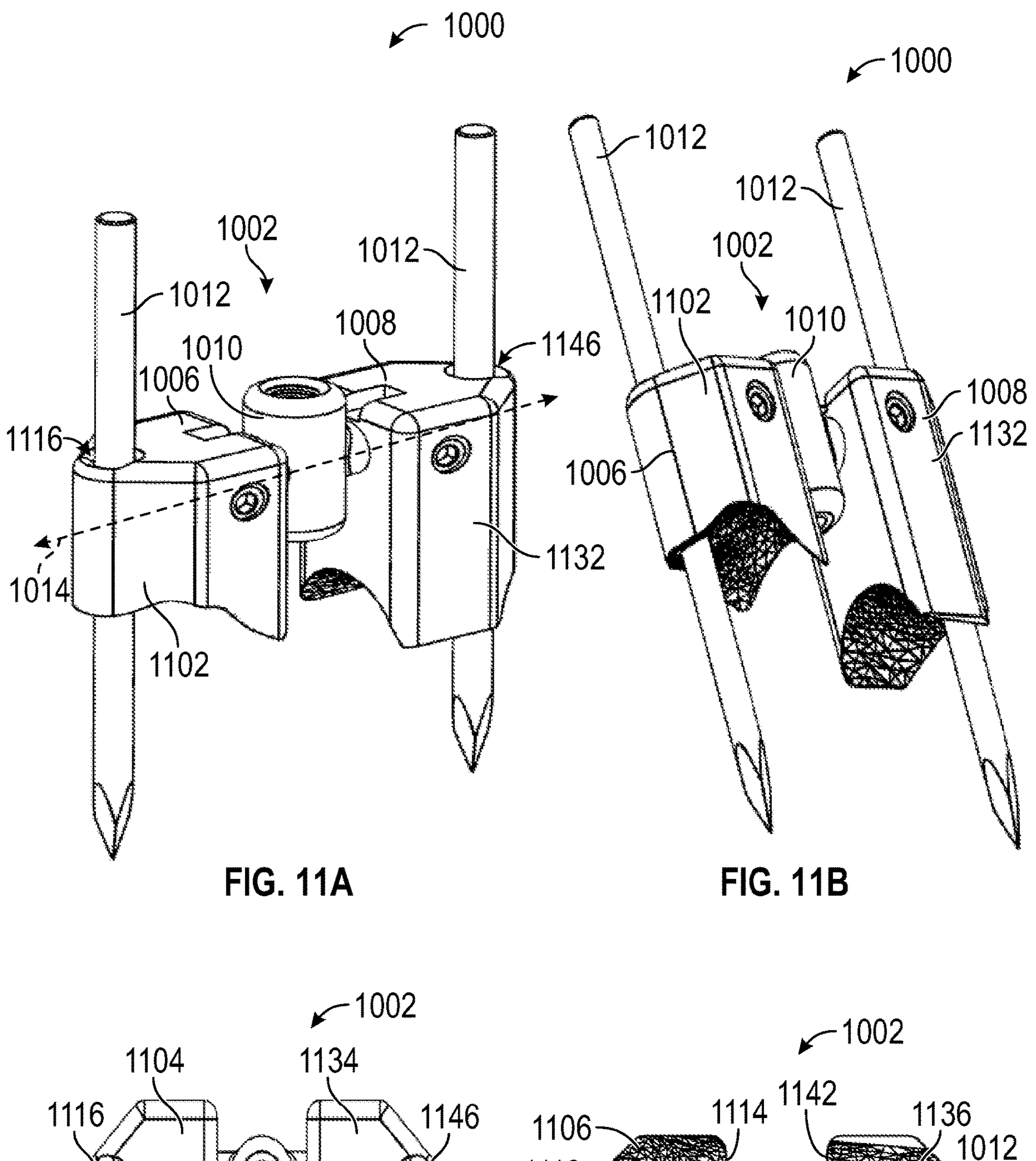
FIG. 11A is a top perspective view of the resection guide, according to one embodiment.
FIG. 11B is a bottom perspective view of the resection guide, according to one embodiment.
FIG. 11C is a top view of the resection guide, according to one embodiment.
FIG. 11D is a bottom view of the resection guide, according to one embodiment.

FIG. 11A is a top perspective view of an osteotomy system 1000 that includes a pivoting resection guide 1002, a handle 1004 (See FIG. 10B), a first bone attachment feature 1006, a second bone attachment feature 1008, a cutter guide 1010, and one or more fasteners 1012. In one embodiment, the fasteners 1012 are temporary fasteners and can be K-wires, pins, or the like. In one embodiment, the fasteners 1012 are configured to engage one or more bones of a patient's foot.

The pivoting resection guide 1002 leverages the first bone attachment feature 1006 and second bone attachment feature 1008 on opposite sides of the cutter guide 1010 to provide a stable platform or base for pivoting the cutter guide 1010 during the osteotomy. The first bone attachment feature 1006 and second bone attachment feature 1008 on opposite sides of the cutter guide 1010 permit the cutter guide 1010 to pivot, swivel, or rotate about a pivot axis in one plane and restrict and prevent movement of the cutter guide 1010 in another plane. In certain embodiments, the pivot axis of rotation for the cutter guide 1010 is an axis that is transverse to a long axis of a cutting tool used with the pivoting resection guide 1002.

In the illustrated embodiment, the first bone attachment feature 1006 and/or second bone attachment features 1008 each include at least one hole configured to receive a pin, such as a fastener 1012. The first bone attachment feature 1006 and/or second bone attachment feature 1008 are configured to secure or anchor the pivoting resection guide 1002 to one or more bones of a patient. The first bone attachment feature 1006 and second bone attachment feature 1008 also serve to hold the cutter guide 1010 in position so accurate cuts can be made using the cutting tool. Consequently, the first bone attachment feature 1006 and second bone attachment feature 1008 are configured to remain in position and hold the cutter guide 1010 despite forces applied to the cutter guide 1010, first bone attachment feature 1006, and second bone attachment feature 1008 by the pivoting action of the cutter guide 1010.

Accordingly, in certain embodiments, the holes of the first bone attachment feature 1006 and second bone attachment feature 1008 and the cross-section diameter of the fasteners 1012 used with the first bone attachment feature 1006 and second bone attachment feature 1008 are sized to withstand these forces. For example, in one embodiment, the holes may be sized to accommodate fasteners 1012 having cross-section diameters of between about 0.8 millimeters to about 2.0 millimeters. Furthermore, the diameter of the holes of the first bone attachment feature 1006 and second bone attachment feature 1008 may be just larger than the diameters of the fasteners 1012 such that the two fit together in a "close fit." Those of skill in the art will appreciate that the diameters of the holes in the first bone attachment feature 1006 and second bone attachment feature 1008 and the fasteners 1012 can very depending on the diameter of the bone or bones that the fasteners 1012 are deployed into.

Smaller diameter bones will use smaller diameter fasteners 1012 and larger diameter bones will use larger diameter fasteners 1012.

The cutter guide 1010 serves to guide a cutting tool as the cutting tool forms the osteotomy. In particular, the cutter guide 1010 is configured to guide a cutting tool in cutting bone along a predefined plane positioned between the first bone attachment feature 1006 and the second bone attachment feature 1008. The cutter guide 1010 guides the cutting tool as the cutter guide 1010 rotates about a pivot axis 1014. In certain embodiments, the pivot axis 1014 is an axis that is transverse to a longitudinal axis of the fasteners 1012 used to secure the first bone attachment feature 1006 and second bone attachment feature 1008. In one embodiment, the pivot axis 1014 is coupled to the first bone attachment feature 1006 and the second bone attachment feature 1008. The pivot axis 1014 is the axis about which the cutter guide 1010 pivots or rotates as the cutter guide 1010 guides the cutting tool to cut within a predetermined plane.

The cutter guide 1010 includes an opening that enables the cutter guide 1010 to accept a cutting tool and guide the cutting tool along a predetermined trajectory as the cutter guide 1010 swivels or pivots about the pivot axis 1014 (e.g., an axis transverse to a long axis of the cutter guide 1010).

FIG. 11B is a bottom perspective view of the pivoting resection guide 1002, according to one embodiment.

FIG. 11C is a top view of the pivoting resection guide 1002, according to one embodiment.

FIG. 11D is a bottom view of the pivoting resection guide 1002, according to one embodiment.

Figures 11E, 11F, 11G, 11H:
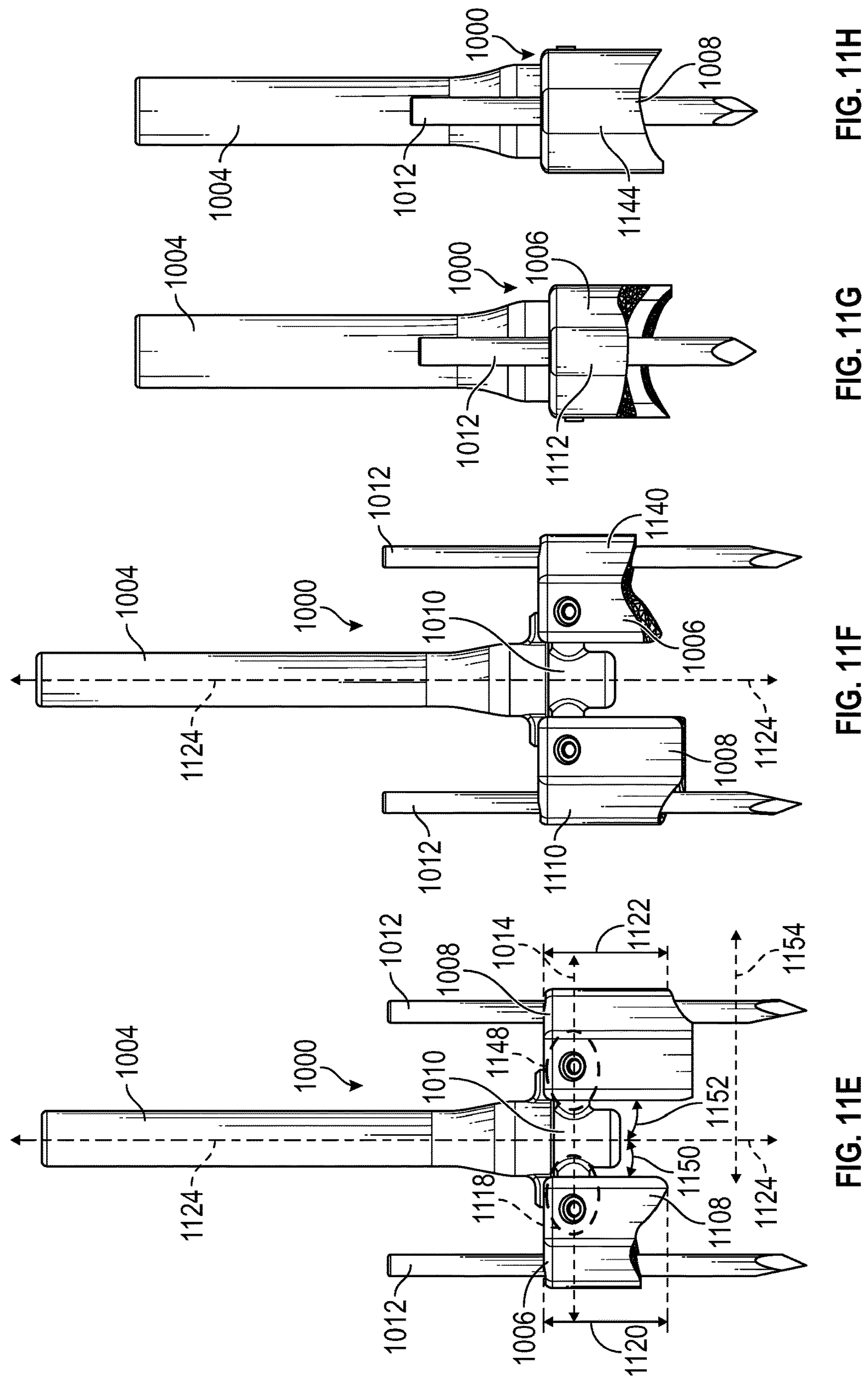
FIG. 11E is a front view of the resection guide, according to one embodiment, including a handle.
FIG. 11F is a back view of the resection guide, according to one embodiment, including a handle.
FIG. 11G is a left side view of the resection guide, according to one embodiment, including a handle.
FIG. 11H is a right-side view of the resection guide, according to one embodiment, including a handle.

FIG. 11E is a front view of the pivoting resection guide 1002, according to one embodiment, including a handle 1004.

FIG. 11F is a back view of the pivoting resection guide 1002, according to one embodiment, including a handle 1004.

FIG. 11G is a left side view of the pivoting resection guide 1002, according to one embodiment, including a handle 1004.

FIG. 11H is a right-side view of the pivoting resection guide 1002, according to one embodiment, including a handle 1004.

Referring now to FIGS. 11A-11H, more details of the illustrated embodiment will be described. Those of skill in the art will appreciate that depending on where on, or in, the body of a patient, a pivoting resection guide 1002 is used, the pivoting resection guide 1002 can have sides that are named differently than those described in relation to the illustrated embodiment (e.g., top, bottom, front, back, left, right). However, with respect to the illustrated embodiment, this illustrated pivoting resection guide 1002 is configured for use on, at, between, or near a medial cuneiform 202 and/or a first metatarsal 208 of a patient. Consequently, the sides of the components of the osteotomy system 1000 are named based on where those sides are positioned and/or oriented when this pivoting resection guide 1002 is in use.

As shown in one or more of FIGS. 11A-11H, the first bone attachment feature 1006 includes a body 1102 which includes a superior side 1104, an inferior side 1106, a medial side 1108, a lateral side 1110, a proximal side 1112, a distal side 1114, at least one opening 1116, and a first coupler 1118. Similarly, the second bone attachment feature 1008 includes a body 1132 which includes a superior side 1134, an inferior side 1136, a medial side 1138, a lateral side 1140, a proximal side 1142, a distal side 1144, at least one opening 1146, and a second coupler 1148. The body 1102 and/or body 1132 can be fabricated using additive or subtractive manufacturing.

In the illustrated embodiment when in use, the superior side 1104 and superior side 1134 face away from one or more bones of the patient. The inferior side 1106 and inferior side 1136 face one or more bones of the patient. The proximal side 1112 and proximal side 1142 are proximal to the patient and the distal side 1114 and distal side 1144 are distal to the patient. The medial side 1108 and medial side 1138 face a medial side of the patient and the lateral side 1110 and lateral side 1140 face a distal side of the patient.

The opening 1116 extends from the superior side 1104 to the inferior side 1106. The opening 1146 extends from the superior side 1134 to the inferior side 1136. Each of opening 1116 and opening 1146 are sized to receive a respective fastener 1012. The opening 1116 and opening 1146 may each have the same or similar or different diameter openings. Each of opening 1116 and opening 1146 are configured to receive one of one or more fasteners 1012.

The first coupler 1118 is configured to engage with a cutter guide 1010 positioned between the first bone attachment feature 1006 and the second bone attachment feature 1008. In one embodiment, the first coupler 1118 may engage and secure the cutter guide 1010 between the first bone attachment feature 1006 and the second bone attachment feature 1008. In one embodiment, the first coupler 1118 may engage and secure the cutter guide 1010 to the first bone attachment feature 1006 while a second coupler 1148 may engage but not secure the cutter guide 1010 to the second bone attachment feature 1008.

Advantageously, the first coupler 1118 engages with the cutter guide 1010 such that the cutter guide 1010 remains in place and is capable of pivoting or rotating about the pivot axis 1014. In certain embodiments, the first coupler 1118 engages the cutter guide 1010 such that the pivot axis 1014 of the cutter guide 1010 is perpendicular to the distal side 1114 of the first bone attachment feature 1006. In another embodiment, the first coupler 1118 engages the cutter guide 1010 such that the pivot axis 1014 of the cutter guide 1010 is at an angle that is not perpendicular to the distal side 1114 of the first bone attachment feature 1006.

The second coupler 1148 is configured to engage with a cutter guide 1010 positioned between the first bone attachment feature 1006 and the second bone attachment feature 1008. In one embodiment, the second coupler 1148 may engage and secure the cutter guide 1010 between the first bone attachment feature 1006 and the second bone attachment feature 1008. In one embodiment, the second coupler 1148 may engage and secure the cutter guide 1010 to the second bone attachment feature 1008 while a first coupler 1118 may engage but not secure the cutter guide 1010 to the first bone attachment feature 1006.

Advantageously, the second coupler 1148 engages with the cutter guide 1010 such that the cutter guide 1010 remains in place and is capable of pivoting or rotating about the pivot axis 1014. In certain embodiments, the second coupler 1148 engages the cutter guide 1010 such that the pivot axis 1014 of the cutter guide 1010 is perpendicular to the proximal side 1142 of the second bone attachment feature 1008. In another embodiment, the second coupler 1148 engages the cutter guide 1010 such that the pivot axis 1014 of the cutter guide 1010 is at an angle that is not perpendicular to the proximal side 1142 of the second bone attachment feature 1008.

Referring now back to FIG. 11D, FIG. 11D illustrates an embodiment of the pivoting resection guide 1002 that includes a first bone attachment feature 1006 having a first bone engagement surface 1022 that is contoured to substantially match a surface contour of bone (e.g., a proximal metatarsal surface contour) where the pivoting resection guide 1002 is to be anchored/secured. In certain embodiments, the pivoting resection guide 1002 can include a second bone attachment feature 1008 having a second bone engagement surface 1024 that is contoured to substantially match a surface contour of bone (e.g., a distal metatarsal surface contour) where the pivoting resection guide 1002 is to be anchored/secured. Alternatively, or in addition, the first bone engagement surface 1022 and/or second bone engagement surface 1024 may be contoured based on placement of the pivoting resection guide 1002 on a surface of skin of a patient for a procedure.

In the illustrated embodiment, the first bone engagement surface 1022 is on the inferior side 1106 of the first bone attachment feature 1006 and the second bone engagement surface 1024 is on the inferior side 1136 of the second bone attachment feature 1008. In certain embodiments, only one of the first bone attachment feature 1006 and/or second bone attachment feature 1008 may include a bone engagement surface. The first bone engagement surface 1022 and/or second bone engagement surface 1024 are/is configured to engage a cortical bone surface of one or more bones during a surgical procedure (e.g., forming an osteotomy).

Advantageously, the first bone engagement surface 1022 and/or second bone engagement surface 1024 assists a surgeon in placement and orientation of the pivoting resection guide 1002 in a desired placement and/or orientation relative one or more bones. In certain embodiments, the first bone engagement surface 1022 and/or second bone engagement surface 1024 is at least partially determined based on a bone model 404 of a patient's foot. In certain embodiments, the bone model 404 is defined based on medical imaging of the patient's foot.

In certain embodiments, the inferior surfaces of the first bone attachment feature 1006 and/or the second bone attachment feature 1008 may be planar and may not be configured to conform, or substantially match a surface contour of bone (e.g., a metatarsal) where the pivoting resection guide 1002 is to be anchored/secured. Alternatively, or in addition, the inferior surfaces of the first bone attachment feature 1006 and/or the second bone attachment feature 1008 may be contoured to sit on a surface of skin of a patient that covers the bone (e.g., a metatarsal).

In certain embodiments, the first bone attachment feature 1006 and second bone attachment feature 1008 may straddle a joint with the first bone attachment feature 1006 on one side of the joint and the second bone attachment feature 1008 on the other side of the joint. In another embodiment, the first bone attachment feature 1006 and second bone attachment feature 1008 may be secured along a length of the same bone.

Referring now to FIG. 11E, the first bone attachment feature 1006 includes a first height 1120 that extends from a highest point on the surface of the superior side 1104 to a lowest point on the surface of the inferior side 1106. Similarly, the second bone attachment feature 1008 includes a second height 1122 that extends from a highest point on the surface of the superior side 1134 to a lowest point on the surface of the inferior side 1136.

FIGS. 11E and 11F illustrate an embodiment of the osteotomy system 1000 in which the first coupler 1118, second coupler 1148, first height 1120, and second height 1122 are each configured to define a trajectory 1124 for the cutter guide 1010 relative to one or more bones that receive the osteotomy. The trajectory 1124 for the cutter guide 1010 defines the trajectory of a cutting tool used with the cutter guide 1010 to resect or dissect one or more bones.

In the illustrated embodiment, the first coupler 1118, second coupler 1148, first height 1120, and second height 1122 are configured such that the trajectory 1124 is parallel to the longitudinal axes of the fasteners 1012. Those of skill in the art will appreciate that one or more of the first height 1120 and/or second height 1122 and/or how the first coupler 1118 and/or second coupler 1148 engage with the cutter guide 1010 can be changed to provide a different angle for the trajectory 1124 relative to the first bone attachment feature 1006 and/or second bone attachment feature 1008 and/or to the longitudinal axes of the fasteners 1012. Said another way, the first coupler 118, second coupler 1148, first height 120, and second height 122 can be related and/or correlated to define the trajectory 1124 for the cutter guide 1010 towards one or more bones.

Alternatively, or in addition, the angle of the opening 1116 through the body 1102 of the first bone attachment feature 1006 and/or the angle of the opening 1146 through the body 1132 of the second bone attachment feature 1008 can be used to define a trajectory 1124 for the cutter guide 1010. The angle of the openings 1116, 1146 alone or together with one or more of the first coupler 1118, second coupler 1148, first height 1120, and/or second height 1122 can be used separately and/or together in different combinations to define the trajectory 1124. Each of these permutations and/or combinations are within the scope of the present disclosure. In the illustrated embodiment, the angle of the opening 1116 through the body 1102 of the first bone attachment feature 1006 and/or the angle of the opening 1146 through the body 1132 of the second bone attachment feature 1008 are each perpendicular to the pivot axis 1014.

FIG. 11E illustrates that the first coupler 1118 engages the cutter guide 1010 at a first angle 1150 that is perpendicular to the distal side 1114 of the first bone attachment feature 1006 and that the second coupler 1148 engages the cutter guide 1010 at a second angle 1152 that is perpendicular to the proximal side 1142 of the second bone attachment feature 1008. FIG. 11E illustrates a longitudinal axis 1154 that represents the longitudinal axis of a bone that is to be resected (e.g., first metatarsal 208).

FIG. 11E illustrates that the first height 1120 and the second height 1122 are defined such that the trajectory 1124 of the cutter guide 1010 extends substantially perpendicular to the longitudinal axis 1154 of at least one of the bones that is to be resected/dissected using the pivoting resection guide 1002. In one example, the longitudinal axis 1154 may be a long axis of a first metatarsal 208. In certain embodiments, the first height 1120 and second height 1122 may be of the same or substantially the same magnitude. The size of the first height 1120 and/or second height 1122 can vary depending on the contour of a bone surface that contacts the first bone attachment feature 1006 and second bone attachment feature 1008, the first angle 1150, the second angle 1152, an angle of the opening 1116, an angle of the opening 1146, whether the pivoting resection guide 1002 will span a joint and involve two bones, and the like. Advantageously, each of these aspects can be accounted for and accommodated when models of the bones of the patient and/or models of instruments such as the osteotomy system 1000 are reviewed and defined during preoperative planning stages in accordance with the present disclosure.

In the illustrated embodiment, the first angle 1150 and the second angle 1152 are right angles. Of course, in certain embodiments, the first angle 1150 may not be at a right angle with respect to the distal side 1114 of the first bone attachment feature 1006 and the second angle 1152 may not be at a right angle with respect to the proximal side 1142 of the second bone attachment feature 1008. Alternatively, or in addition, the first height 1120 and/or second height 1122 may be defined such that the trajectory 1124 of the cutter guide 1010 extends at an angle that is not perpendicular to the longitudinal axis 1154 of at least one of the bones that is to be resected/dissected using the pivoting resection guide 1002. Accordingly, in this manner, the angle of the trajectory 1124 can be predetermined and/or can be patient-specific to meet the needs of the patient, the angle needed for a correction, the preferences of a surgeon, or the like.

FIGS. 11A-11H, illustrate an embodiment of an osteotomy system 1000 that includes both a first bone attachment feature 1006 and a second bone attachment feature 1008 with a cutter guide 1010 between them. However, certain embodiments of an osteotomy system may have substantially the same constructs, components, and aspects as those described with respect to embodiments in FIGS. 11A-11H with the exception that these embodiments may include either the first bone attachment feature 1006 or the second bone attachment feature 1008. Thus, the present disclosure supports embodiments of a pivoting resection guide that includes one of the first bone attachment feature 1006 or the second bone attachment feature 1008 but not both. Such an embodiment can also include a first bone engagement surface 1022 or second bone engagement surface 1024 depending on which bone attachment feature is included. The first bone engagement surface 1022 or second bone engagement surface 1024 may be determined at least in part based on a model of a bone of a patient's foot. In certain embodiments, the bone is the bone that the first bone attachment feature 1006 or the second bone attachment feature 1008 will contact during the surgical procedure.

For example, suppose in one embodiment, the osteotomy system includes a first bone attachment feature 1006, at least one fastener 1012, a cutting tool 1026, and the cutter guide 1010. Accordingly, the first bone attachment feature 1006 includes a first bone engagement surface 1022 that is configured to engage with a bone surface to position the first bone attachment feature 1006 for the surgical procedure. Alternatively, in another embodiment, the osteotomy system includes a second bone attachment feature 1008, at least one fastener 1012, a cutting tool 1026, and the cutter guide 1010. Accordingly, the second bone attachment feature 1008 includes a second bone engagement surface 1024 that is configured to engage with a bone surface to position the second bone attachment feature 1008 for the surgical procedure.

Figures 12A, 12B:
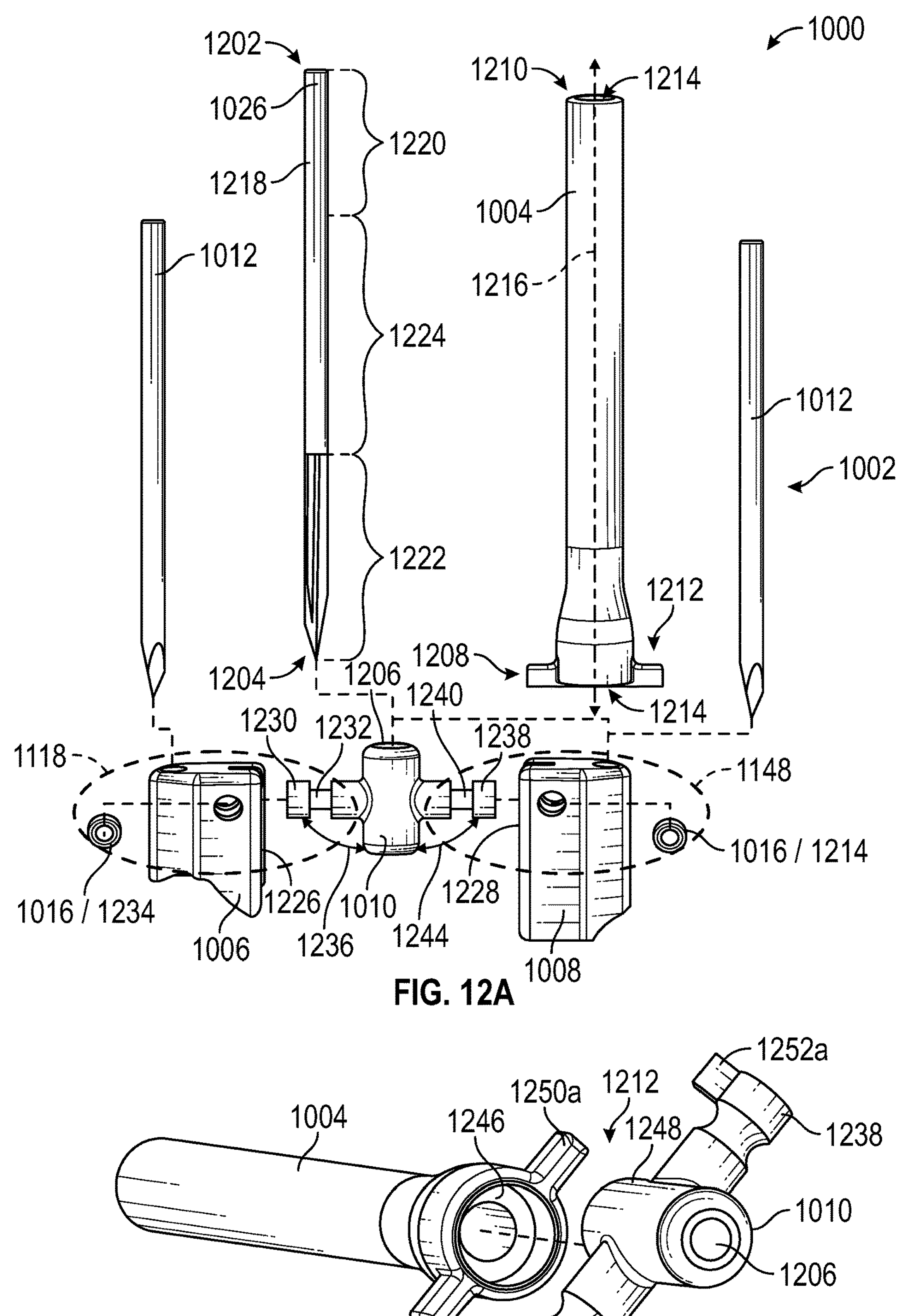
FIG. 12A is an exploded view of the resection guide, according to one embodiment, including a handle.
FIG. 12B is an exploded view of a handle and a cutter guide, according to one embodiment.

FIG. 12A is an exploded view of a pivoting resection guide 1002, according to one embodiment, including a handle 1004. The osteotomy system 1000 includes a cutting tool 1026, first bone attachment feature 1006, second bone attachment feature 1008, cutter guide 1010 and the first coupler 1118 and second coupler 1148 describe earlier.

The cutter guide 1010 is configured to receive a cutting tool 1026 such as a burr, a drill bit, or the like. The cutting tool 1026 can also be referred to as a cutter. The cutting tool 1026 includes a proximal end 1202 and a distal end 1204. The cutting tool 1026 is configured to be deployed within an opening 1206 in the cutter guide 1010. In one embodiment, the opening 1206 in the cutter guide 1010 extends from one end to the other. The opening 1206 extends from a proximal end of the cutter guide 1010 to a distal end of the cutter guide 1010. The opening 1206 of the cutter guide is sized and shaped to accept at least the cutting section 1222 of the cutting tool cutting tool 1026.

The handle 1004 provides precise and accurate control of the cutting tool 1026 as the pivoting resection guide 1002 is used to guide the cutting tool 1026 is performing an osteotomy. The handle 1004 enables a surgeon to pivot the cutter guide 1010 with fine control within a plane between the first bone attachment feature 1006 and the second bone attachment feature 1008 and without interference from the cutting tool 1026.

The handle 1004 includes a distal handle end 1208 and a proximal handle end 1210 opposite the distal handle end 1208. The distal handle end 1208 includes a handle coupler 1212. The handle coupler 1212 is configured to couple the handle 1004 to the cutter guide 1010, at least temporarily. The handle 1004 also includes an opening 1214 that extends from the proximal handle end 1210 to the distal handle end 1208. In certain embodiments, the opening 1214 is coaxial with a longitudinal axis 1216 of the handle 1004. The opening 1214 is sized to accept the cutting tool 1026. In particular, the handle 1004 is configured to pass the cutting tool 1026 through the handle 1004. The handle coupler 1212 couples the handle 1004 to the cutter guide 1010. Coupling the handle 1004 to the cutter guide 1010 forms a first-class lever. The first-class lever magnifies a load force applied to a bone in contact with the cutting tool 1026 near the distal end 1204 of the cutting tool 1026 based on an effort force applied by a user toward the proximal handle end 1210.

The cutting tool 1026 includes a body 1218 that includes a drive section 1220, a cutting section 1222, and a guide section 1224 between the drive section 1220 and the cutting section 1222. In one embodiment, the body 1218 is an elongate body with a round cross section. The drive section 1220 is near the proximal end 1202 and is configured to couple to a driver that rotates the cutting tool 1026. The guide section 1224 engages with the pivoting resection guide 1002 and guides the cutting tool 1026 during the creation of an osteotomy. The cutting section 1222 is near the distal end 1204. The cutting section 1222 is the part that resects/dissects the bone to form an osteotomy. In one embodiment, the cutting section 1222 includes a set of flutes or grooves that include sharp edges configured to cut and resect hard tissue and/or soft tissue.

In certain embodiments, the cutting section 1222 has a predetermined length. This predetermined length may be patient-specific. Alternatively, or in addition, the predetermined length is configured based on a diameter of the tissue the cutting tool 1026 will resect/dissect. In certain embodiments, the predetermined length is configured to extend from one cortex of a bone to an opposite cortex of the bone when the cutting tool 1026 is used to resect the bone. Alternatively, or in addition, the cutting tool 1026 can be used to form a channel or bone tunnel or recess, in such cases the predetermined length may be set to accommodate that use.

In the illustrated embodiment, the cutter guide 1010 includes two arms that each extend into an opening 1226, 1228 in each of the first bone attachment feature 1006 and the second bone attachment feature 1008. The arms may be secured in the openings using one or more fasteners 1016 (e.g., set screws, thumbscrews, pins, dowels, or the like). Together the arms, openings, and/or fasteners 1016 may operate as one example of a first coupler 1118 and/or second coupler 1148.

Referring still to FIG. 12A, in one embodiment, the first coupler 1118 includes a proximal arm 1230, a proximal arm groove 1232, and a proximal arm retainer 1234. The proximal arm 1230 extends from a first side of the cutter guide 1010 at a first arm angle 1236 towards the first bone attachment feature 1006. In the illustrated embodiment, the proximal arm 1230 is a cylindrical structure that extends from the cutter guide 1010. The opening 1226 is also circular which allows the proximal arm 1230 to rotate within the opening 1226.

The proximal arm groove 1232 may be toward a distal end of the proximal arm 1230. The proximal arm groove 1232 circumscribes the proximal arm 1230 and cooperates with the proximal arm retainer 1234 to retain the proximal arm 1230 within the opening 1226. In the illustrated embodiment, the proximal arm retainer 1234 is a set screw that passes through an opening in the body 1102 of the first bone attachment feature 1006 and extends into the proximal arm groove 1232. The proximal arm retainer 1234 engages the body 1102 of the first bone attachment feature 1006 and the proximal arm groove 1232 to couple the proximal arm 1230 to the first bone attachment feature 1006.

The proximal arm retainer 1234 provides interference within the proximal arm groove 1232 such that the proximal arm 1230 is retained within the opening 1226. Of course, a set screw is but one example of a suitable proximal arm retainer 1234. In one embodiment, the proximal arm retainer 1234 is a thumbscrew, which may enable a user to readily release a proximal arm 1230 so that the cutter guide 1010 can be swapped with another one. The proximal arm retainer 1234 may also be a pin, a screw, a bolt, or the like. In the illustrated embodiment, the first arm angle 1236 is a right angle such that the longitudinal axis of the cutter guide 1010 is parallel to the distal side 1114 of the first bone attachment feature 1006. Those of skill in the art will appreciate that the first arm angle 1236 can be a variety of angles and can be patient-specific such that the trajectory 1124 of the cutter guide 1010 can be predetermined based, at least in part on the first arm angle 1236.

In the illustrated embodiment, the second coupler 1148 in one embodiment, includes a distal arm 1238, a distal arm groove 1240, and a distal arm retainer 1242. The distal arm 1238 extends from a second side of the cutter guide 1010 at a second arm angle 1244 towards the second bone attachment feature 1008. In the illustrated embodiment, the distal arm 1238 is a cylindrical structure that extends from the cutter guide 1010. The opening 1228 is also circular which allows the distal arm 1238 to rotate within the opening 1228.

The distal arm groove 1240 may be toward a distal end of the distal arm 1238. The distal arm groove 1240 circumscribes the distal arm 1238 and cooperates with the distal arm retainer 1242 to retain the distal arm 1238 within the opening 1228. In the illustrated embodiment, the distal arm retainer 1242 is a set screw that passes through an opening in the body 1132 of the second bone attachment feature 1008 and extends into the distal arm groove 1240. The distal arm retainer 1242 engages the body 1132 of the second bone attachment feature 1008 and the distal arm groove 1240 to couple the distal arm 1238 to the second bone attachment feature 1008.

The distal arm retainer 1242 provides interference within the distal arm groove 1240 such that the distal arm 1238 is retained within the opening 1228. Of course, a set screw is but one example of a suitable distal arm retainer 1242. In one embodiment, the distal arm retainer 1242 is a thumbscrew, which may enable a user to readily release a distal arm 1238 so that the cutter guide 1010 can be swapped with another one. The distal arm retainer 1242 may also be a pin, a screw, a bolt, or the like. In the illustrated embodiment, the second arm angle 1244 is a right angle such that the longitudinal axis of the cutter guide 1010 is parallel to the proximal side 1142 of the second bone attachment feature 1008. Those of skill in the art will appreciate that the second arm angle 1244 can be a variety of angles and can be patient-specific such that the trajectory 1124 of the cutter guide 1010 can be predetermined based, at least in part on the second arm angle 1244.

As described herein, the first coupler 1118 and/or second coupler 1148 are, or can be, configured to retain a pivot arm, also referred to as an arm of the cutter guide 1010. The first coupler 1118 and second coupler 1148 retain the pivot arms to keep the cutter guide 1010 stable and positioned at a desired position between the first bone attachment feature 1006 and the second bone attachment feature 1008. Advantageously, the first coupler 1118 and second coupler 1148 also enable the cutter guide 1010 to rotate about at least one pivot arm. In certain embodiments, one of the couplers (e.g., first coupler 1118 and/or second coupler 1148) may retain a single pivot arm of a cutter guide 1010 and enable the cutter guide 1010 to rotate about that single pivot arm.

FIG. 12B is an exploded view of a handle 1004 and a cutter guide 1010, according to one embodiment. FIG. 12B illustrates one implementation of a handle coupler 1212. The handle coupler 1212 can include a recess 1246 that extends from a distal handle end 1208 towards the proximal handle end 1210. In certain embodiments, the recess 1246 is concentric with the opening 1214 of the handle 1004. In certain embodiments, the recess 1246 has a cross section that is the same or complimentary to a proximal end 1248 of the cutter guide 1010. In the illustrated embodiment, the recess 1246 having a cross-sectional shape and size configured to accept the proximal end 1248 of the cutter guide 1010 into the recess 1246.

In certain embodiments, the handle coupler 1212 may also include at least one arm 1250. The arm 1250 may extend radially from the handle 1004 near a distal handle end 1208 of the handle 1004. The arm 1250 is configured to engage with one or the other of the first bone attachment feature 1006 and the second bone attachment feature 1008. For example, in the illustrated embodiment, the handle 1004 includes a first arm 1250*a* extending from one side and a second arm 1250*b* extending from an opposite side. The arm 1250 are configured to seat and/or rotate with a recess 1018 (See FIGS. 14A, 14B) in a superior side 1104 of the first bone attachment feature 1006 and/or a superior side 1134 of the second bone attachment feature 1008. The recesses may be shaped to receive the arms 1250*a*, 1250*b* that extend from the handle 1004 to engage the handle 1004 when coupled to the cutter guide 1010. Those of skill in the art will appreciate that the pivoting resection guide 1002 can be used with or without a handle 1004. Where a handle 1004 is not used, the user may pivot a cutting tool 1026 using a driver of the cutting tool 1026, which may include a handle of its own. In such an embodiment, the driver may serve the same or a similar function to the handle 1004 described in embodiments herein.

In certain embodiments, the pivoting resection guide 1002 includes one or more stops referred to as rotational stops. These one or more stops serve to stop, prevent, slow, or hinder rotational movement of the cutter guide 1010 about the pivot axis 1014. Those of skill in the art will appreciate that implementations of the one or more stops can take a variety of forms. Referring to FIG. 12B, in one example, one or more of the proximal arm 1230 and the other distal arm 1238 can be configured to include one or more tabs 1252 in addition, one or more of the openings 1226, 1228 can be configured to such that an arm that includes a tab 1252 is capable of rotating with the cutter guide 1010 about the pivot axis 1014 through a set range of angles but no further. For example, the openings 1226, 1228 may include a cross section that is semi-circular on one side and then angle to interfere with one or more of the tabs 1252 as the distal arm 1238 and/or proximal arm 1230 rotates within the openings 1226, 1228. Those of skill in the art will appreciate that tabs 1252 is but one example of how one of skill in the art may implement a stop to manage a range or arc of pivot that the cutter guide 1010 can guide a cutting tool 1026 through.

In certain embodiments, the amount of pivot or rotation permitted for the cutter guide 1010 can be predefined, can be set for all pivoting resection guides 1002, can be patient matched for a patients having certain characteristics (e.g., age, gender, condition), and/or can be patient-specific. In certain embodiments, the range of pivot angle permitted for the cutter guide 1010 can be between about 30 degrees and about 50 degrees.

In certain embodiments, the pivoting resection guide 1002 may be custom designed such that the distance the pivoting resection guide 1002 can be rotated about pivot axis 1014 is controlled/limited/predefined or restricted. Advantageously, this rotational limit may be a patient-specific limit to the rotation or pivot of the pivoting resection guide 1002. Advantageously, the rotational limit can help a surgeon to resect only where desired and no further.

Figure 13A:
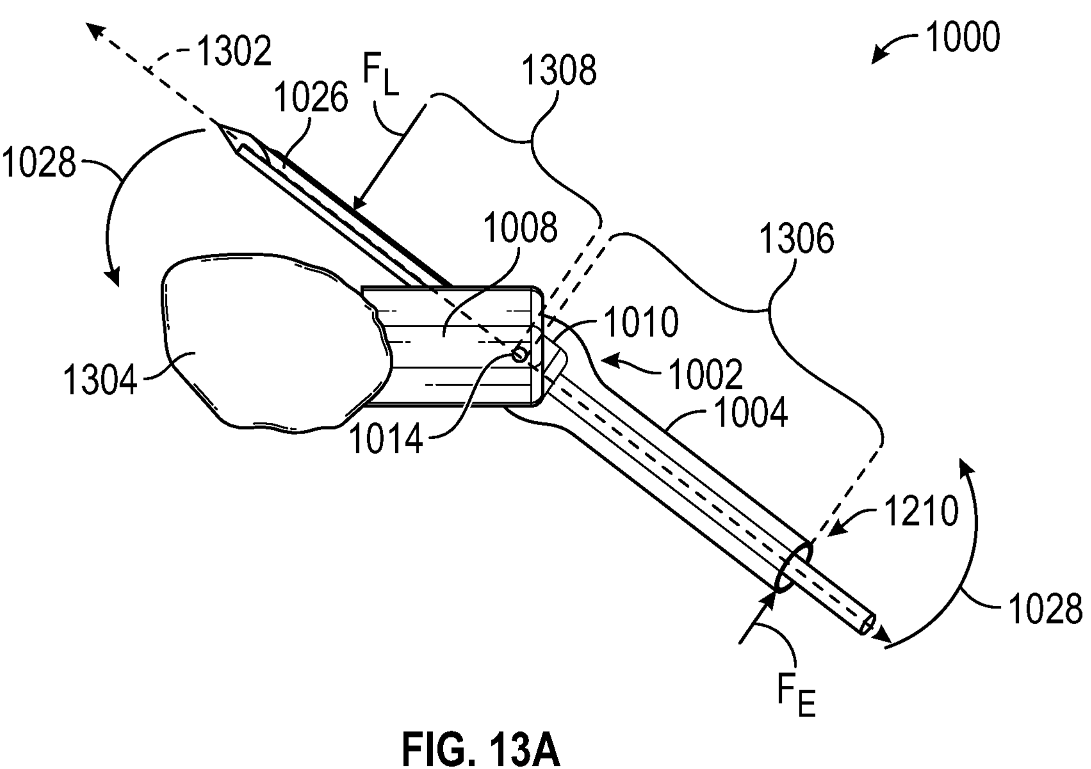
FIG. 13A is a side view of the resection guide, according to one embodiment, in one pivot position.

FIG. 13A is a side view of the pivoting resection guide 1002, according to one embodiment, in one pivot position. Advantageously, the cutter guide 1010 is configured to pivot about a pivot axis 1014 that runs transverse to a longitudinal axis 1302 of the cutter guide 1010. In the illustrated embodiment, the step 104 is perpendicular to the longitudinal axis 1302. The pivoting resection guide 1002 is configured to provide a first-class lever for a surgeon to use to make accurate and precise osteotomies of one or more bones.

The first-class lever includes the cutting tool 1026, the cutter guide 1010, and either the handle 1004 in combination with a driver (not shown) of the cutting tool 1026 or just the driver. In the illustrated embodiment, the handle 1004 passes the cutting tool 1026 through the opening 1214 and couples (e.g., handle coupler 1212) to the cutter guide 1010 to form the first-class lever. Alternatively, or in addition, the driver of the cutting tool 1026 may be coupled to the cutting tool 1026 and the cutting section 1222 passed through the cutter guide 1010 and together with the driver, cutting tool 1026, and cutter guide 1010 form a first-class lever. In either case, the first bone attachment feature 1006 and second bone attachment feature 1008 cooperate with the first coupler 1118 and the second coupler 1148 to provide a fulcrum for the first-class lever. The fulcrum includes the pivot axis 1014.

"First-class Lever" refers to a type of lever. A lever is a simple machine that includes a fulcrum, a lever arm, and a load arm. In the embodiment of FIG. 13A, the cutter guide 1010, pivot axis 1014, and first bone attachment feature 1006 and/or second bone attachment feature 1008 can serve as the fulcrum.

In a first-class lever, the lever arm and load arm are on opposite ends of a rigid structure and the fulcrum engages with, and enables, the rigid structure to pivot or rotate about an axis transverse to the rigid structure and positioned at the fulcrum. The fulcrum is between the load arm and the lever arm.

The lever arm receives or encounters an effort force, and the load arm receives or encounters a load. Traditionally, the rigid structure is a planar structure, however, the rigid structure can also be a cylindrical structure that may or may not have an opening that extends the length of and through the center of the cylindrical structure. The lever arm is the part of the rigid structure that accepts or receives an effort force applied to the lever arm to operate the lever. The load arm is the part of the rigid structure that accepts, receives, or acts against a load. A load force is a force created by the load arm in response to the effort force applied to the lever arm.

A fulcrum is a point or structure about which a lever pivots or rotates. The length of the lever arm is the distance from where the effort force is applied to the fulcrum. The length of the load arm is the distance from the fulcrum to where the load arm encounters the load. A fulcrum is a pivot point or pivot axis of the lever that converts an effort force applied perpendicular to the lever arm into a load force perpendicular to the load where the load arm contacts the load.

Applying an effort force to the lever arm creates a moment or torque about the fulcrum equal to the magnitude of the force multiplied by the length of the lever arm (e.g., the distance from where the effort force is applied along the lever arm to the fulcrum). The lever arm and effort force create a mechanical advantage at the point that the load arm encounters the load.

Specifically, the mechanical advantage is defined as the length of the lever arm divided by the length of the load arm. The mechanical advantage provides a magnitude for how much the effort force is multiplied. In a first-class lever configuration, the force on the load is equal to the effort force multiplied by the length of the lever arm (the distance between where the effort force is applied perpendicular to the lever arm and the fulcrum). This is the principle of torque. Thus, in general, the longer the lever arm the greater the force applied to the load with the same level of effort force. The present disclosure uses the benefits of a first-class lever. Of course, other embodiments may implement a second-class or third-class lever to facilitate applying a force to a load.

In the illustrated embodiment, the cutting tool 1026, cutter guide 1010, driver, and optionally the handle 1004 cooperate to provide the rigid structure of the first-class lever. The lever arm 1306 is the distance between the pivot axis 1014 and where an effort force ($F_E$) is applied to the lever. The distance of the lever arm 1306 has a measurable length. The load arm 1308 is the distance between the pivot axis 1014 and where a load force ($F_L$) is applied to the load (e.g., the bone 1304). The distance of the load arm 1308 has a measurable length. Generally, the $F_L$ will be a point where the cutting section 1222 contacts the bone 1304. As the cutting section 1222 encounters more bone material the $F_L$ may move more distally. The bone 1304 contacts the cutting tool 1026 near the distal end 1204 of the cutting tool 1026.

Advantageously, the first-class lever formed by, and using, the pivoting resection guide 1002 magnifies the $F_L$ that is applied to the bone 1304. Consequently, resection/dissection of the bone 1304 requires less effort, less $F_E$. In this manner, the pivoting resection guide 1002 facilitates resection/dissection of harder and/or more dense bone, such as that of the cortex of the bone 1304.

The pivot axis 1014 serves as, or as part of a fulcrum for the first-class lever of the pivoting resection guide 1002. The magnitude of the load force ($F_L$) is the effort force ($F_E$) multiplied by the length of the lever arm 1306. The lever arm 1306 is a distance between the fulcrum (e.g., pivot axis 1014) and a point toward the proximal handle end 1210 where the effort force ($F_E$) is applied (e.g., by a user).

Figure 13B:
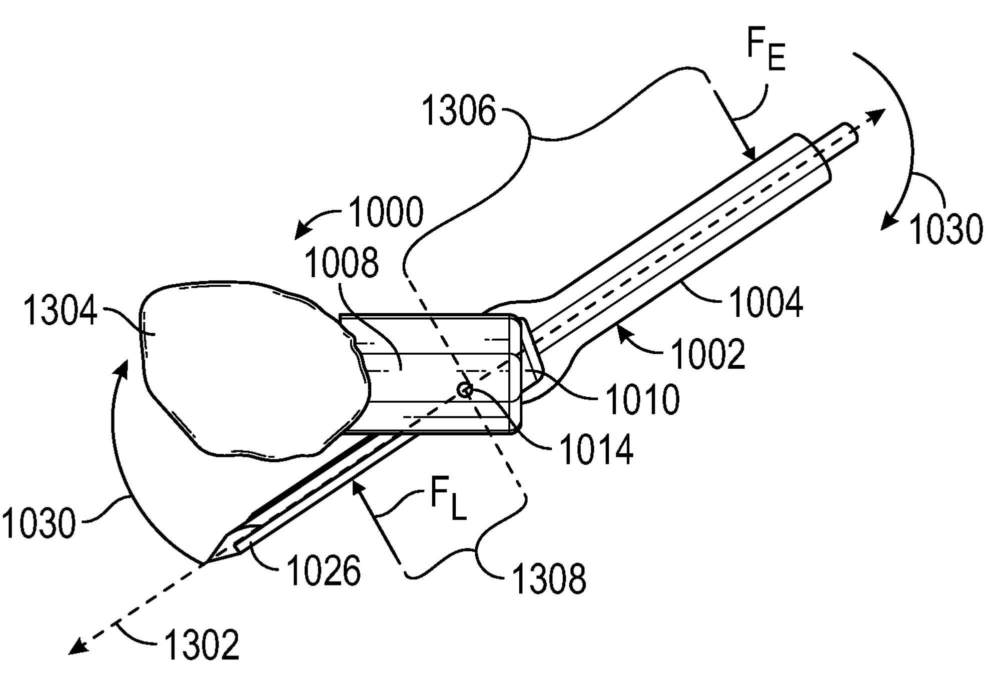
FIG. 13B is a side view of the resection guide, according to one embodiment, in another pivot position.

FIGS. 13A and 13B illustrate an example of the pivoting resection guide 1002 as a first-class lever in action. The example illustrates the pivoting resection guide 1002 attached to a medial side of bone 1304. The handle 1004 is moved counterclockwise direction 1028 (e.g., dorsally) and the lever pivots about pivot axis 1014. As the cutter guide

1010 pivots about the pivot axis 1014, the distal end of the cutting tool 1026 moves counterclockwise in direction 1030 (e.g., plantarly) and removes parts of a bone 1304. By operating the cutting tool 1026 and pivoting the cutting tool 1026 within the cutter guide 1010, a user can dissect or resect the bone 1304 in the path of the cutting section 1222 of the cutting tool 1026 between the first bone attachment feature 1006 and the second bone attachment feature 1008.

FIG. 13B is a side view of the resection guide, according to one embodiment, in another pivot position. With the cutter guide 1010 in the position illustrated in FIG. 13B, a user may apply an effort force ($F_E$) to the handle 1004 clockwise in direction 1030 (e.g., dorsally) and the lever pivots about pivot axis 1014. As the cutter guide 1010 pivots about the pivot axis 1014, the distal end of the cutting tool 1026 moves clockwise in direction 1030 (e.g., dorsally) and removes parts of a bone 1304.

Figure 14A:
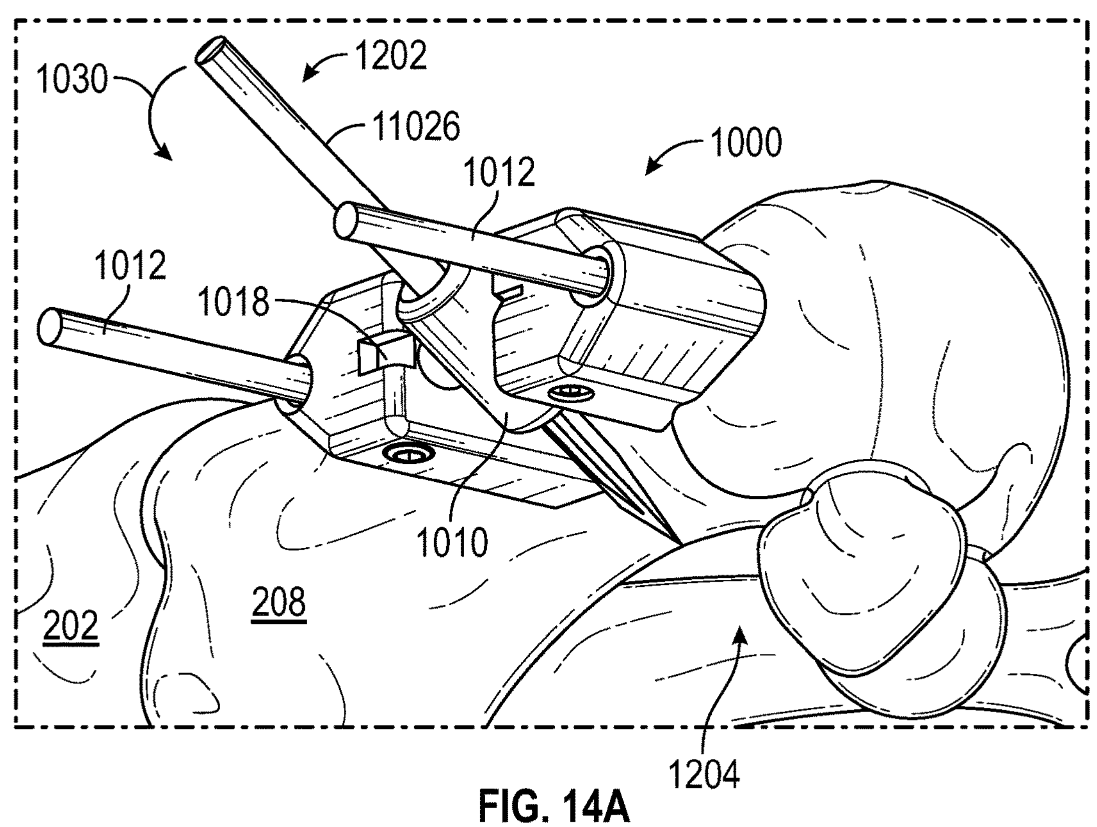
FIG. 14A is a perspective view of a resection guide in one example pivot position and secured to a bone.
Figure 14B:
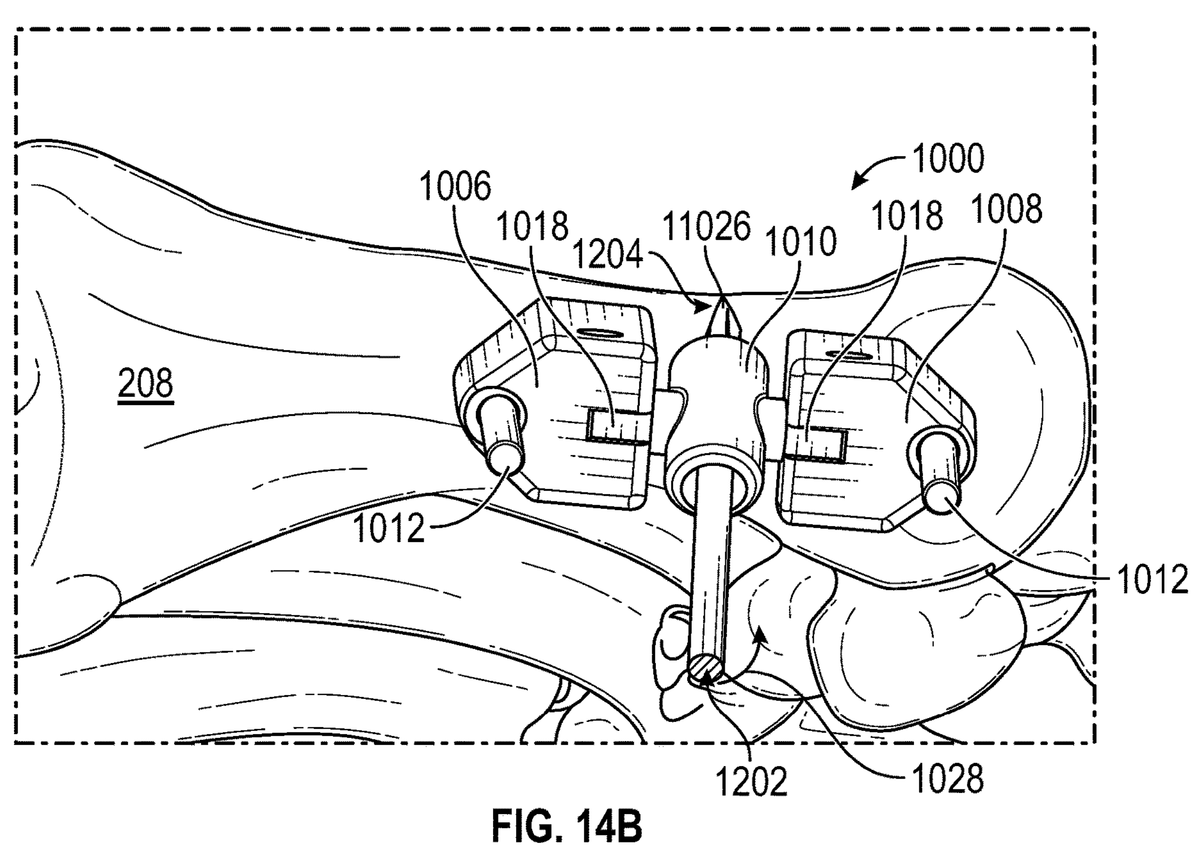
FIG. 14B is a perspective view of a resection guide in another example pivot position and secured to a bone.

FIG. 14A is a perspective view of a resection guide in one example pivot position and secured to a bone. FIG. 14A illustrates the osteotomy system 1000 deployed on a medial side and towards a distal end of the first metatarsal 208. In the illustrated embodiment, the cutting tool 1026 is deployed in the cutter guide 1010 and the distal end 1204 is near the plantar cortex of the first metatarsal 208. As a user moves the proximal end 1202 plantarly in direction 1030, the distal end 1204 moves dorsally and contacts and begins cutting the first metatarsal 208. FIG. 14B is a perspective view of a resection guide in another example pivot position and secured to a bone. In the illustrated embodiment, the cutting tool 1026 is deployed in the cutter guide 1010 and the distal end 1204 is approaching the dorsal cortex of the first metatarsal 208. As a user moves the proximal end 1202 plantarly in direction 1028, the distal end 1204 moves plantarly and contacts and begins cutting the first metatarsal 208.

Figures 15A, 15B, 15C, 15D:
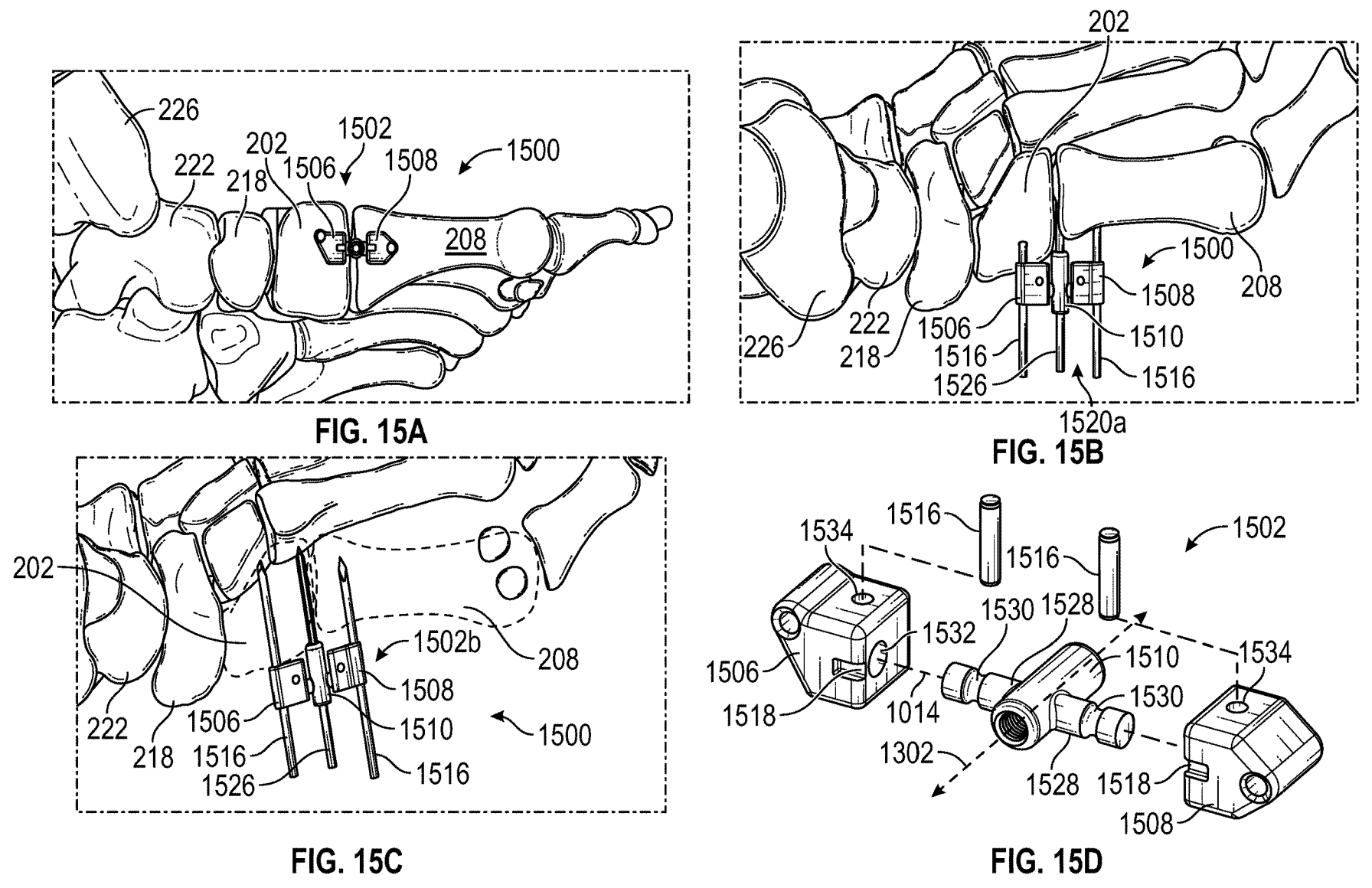

FIGS. 15A-15D illustrate views of an example pivot resection guide, according to one embodiment. FIG. 15A illustrates an alternative embodiment of an osteotomy system 1500 for a Lapidus surgical procedure of a foot. Specifically, the surgical procedure is a minimally invasive procedure Lapidus procedure. FIGS. 15A-15D illustrate views of an alternative embodiment of an osteotomy system 1000. The pivoting resection guide 1502 may have many structures, features, and functions, operations, and configuration similar or identical to those of the pivoting resection guide 1002 described in relation to FIGS. 10A-14B, like parts are identified with the same or similarly numbered reference numerals. Accordingly, the osteotomy system 1500 may include a pivoting resection guide 1502 that includes a first bone attachment feature 1506 and a second bone attachment feature 1508 with a cutter guide 1510 between them that is configured to accept a cutting tool 1526. As with the pivoting resection guide 1002, the first bone attachment feature 1506 and/or second bone attachment feature 1508 may include holes configured to receive fasteners 1516. The cutter guide 1510 is configured to receive a cutting tool 1526 that will perform the resection or dissection.

In one embodiment, the pivoting resection guide 1502 may include a single first bone attachment feature 1506 that enables the pivoting resection guide 1502 to pivot about a long axis of a single fastener deployed within the first bone attachment feature 1506. Such an embodiment may be used to enable a cutter tool to form an arc shaped resection about the single fastener deployed within the first bone attachment feature 1506.

FIG. 15B illustrates a pivoting resection guide 1502*a* positioned for resecting a first bone and FIG. 15C illustrates a pivoting resection guide 1502*b* positioned for resecting a second bone. In certain embodiments, the pivoting resection guide 1502*a* and pivoting resection guide 1502*b* may differ from each other in order to make a desired resection at a desired angle relative to one or more planes of a foot and/or axis of a toe or joint. In FIG. 15B, the pivoting resection guide 1502*a* is configured to resect a proximal end of a first metatarsal 208 and at a predetermined angle that may be patient-specific. For example, the cutter guide 1510 may pivot about a pivot axis 1014 (See FIG. 15D) that is perpendicular to a longitudinal axis 1302 of the cutter guide 1510 and the cutting tool 1526 deployed within the cutter guide 1510. The pivoting resection guide 1502*a* may be configured such that the longitudinal axis 1302 is perpendicular to a long axis of the first metatarsal 208.

Referring to FIG. 15C, in one embodiment, in contrast, the pivoting resection guide 1502*b* may be configured to resect a distal end (e.g., an articular surface) of the medial cuneiform 202 at an angle relative to a long axis of the first metatarsal 208 and/or one or more planes of the foot such that an orientation of first toe changes to a corrected position when the resected first metatarsal 208 is fused with the medial cuneiform 202. Consequently, the cutter guide 1510 may extend from the first bone attachment feature 1506 in a direction and at an orientation such that pivoting the cutter guide 1510 about the pivot axis 1014 will result in resection of the medial cuneiform 202 at a desired angle. In one embodiment, the angle of the resection is in a sagittal plane and a transverse plane of the foot. Advantageously, both the pivoting resection guide 1502*a* and the pivoting resection guide 1502*b* may remain on the surface of the skin of the foot while anchored in position. The cutting tool 1526 may enter through a small poke incision and the resection may be conducted percutaneously. In this manner, a Lapidus procedure on a TMT joint may be minimally invasive.

FIG. 15D illustrates one example of a pivoting resection guide 1502 in an exploded view. In this embodiment, the cutter guide 1510 may have a barrel shape that includes two opposing arms 1528. One or more of the arms 1528 may include a recess or groove 1530. When assembled, an arm 1528 may fit within opening 1532 of the first bone attachment feature 1506 and/or second bone attachment feature 1508. The pivoting resection guide 1502 includes one or more fasteners 1516 in the form of pins that fit within opening 1534. The fasteners 1516 is configured to slide within the opening 1534 and the fasteners 1516 fits within the groove 1530 to provide an interference fit and lock the arms 1528 within the opening 1532. In one embodiment, the cutter guide 1510 includes an opening that extends from one end to the other end. The opening may include internal threads configured to engage threads of a handle (not shown in FIG. 15D).

In one embodiment, the design of the pivoting resection guide 1502 enables faster and more efficient fabrication of the pivoting resection guide 1502. For example, because the parts of the pivoting resection guide 1502 will be fit together when assembled, the fabrication of the first bone attachment feature 1506, the second bone attachment feature 1508, and the cutter guide 1510 can be made in a single session. For example, with an additive manufacturing tool such as a 3D printer, each of these parts can be fabricated in one session with proper clearances and separation between the parts. This can greatly reduce fabrication time.

Figure 16A:
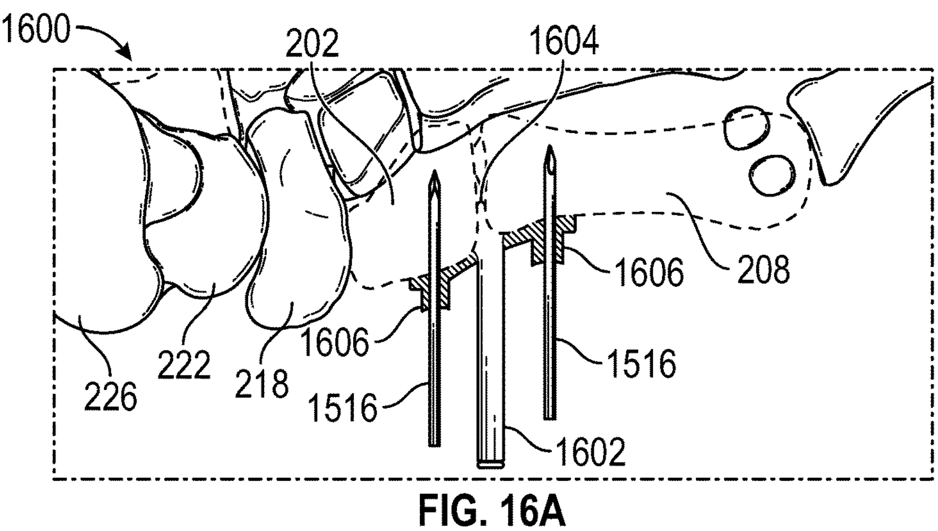
FIG. 16A-16C illustrate views in relation to a method for performing an osteotomy using an example pivot resection guide.
Figure 16B:
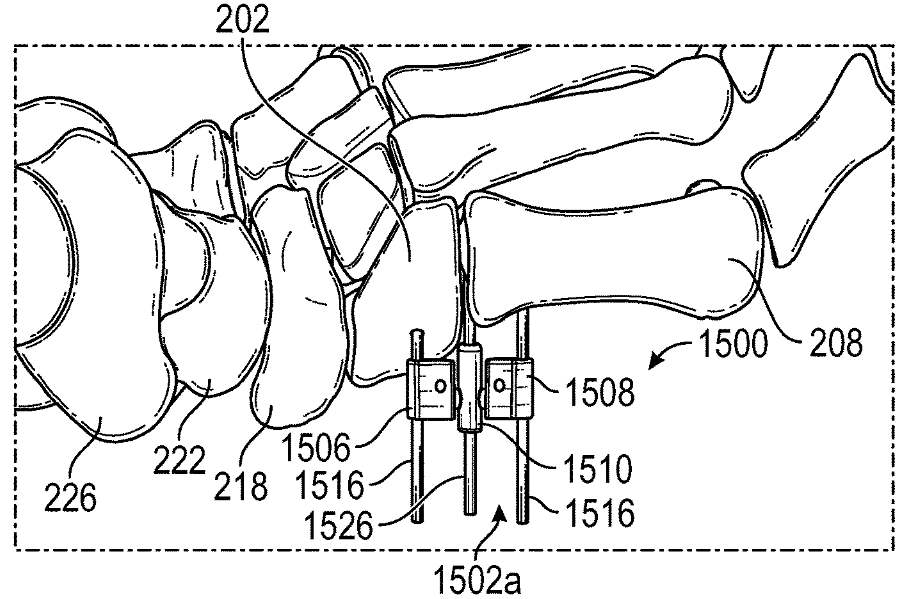
Figure 16C:
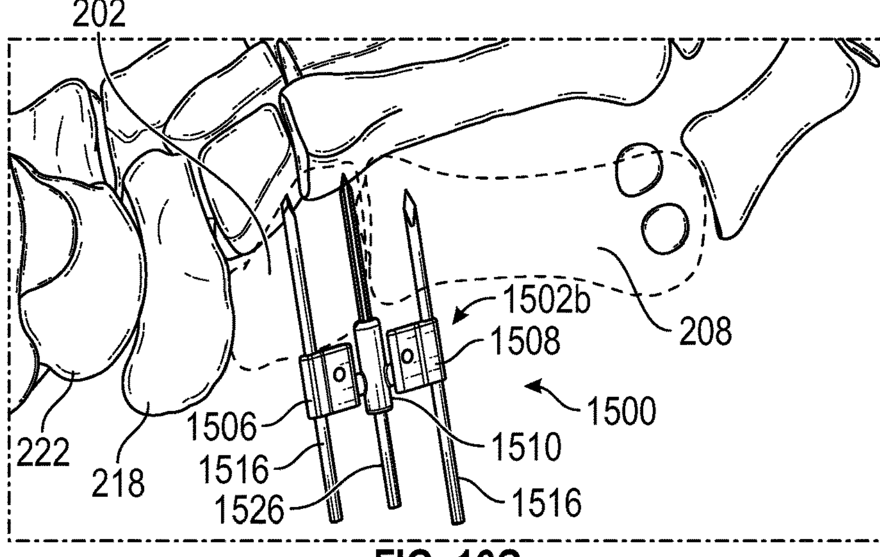

FIG. 16A-16C illustrate views a method 1600 for performing an osteotomy using an example pivot resection guide that includes a pin positioner 1602 and one or more pivoting resection guides 1502*a,b*. First, a surgeon may make a pock hole or stab incision in the skin at a TMT joint. Next, a surgeon inserts a probe 1604 at a distal end of the pin positioner 1602. The probe 1604 may be configured to register with landmarks on, around, or in the TMT joint. In one embodiment, the probe 1604 includes patient-specific features and/or surfaces to facilitate positioning the probe 1604 within or on the TMT in a desired position. For example, the probe 1604 may include one or more surfaces that are contoured to engage inverse but corresponding surfaces of one or more bones or openings within a TMT joint. In certain embodiments, a surgeon moves the pin positioner 1602 until the probe 1604 seats in a desired position within the TMT. A surgeon may be able to feel when the pin positioner 1602 moves to the desired position and registers with the bone(s) and/or joint.

In one embodiment, the pin positioner 1602 includes one or more arms 1606 that include openings for placement and/or orientation of pins or fasteners 1516. The arms 1606 can pass through an incision in the skin and rest on one or more bones of the patient. In such an embodiment, the arms 1606 may include a bone contacting surfaces that is a bone engagement surface.

In another embodiment, the arms 1606 may remain above a skin surface as the probe 1604 enters and/or contacts a joint. In one embodiment, a patient facing surface of the arms 1606 may register with skin of the patient.

With the pin positioner 1602 in a desired position, the surgeon deploys one or more fasteners 1516 through openings in the arms 1606. These fasteners 1516 serve as anchors for positioning one or more pivoting resection guides 1502. In the illustrated embodiment, the fasteners 1516 may be inserted perpendicular to a long axis of the first metatarsal 208. One fastener 1516 is anchored in the medial cuneiform 202 and the other in the first metatarsal 208.

Next, a surgeon slides a first pivoting resection guide 1502*a* over the fasteners 1516 and down against the skin. (See FIG. 16B) Next, the surgeon resects a bone aligned with a longitudinal axis 1302 of the cutting tool 1526 (e.g., the first metatarsal 208). In this manner, a cut perpendicular to the long axis of the first metatarsal 208 is made.

Next, a surgeon may remove the proximal pin (e.g., the fastener 1516 anchored in the medial cuneiform 202) and remove the pivoting resection guide 1502*a*. The distal fastener 1516 can remain in the first metatarsal 208.

There are many ways to make cuts of the medial cuneiform 202 and the first metatarsal 208 to produce a correction. In one embodiment, the first metatarsal 208 can be cut perpendicular to the long axis of the first metatarsal 208 and the cut of the medial cuneiform 202 can be angled in one or more planes. In another embodiment, the medial cuneiform 202 can be cut perpendicular to a long axis of a toe (e.g. a desired corrected position of the first metatarsal 208) of the patient and the cut of the first metatarsal 208 can be angled in one or more planes. Alternatively, or in addition, both a cut of the first metatarsal 208 and the medial cuneiform 202 may be angled in one or more planes such that when both bones are fused together at the newly formed cut faces a desired orientation of the bones is achieved.

Those of skill in the art will appreciate that use of the osteotomy system 1500 can be done in a variety of ways to accomplish the desired correction cuts of the medial cuneiform 202 and the first metatarsal 208. For example, the angle and orientation of the cutter guide 1510 in relation to the first bone attachment feature 1506 or second bone attachment feature 1508 can be used and configured to produce an angle in the bone(s) that will provide a desired correction. In such an embodiment, one or more arms 1528 may enter the openings of the first bone attachment feature 1506 and/or second bone attachment feature 1508 at an angle that is not 90 degrees.

Alternatively, the holes of the first bone attachment feature 1506 and/or second bone attachment feature 1508 can engage the fasteners 1516 at an angle and/or orientation that will cause the cutting tool 1526 to resect a bone at a desired angle. FIGS. 16B and 16C illustrate such an embodiment. Fastener 1516 may enter the medial cuneiform 202 at an angle different a fastener 1516 in a first metatarsal 208, such that cutting tool 1526 will resect the medial cuneiform 202 at an angle within one or more planes such that joining the medial cuneiform 202 and the first metatarsal 208 will provide a desired toe orientation correction.

Continuing with the method 1600, next a surgeon may deploy a fastener 1516 into the medial cuneiform 202 at an angle and orientation other than perpendicular to a surface of the bone. Next, a surgeon slides a second pivoting resection guide 1502*b* over the deployed fasteners (e.g., fastener 1516 and fastener 1516). Next, the surgeon deploys the cutting tool 1526 and resects the medial cuneiform 202. Finally, the surgeon brings the newly cut face of the first metatarsal 208 against the medial cuneiform 202 and fixates the two together for subsequent healing and recovery. In certain embodiments, the surgeon may rotate the first metatarsal 208 prior to fixation to further provide desired correction. Then method 1600 ends. Advantageously, the method 1600 can provide a minimally invasive procedure where the arms 1606 of the pin positioner 1602 remain above the skin. In such an embodiment, the procedure may be performed using three small incisions.

Figure 17A:
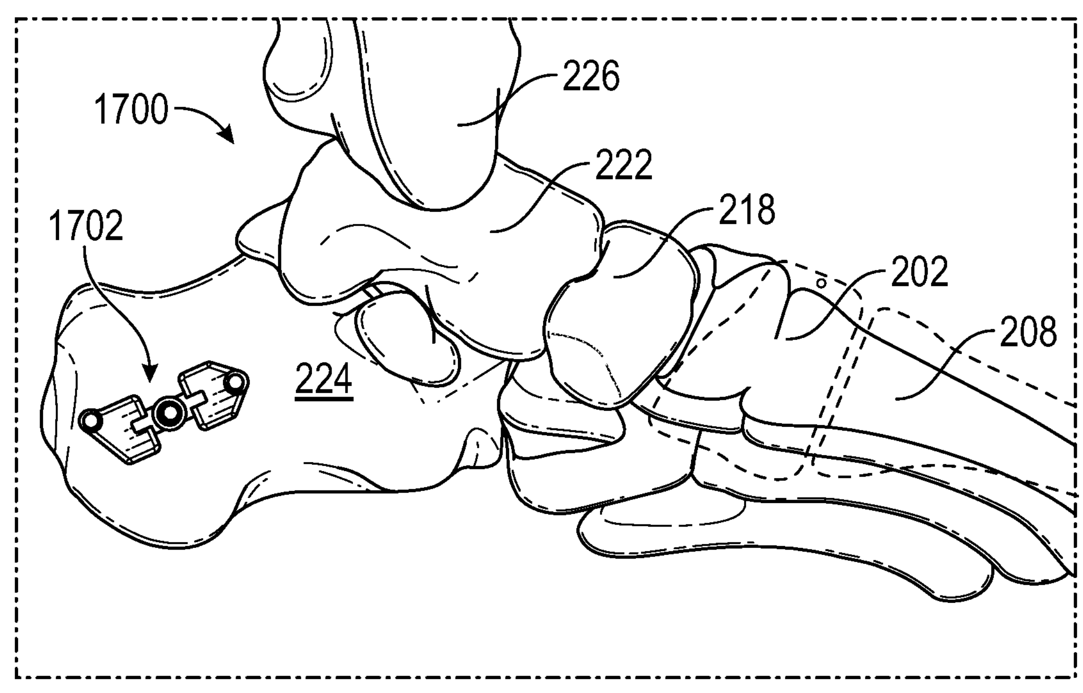
FIGS. 17A-17B illustrate views performing an osteotomy using an example pivot resection guide on a calcaneus bone, according to one embodiment.
Figure 17B:
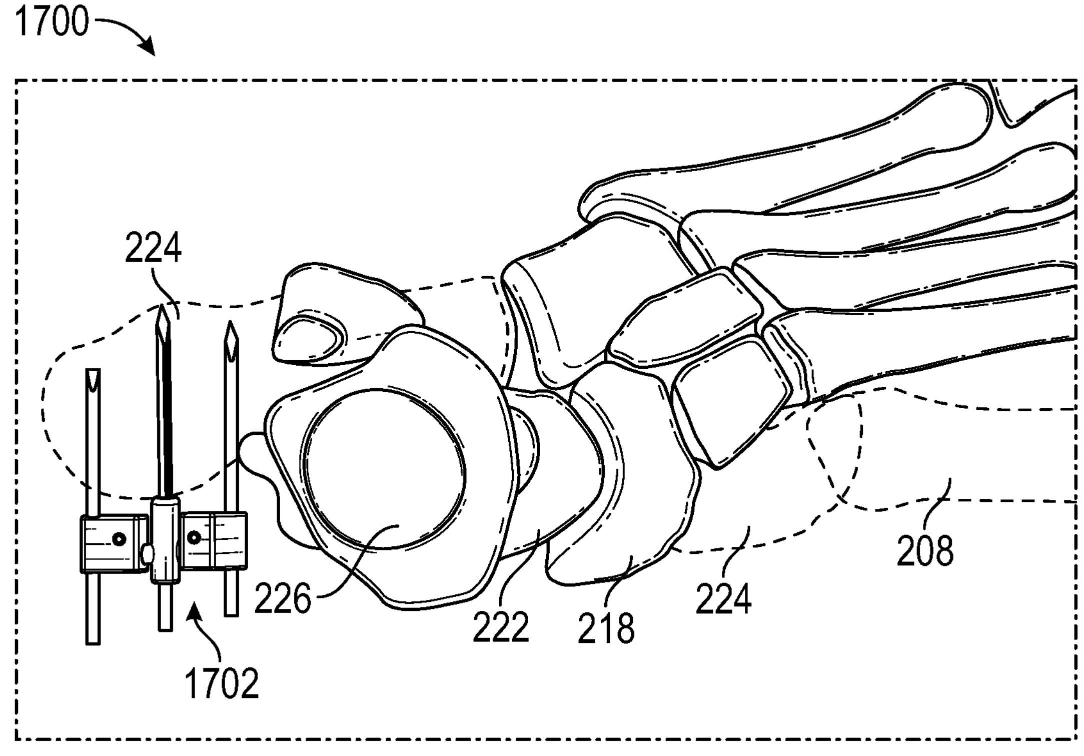

FIGS. 17A-17B illustrate views performing an osteotomy using an example pivot resection guide on a calcaneus bone, according to one embodiment. Those of skill in the art will appreciate that the example pivoting resection guide 1002 and/or pivoting resection guide 1502 are simply examples and that a pivoting resection guide can be used for a variety of osteotomies on a variety of bones. As another example, a pivoting resection guide can be used for resection of a calcaneus 224. Alternatively, or in addition, pivoting resection guide can be used for resection of a femur, a humerus, a radius, an ulna, a phalange, a phalanx, or other bone of a person or animal. FIG. 17A illustrates an osteotomy system 1700 that includes a pivoting resection guide 1702 for use in resecting a calcaneus 224. In one embodiment, the pivoting resection guide 1702 may include patient-specific features. In another embodiment, the pivoting resection guide 1702 does not include patient-specific features. FIG. 17B illustrates superior perspective view of an osteotomy system 1700 that includes a pivoting resection guide 1702 for use in resecting a calcaneus 224. The calcaneus 224 is shown in transparent form.

Figure 18A:
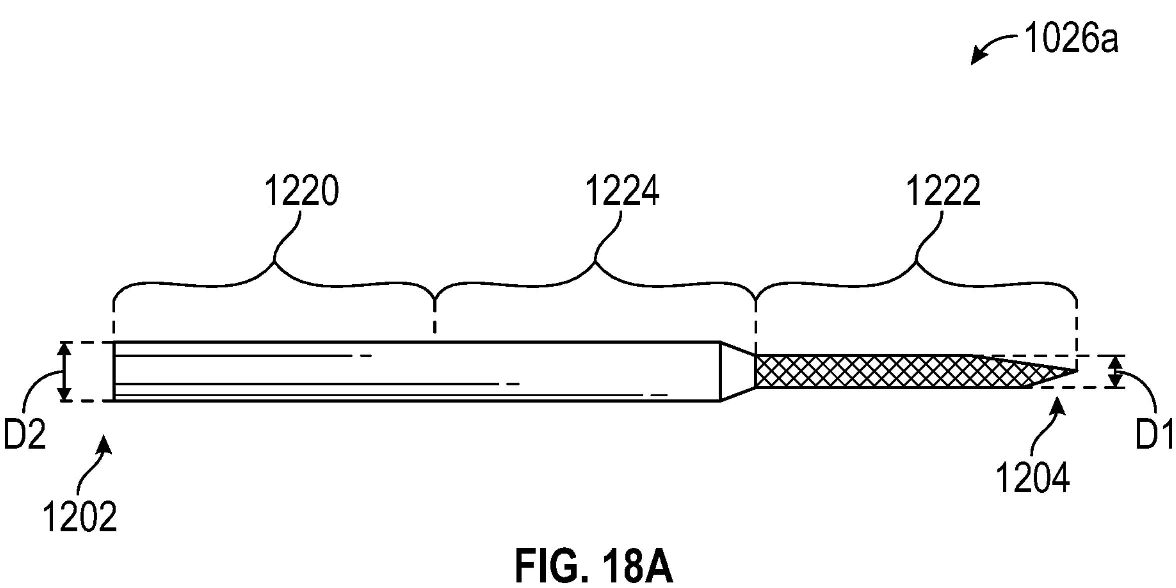
FIGS. 18A-18B illustrate views of example cutting tools that can be used, according to different embodiments.
Figure 18B:
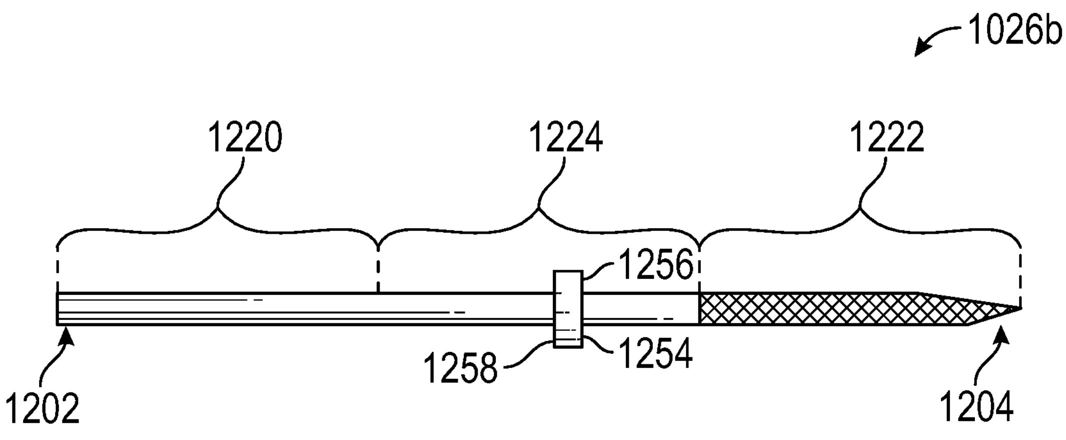

FIGS. 18A-18C illustrate views of example cutting tools that can be used, according to different embodiments. In one embodiment, the cutting tool 1026*a* has an elongate body with a round cross section. The drive section 1220 is near the proximal end 1202 and is configured to couple to a driver that rotates the cutting tool 1026. The guide section 1224 engages with the pivoting resection guide 1002 and guides the cutting tool 1026 during the creation of an osteotomy. The cutting section 1222 is near the distal end 1204. The cutting section 1222 is the part that resects/dissects the bone to form an osteotomy. In one embodiment, the cutting section 1222 includes a set of flutes or grooves that include sharp edges configured to cut and resect hard tissue and/or soft tissue.

FIG. 18A illustrates a cutting tool **1026*a* that is configured to mitigate, eliminate, and/or avoid contact between the cutting section 1222 and the cutter guide 1010 (e.g., the walls of opening 1206). In the illustrated embodiment, the cutting tool 1026*a* includes a cutting section 1222 with a first diameter D1 and the guide section 1224 has a second diameter D2. In one embodiment, the first diameter D1 is smaller than the second diameter D2. The size of the second diameter D2 may be just large enough to permit a close fit between a section of the cutting tool 1026 with the second diameter D2 (e.g., the guide section 1224) and the wall of the opening 1206 of the cutter guide 1010. In this manner, the cutting section 1222 substantially avoids contact with the wall of the opening 1206 of the cutter guide 1010**.

FIG. 18B illustrates an alternative embodiment of cutting tool **1026*b* that is configured to mitigate, eliminate, and/or avoid contact between the cutting section 1222 and the cutter guide 1010 (e.g., the walls of opening 1206). In the illustrated embodiment, the cutting tool 1026*b* includes collar 1254 between the cutting section 1222 and the drive section 1220. As with the larger diameter D2, the collar has a diameter that permits a close fit between the collar 1254 and the wall of the opening 1206 of the cutter guide 1010. In this manner, the cutting section 1222 substantially avoids contact with the wall of the opening 1206 of the cutter guide 1010**.

Referring now to FIGS. 18A and 18B, in certain embodiments, a cutting tool 1026 can be configured to control a depth that the cutting tool 1026 can be inserted into the opening 1206. In one embodiment, a section along the length of the cutting tool 1026 may start out with a diameter D2 which fits within the cutting tool 1026 and gradually increase at some point between the guide section 1224 and the proximal end 1202 such that at some point the cutting tool 1026 can move no further into the opening 1206. In this manner, the depth of insertion of the cutting tool 1026 can be controlled. In certain embodiments, this depth may be patient-specific and/or may be predetermined or requested by a surgeon for a particular surgical procedure.

Similarly, referring to FIG. 18B, the collar 1254 may be configured such that a distal end 1256 closer to the distal end 1204 of the cutting tool 1026 has a small enough diameter to fit within the opening 1206 and a proximal end 1258 closer to the proximal end 1202 has a larger diameter that will not fit within the opening 1206. The length between the distal end 1256 and the proximal end 1258 can be relatively short or can be longer. In certain embodiments, this length may be patient-specific. In this manner, a collar 1254 can be used as a depth stop for the cutting tool 1026.

Figure 19A:
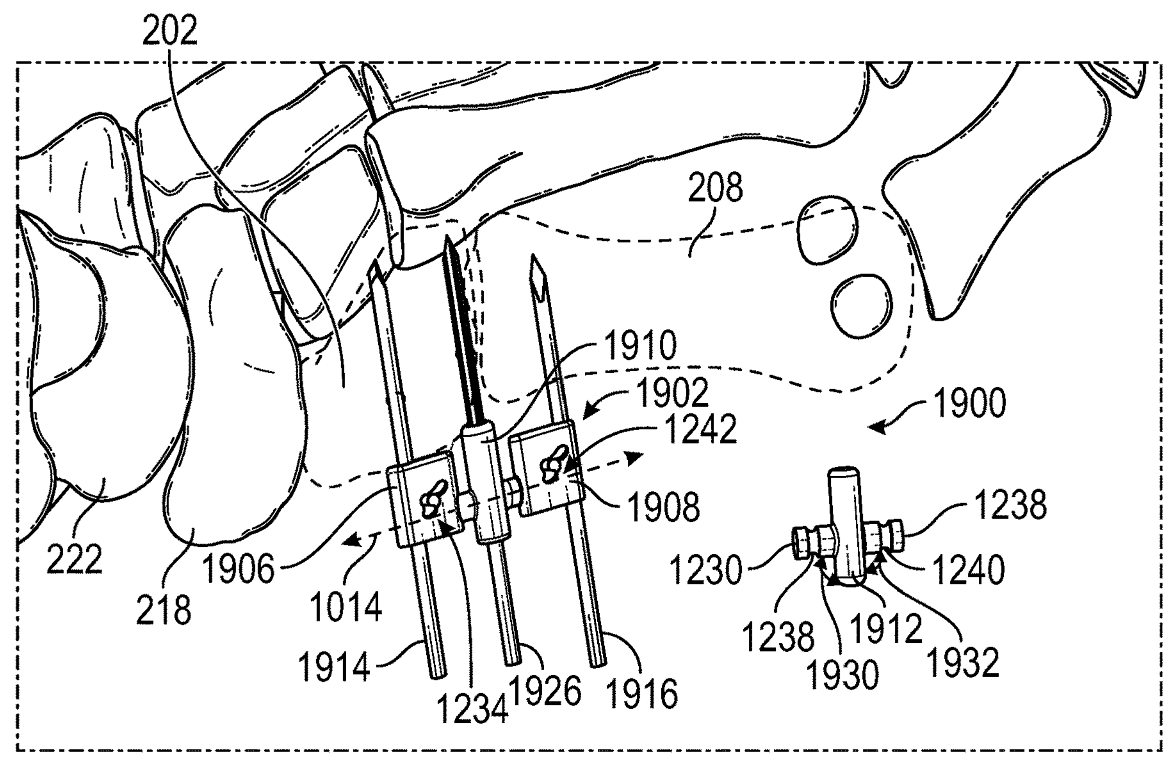
FIGS. 19A-19B illustrate views of an exemplary system, according to one embodiment.
Figure 19B:
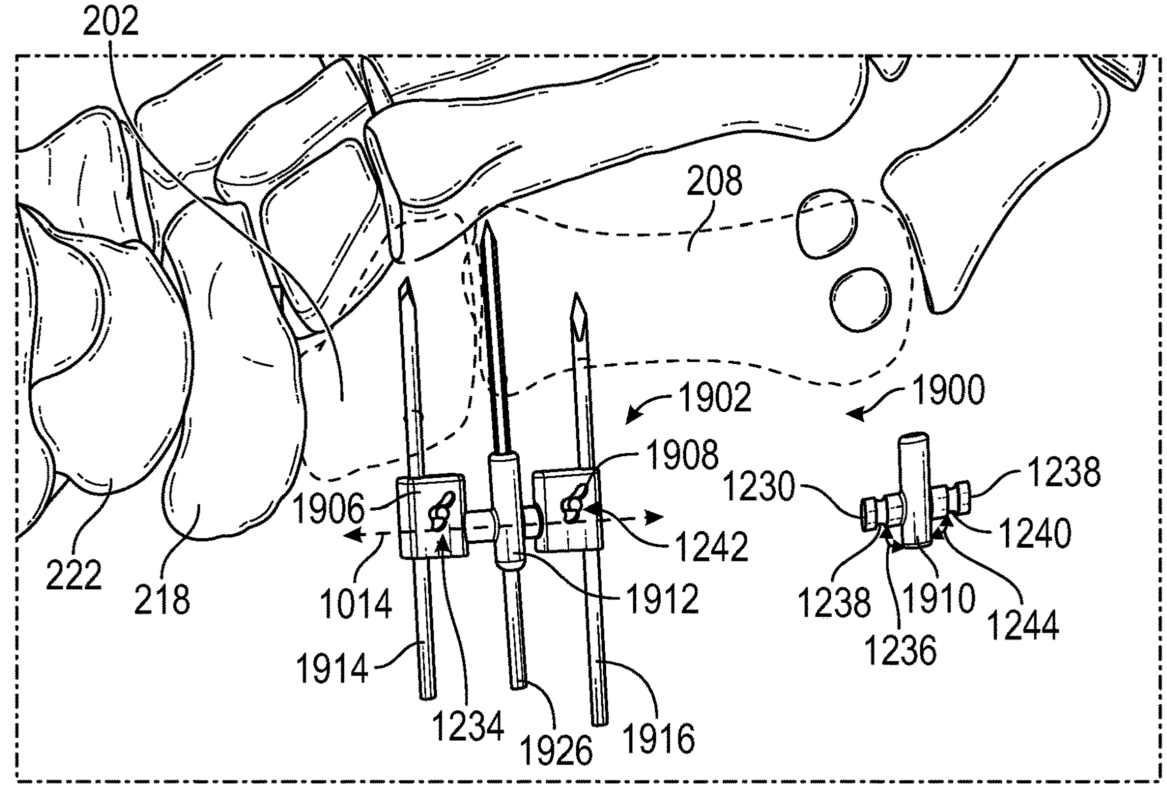

FIGS. 19A-19B illustrate views of an exemplary system 1900, according to one embodiment. FIGS. 19A-19B illustrate an alternative embodiment of an osteotomy system 1900 for a Lapidus surgical procedure of a foot. FIGS. 19A-19B illustrate views of an alternative embodiment of an osteotomy system 1000. The pivoting resection guide 1902 may have many structures, features, and functions, operations, and configuration similar or identical to those of the pivoting resection guide 1002 described in relation to FIGS. 10A-18B, like parts are identified with the same or similarly numbered reference numerals. Accordingly, the osteotomy system 1900 may include a pivoting resection guide 1902 that includes a cuneiform attachment feature 1906 and a first metatarsal attachment feature 1908.

The osteotomy system 1900 includes both a cuneiform cutter guide 1910 and a first metatarsal cutter guide 1912. Both the cuneiform cutter guide 1910 and the first metatarsal cutter guide 1912 are configured to couple to the cuneiform cutter guide 1910 or the first metatarsal cutter guide 1912 between the cuneiform attachment feature 1906 and a first metatarsal attachment feature 1908. In addition, each of the cuneiform cutter guide 1910 and a first metatarsal cutter guide 1912 may be configured to accept a cutting tool 1926. Alternatively, or in addition, each of the cuneiform cutter guide 1910 and a first metatarsal cutter guide 1912 may be configured to accept a different cutting tool 1926.

As with the pivoting resection guide 1002, the cuneiform attachment feature 1906 and/or first metatarsal attachment feature 1908, in certain embodiments, include holes configured to receive fasteners. The cuneiform attachment feature 1906 is configured to receive a cuneiform fastener 1914 and the first metatarsal attachment feature 1908 is configured to receive a metatarsal fastener 1916. The cuneiform fastener 1914 is configured to engage a medial cuneiform 202. The metatarsal fastener 1916 is configured to engage a first metatarsal 208.

Advantageously, the pivoting resection guide 1902 is configured to resect both the medial cuneiform 202 and the first metatarsal 208. The cuneiform cutter guide 1910 is configured to be removably coupled between the cuneiform attachment feature 1906 and the first metatarsal attachment feature 1908. The cuneiform cutter guide 1910 is configured to guide a cutting tool, such as cutting tool 1926, as the cutter guide pivots about a pivot axis 1014 that extends between the cuneiform attachment feature 1906 and the first metatarsal attachment feature 1908. Similarly, the first metatarsal cutter guide 1912 is configured to be removably coupled between the cuneiform attachment feature 1906 and the first metatarsal attachment feature 1908. The first metatarsal cutter guide 1912 is configured to guide a cutting tool, such as cutting tool 1926, as the first metatarsal cutter guide 1912 pivots about the pivot axis 1014 that extends between the cuneiform attachment feature 1906 and the first metatarsal attachment feature 1908.

In the illustrated embodiment, the cutting tool 1926 has an elongate body with a proximal end and distal end. The cutting tool 1926 also includes a drive section 1220 near the proximal end, a cutting section 1222 near the distal end, and guide section 1224 between the drive section 1220 and the cutting section 1222. The cutting tool 1926 is configured to be deployed within an opening (e.g., opening 1206) in one of the cuneiform cutter guide 1910 and the first metatarsal cutter guide 1912.

In one embodiment, the osteotomy system 1900 may also include a handle (not shown in FIG. 19). The handle may be substantially similar to the handle 1004 described herein. In such an embodiment, the handle may include a distal handle end that includes a handle coupler (e.g., handle coupler 1212). The handle coupler 1212 is configured to engage with one of the cuneiform cutter guide 1910 and the first metatarsal cutter guide 1912. The handle also includes a proximal handle end opposite the distal handle end and an opening that extends from the proximal handle end to the distal handle end and is coaxial with a longitudinal axis of the handle.

In embodiments of the osteotomy system 1900 that include a handle, as well as those that do not include a handle, the pivoting resection guide 1902 combines the cutting tool 1926, a cutter guide (either cuneiform cutter guide 1910 or first metatarsal cutter guide 1912) and the cuneiform attachment feature 1906 and first metatarsal attachment feature 1908 to fora first-class lever that magnifies a load force applied to a bone in contact with the cutting tool 1926 near the distal end of the cutting tool 1926 based on an effort force applied by a user near a proximal end of the cutting tool 1926.

Where the osteotomy system 1900 includes a handle, the handle is configured to pass the cutting tool through the opening and couple to one of the cuneiform cutter guide 1906 and the first metatarsal cutter guide 1908 to form the first-class lever. In such an embodiment, the effort force may be applied by a user near the proximal end of the handle.

Referring now to FIGS. 19A, 19B, and 12A, in the illustrated embodiment, the cuneiform cutter guide 1910 and first metatarsal cutter guide 1912 have many, if not all, of the same or similar structures, features, and functions, operations, and configuration similar or identical to those of the example cutter guide 1010 described in relation to FIG. 12A, like parts are identified with the same or similarly numbered reference numerals.

Referring now to FIG. 19B, the cuneiform cutter guide 1910 is illustrated decoupled from the pivoting resection guide 1902. Suppose the cuneiform cutter guide 1910 has the same configuration as cutter guide 1010. Accordingly, the cuneiform cutter guide 1910 includes a proximal arm 1230 that extends from a first side of the cuneiform cutter guide 1910 at a first arm angle 1236 towards the cuneiform attachment feature 1906 and a proximal arm groove 1232 toward a distal end of the proximal arm 1230. The cuneiform cutter guide 1910 also includes a proximal arm retainer 1234 (which in the illustrated embodiment is a toolless coupler, such as a thumbscrew). Notably the proximal arm retainer 1234 is configured to be operated by a user to releasably engage with the proximal arm 1230.

Similarly, the cuneiform cutter guide 1910 includes a distal arm 1238 that extends from a second side of the cuneiform cutter guide 1910 at a second arm angle 1244 towards the first metatarsal attachment feature 1908 and a distal arm groove 1240 toward a distal end of the distal arm 1238. The cuneiform cutter guide 1910 also includes a distal arm retainer 1242 (which in the illustrated embodiment is a toolless coupler, such as a thumbscrew). Notably the distal arm retainer 1242 is configured to be operated by a user to releasably engage with the distal arm 1238.

The cuneiform cutter guide 1910 is configured to guide the cutting tool 1926 for resection/dissection of the medial cuneiform 202. Those of skill in the art will appreciate that various aspects of the cuneiform cutter guide 1910 can be defined such that operation of the cutting tool 1926 by way of cuneiform cutter guide 1910 forms an osteotomy of a predefined trajectory in the medial cuneiform 202 of the patient. Examples of these aspects include but are not limited to a length of the proximal arm 1230, a length of the distal arm 1238, a size of the first arm angle 1236, a size of the second arm angle 1244 and the like.

Referring now to FIG. 19A, the first metatarsal cutter guide 1912 is illustrated decoupled from the pivoting resection guide 1902. Suppose the first metatarsal cutter guide 1912 has almost the same configuration as cutter guide 1010. Accordingly, suppose the first metatarsal cutter guide 1912 includes a proximal arm 1230 that extends from a first side of the first metatarsal cutter guide 1912 and a proximal arm groove 1232 toward a distal end of the proximal arm 1230. The first metatarsal cutter guide 1912 also includes a proximal arm retainer 1234 (which in the illustrated embodiment is a toolless coupler, such as a thumbscrew). Notably the proximal arm retainer 1234 is configured to be operated by a user to releasably engage with the proximal arm 1230.

Similarly, the first metatarsal cutter guide 1912 includes a distal arm 1238 that extends from a second side of the cuneiform cutter guide 1910 and a distal arm groove 1240 toward a distal end of the distal arm 1238. The first metatarsal cutter guide 1912 also includes a distal arm retainer 1242 (which in the illustrated embodiment is a toolless coupler, such as a thumbscrew). Notably the distal arm retainer 1242 is configured to be operated by a user to releasably engage with the distal arm 1238.

The first metatarsal cutter guide 1912 is configured to guide the cutting tool 1926 for resection/dissection of the first metatarsal 208. Those of skill in the art will appreciate that varies aspects of the first metatarsal cutter guide 1912 can be defined such that operation of the cutting tool 1926 by way of first metatarsal cutter guide 1912 forms an osteotomy of a predefined trajectory in the first metatarsal 208 of the patient. Examples of these aspects include but are not limited to a length of the proximal arm 1230, a length of the distal arm 1238, a size of the first arm angle 1236, a size of the second arm angle 1244 and the like.

In the illustrated embodiment, the cuneiform cutter guide 1910 and the first metatarsal cutter guide 1912 may differ with respect to the first arm angle 1236 and the second arm angle 1244. On the cuneiform cutter guide 1910 the first arm angle 1236 and the second arm angle 1244 may be right angles such that the operation of the pivoting resection guide 1902 forms a straight cut parallel to the cuneiform fastener 1914 and the metatarsal fastener 1916. However, the first metatarsal cutter guide 1912 may include a proximal arm 1230 that extends from the first metatarsal cutter guide 1912 toward the cuneiform attachment feature 1906 at a first arm angle 1930 and a distal arm 1238 that extends from the first metatarsal cutter guide 1912 toward the cuneiform attachment feature 1906 at a second arm angle 1932. The first arm angle 1930 may differ from the first arm angle 1236 and the second arm angle 1932 may differ from the second arm angle 1244. The different angles for the first arm angle 1930 and second arm angle 1932 may be defined such that a distal end of the first metatarsal cutter guide 1912 points more distal than the distal end of the cuneiform cutter guide 1910. In this manner, the angles for the first arm angle 1930 and second arm angle 1932 can be defined to direct the cutting tool 1926 for resection/dissection of the first metatarsal 208.

FIG. 19A illustrates the pivoting resection guide 1902 with the cuneiform cutter guide 1910 coupled for resecting/dissecting the medial cuneiform 202 and the first metatarsal cutter guide 1912 is shown, decoupled, for comparison. FIG. 19B illustrates the pivoting resection guide 1902 with the first metatarsal cutter guide 1912 coupled for resecting/dissecting the first metatarsal 208 and the cuneiform cutter guide 1910 is shown, decoupled, for comparison.

Advantageously, a user may use the osteotomy system 1900 to resect/dissect both a medial cuneiform 202 and a first metatarsal 208 using the same system. To form an osteotomy on the medial cuneiform 202 the user uses the cuneiform cutter guide 1910 and to form an osteotomy on the first metatarsal 208 the user uses the first metatarsal cutter guide 1912. FIG. 19A illustrates an example of the osteotomy system 1900 with the cuneiform cutter guide 1910 removably coupled between the cuneiform attachment feature 1906 and the first metatarsal attachment feature 1908. Initially, a user may deploy the pivoting resection guide 1902 by securing the cuneiform attachment feature 1906 using the cuneiform fastener 1914 to the medial cuneiform 202 and securing the first metatarsal attachment feature 1908 using the metatarsal fastener 1916 to the first metatarsal 208.

Initially, the cuneiform cutter guide 1910 is coupled between the cuneiform attachment feature 1906 and the first metatarsal attachment feature 1908. Next, a user may insert the cutting tool 1926 and resect/dissect a distal portion of the medial cuneiform 202. Advantageously, the cuneiform cutter guide 1910 is configured for a resection/dissection of the distal portion of the medial cuneiform 202.

Next, a user may decouple the cuneiform cutter guide 1910 from the cuneiform attachment feature 1906 and the first metatarsal attachment feature 1908 after removing the cutting tool 1926. In one embodiment, the first coupler 1118 and the second coupler 1148 may include a pair of toolless couplers. In one embodiment, the toolless couplers may be a set of fasteners that a user or other operator can tighten and/or loosen with their fingers. Examples of toolless couplers include, but are not limited to thumbscrews, set screws, levers, buttons, and the like.

With the cuneiform cutter guide 1910 decoupled, the user may couple the first metatarsal cutter guide 1912 to the cuneiform attachment feature 1906 and the first metatarsal attachment feature 1908. In the illustrated embodiment, the user may use the same toolless couplers to couple the first metatarsal cutter guide 1912 to both the cuneiform attachment feature 1906 and the first metatarsal attachment feature 1908.

At this stage, the same pivoting resection guide 1902 is now configured to resect/dissect the first metatarsal 208. This change in configuration may be due to differences between the cuneiform cutter guide 1910 and the first metatarsal cutter guide 1912. Next, the user inserts the cutting tool 1926 into the first metatarsal cutter guide 1912 and resects/dissects the first metatarsal 208 by pivoting the cutting tool 1926 plantarly and/or dorsally to sweep through the bone. At this stage, the resection/dissection of the medial cuneiform 202 and the first metatarsal 208 is complete. The user may now remove the cuneiform attachment feature 1906 and the first metatarsal attachment feature 1908 with the cutting tool 1926. The cuneiform fastener 1914 and/or metatarsal fastener 1916 may be left in the bones to be used for subsequent temporary or permanent fixation and/or fusion of the two bones.

In another example embodiment, the osteotomy system may include two pivoting resection guides, one configured for dissecting/resecting a first bone and another for dissecting/resecting a second bone. In such a system, the system may include a first temporary fastener configured to engage a first bone of a patient's foot; a second temporary fastener configured to engage a second bone of a patient's foot; and a first pivoting resection guide configured to resect the first bone.

The first pivoting resection guide may include a first bone attachment feature configured to receive the first temporary fastener; a second bone attachment feature configured to receive the second temporary fastener; a cutter guide coupled between the first bone attachment feature and the second bone attachment feature, the cutter guide configured to guide a cutting tool as the cutter guide rotates about a pivot axis that extends between the first bone attachment feature and the second bone attachment feature; and a second pivoting resection guide configured to resect the second bone.

The second pivoting resection guide may include a third bone attachment feature configured to slide over the first temporary fastener; a fourth bone attachment feature configured to slide over the second temporary fastener; a cutter guide coupled between the third bone attachment feature and the fourth bone attachment feature, the cutter guide configured to guide a cutting tool as the cutter guide rotates about a pivot axis that extends between the third bone attachment feature and the fourth bone attachment feature.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. An apparatus for remediating a condition present in a patient's foot, the apparatus comprising:

- a first bone attachment feature configured to receive at least one temporary fastener configured to engage one or more bones of a patient's foot, the first bone attachment feature comprising a patient-specific bone engagement surface configured to engage a cortical bone surface of the one or more bones, the patient-specific bone engagement surface is at least partially determined based on a bone model of a patient's foot, the bone model defined based on medical imaging of the patient's foot;
- a cutter guide rotatably coupled to the first bone attachment feature about a pivot axis, the cutter guide comprising an opening configured to accept a cutting tool and guide the cutting tool through an arc as the cutter guide rotates about the pivot axis.

2. An osteotomy system for remediating a condition present in a patient's foot, the system comprising:

- a pivoting resection guide comprising:
  - a first bone attachment feature configured to receive at least one temporary fastener configured to engage one or more bones of a patient's foot;

a second bone attachment feature configured to receive at least one other temporary fastener;

a cutter guide rotatably coupled between the first bone attachment feature and the second bone attachment feature about a pivot axis, the cutter guide comprising an opening configured to accept a cutting tool and guide the cutting tool through an arc as the cutter guide rotates about the pivot axis.

3. The osteotomy system of claim 2, comprising:

a cutting tool comprising a proximal end and a distal end, the cutting tool configured to be deployed within an opening in the cutter guide;

a handle comprising:

a distal handle end comprising a handle coupler configured to engage with the cutter guide;

a proximal handle end opposite the distal handle end;

an opening that extends from the proximal handle end to the distal handle end and is coaxial with a longitudinal axis of the handle;

wherein the handle is configured to pass the cutting tool through the opening and couple to the cutter guide to form a first-class lever that magnifies a load force applied to a bone in contact with the cutting tool near the distal end of the cutting tool based on an effort force applied by a user toward the proximal handle end.

4. The osteotomy system of claim 3, wherein the pivot axis comprises a fulcrum of the first-class lever and the load force comprises the effort force multiplied by a lever arm length, the lever arm length comprising a distance between the fulcrum and a point toward the proximal handle end where the effort force is applied.

5. The osteotomy system of claim 2, wherein the first bone attachment feature comprises:

a body comprising:

a superior side;

an inferior side;

a medial side;

a lateral side;

a proximal side;

a distal side;

an opening that extends from the superior side to the inferior side, the opening configured to receive one of the one or more temporary fasteners; and a first coupler configured to engage with the cutter guide between the first bone attachment feature and the second bone attachment feature; and a first height from the superior side to the inferior side.

6. The osteotomy system of claim 5, wherein the inferior side of the first bone attachment feature comprises a bone engagement surface configured to engage a cortical bone surface of the one or more bones.

7. The osteotomy system of claim 6, wherein the bone engagement surface is at least partially determined based on a bone model of a patient's foot, the bone model defined based on medical imaging of the patient's foot.

8. The osteotomy system of claim 5, wherein the first coupler is configured to retain a pivot arm of the cutter guide and enable the cutter guide to rotate about the pivot arm.

9. The osteotomy system of claim 5, wherein the second bone attachment feature comprises:

a body comprising:

a superior side;

an inferior side;

a medial side;

a lateral side;

a proximal side;

a distal side;

an opening that extends from the superior side to the inferior side, the opening configured to receive one of the one or more temporary fasteners; and a second coupler configured to engage with the cutter guide between the first bone attachment feature and the second bone attachment feature;

a second height from the superior side to the inferior side; and wherein the first coupler, second coupler, first height, and second height correlate to define a trajectory for the cutter guide towards the one or more bones.

10. The osteotomy system of claim 9, wherein:

the first coupler engages the cutter guide at a first angle that is perpendicular to the distal side of the first bone attachment feature;

the second coupler engages the cutter guide at a second angle that is perpendicular to the distal side of the second bone attachment feature; and the first height and the second height are defined such that the trajectory of the cutter guide extends substantially perpendicular to a longitudinal axis of one of the one or more bones to be resected.

11. The osteotomy system of claim 10, wherein the first angle is not a right angle with respect to the distal side of the first bone attachment feature and the second angle is not a right angle with respect to the distal side of the second bone attachment feature and the first height and second height are defined such that the trajectory of the cutter guide extends at an angle that is not perpendicular to the longitudinal axis of one of the one or more bones to be resected.

12. The osteotomy system of claim 9, wherein the first coupler comprises:

a proximal arm that extends from a first side of the cutter guide at a first arm angle towards the first bone attachment feature;

a proximal arm groove toward a distal end of the proximal arm;

a proximal arm retainer configured to engage with a body of the first bone attachment feature and engage with the proximal arm groove to couple the proximal arm to the first bone attachment feature; and wherein the second coupler comprises:

a distal arm that extends from a second side of the cutter guide at a second arm angle towards the second bone attachment feature;

a distal arm groove toward a distal end of the distal arm;

a distal arm retainer configured to engage with a body of the second bone attachment feature and engage with the distal arm groove to couple the distal arm to the second bone attachment feature.

13. The osteotomy system of claim 3, wherein the cutting tool comprises:

a body comprising:

a drive section near the proximal end;

a cutting section near the distal end, the cutting section having a predetermined length configured to extend from one cortex of a bone to an opposite cortex of the bone when the cutting tool is used to resect the bone; and a guide section between the drive section and the cutting section.

14. The osteotomy system of claim 13, wherein the body of the cutting tool is an elongate body having a round cross section and wherein the cutting section has a first diameter and the guide section has a second diameter, the first diameter being smaller than the second diameter.

15. The osteotomy system of claim 13, wherein the cutter guide comprises an opening that extends from a proximal end of the cutter guide to a distal end of the cutter guide, the opening of the cutter guide sized and shaped to accept the cutting tool and wherein the body of the cutting tool is an elongate body having a round cross section and the cutting tool comprises a collar between the cutting section and the drive section, the collar having a diameter that permits a close fit of the collar within the opening of the cutter guide.

16. The osteotomy system of claim 3, wherein the handle coupler comprises:

a recess that extends from the distal handle end towards the proximal handle end, the recess having a cross-sectional shape and size configured to accept a proximal end of the cutter guide into the recess;

at least one arm that extends radially from the handle near the distal handle end, the at least one arm configured to engage with one of the first bone attachment feature and the second bone attachment feature.

17. An osteotomy system for remediating a bunion in a patient's foot, the system comprising:

a cuneiform fastener configured to engage a medial cuneiform of a patient's foot;

a metatarsal fastener configured to engage a first metatarsal of a patient's foot;

a pivoting resection guide configured to resect at least one of the medial cuneiform and the first metatarsal, the pivoting resection guide comprising:

a cuneiform attachment feature an opening configured to receive the cuneiform fastener;

a first metatarsal attachment feature configured to receive the metatarsal fastener;

a cuneiform cutter guide configured to be removably coupled between the cuneiform attachment feature and the first metatarsal attachment feature, the cuneiform cutter guide configured to guide a cutting tool as the cuneiform cutter guide pivots about a pivot axis that extends between the cuneiform attachment feature and the first metatarsal attachment feature;

a first metatarsal cutter guide configured to be removably coupled between the cuneiform attachment feature and the first metatarsal attachment feature, the first metatarsal cutter guide configured to guide a cutting tool as the first metatarsal cutter guide pivots about the pivot axis that extends between the cuneiform attachment feature and the first metatarsal attachment feature;

a cutting tool comprising:

an elongate body having a proximal end and a distal end;

a drive section near the proximal end of the elongate body;

a cutting section near the proximal end of the elongate body; and a guide section between the drive section and the cutting section, the cutting tool configured to be deployed within an opening in one of the cuneiform cutter guide and the first metatarsal cutter guide;

a handle comprising:

a distal handle end comprising a handle coupler configured to engage with one of the cuneiform cutter guide and the first metatarsal cutter guide;

a proximal handle end opposite the distal handle end;

an opening that extends from the proximal handle end to the distal handle end and is coaxial with a longitudinal axis of the handle; and wherein the handle is configured to pass the cutting tool through the opening and couple to one of the cuneiform cutter guide and the first metatarsal cutter guide to form a first-class lever that magnifies a load force applied to a bone in contact with the cutting tool near the distal end of the cutting tool based on an effort force applied by a user near the proximal handle end.

18. The osteotomy system of claim 17, wherein the cuneiform cutter guide comprises:

a proximal arm that extends from a first side of the cuneiform cutter guide at a first arm angle towards the cuneiform attachment feature;

a proximal arm groove toward a distal end of the proximal arm;

a proximal arm retainer configured to engage with a body of the cuneiform attachment feature and engage with the proximal arm groove to couple the proximal arm to the cuneiform attachment feature;

a distal arm that extends from a second side of the cuneiform cutter guide at a second arm angle towards the first metatarsal attachment feature;

a distal arm groove toward a distal end of the distal arm;

a distal arm retainer configured to engage with a body of the first metatarsal attachment feature and engage with the distal arm groove to couple the distal arm to the first metatarsal attachment feature; and wherein at least one of a length of the proximal arm, a length of the distal arm, a size of the first arm angle and a size of the second arm angle are defined such that operation of the cutting tool by way of the cuneiform cutter guide forms an osteotomy of a predefined trajectory in the cuneiform of the patient.

19. The osteotomy system of claim 17, wherein the first metatarsal cutter guide comprises:

a proximal arm that extends from a first side of the first metatarsal cutter guide at a first arm angle towards the cuneiform attachment feature;

a proximal arm groove toward a distal end of the proximal arm;

a proximal arm retainer configured to engage with a body of the cuneiform attachment feature and engage with the proximal arm groove to couple the proximal arm to the cuneiform attachment feature;

a distal arm that extends from a second side of the first metatarsal cutter guide at a second arm angle towards the first metatarsal attachment feature;

a distal arm groove toward a distal end of the distal arm;

a distal arm retainer configured to engage with a body of the first metatarsal attachment feature and engage with the distal arm groove to couple the distal arm to the first metatarsal attachment feature; and wherein at least one of a length of the proximal arm, a length of the distal arm, a size of the first arm angle and a size of the second arm angle are defined such that operation of the cutting tool by way of the first metatarsal cutter guide forms an osteotomy of a predefined trajectory in the first metatarsal of the patient.

20. The osteotomy system of claim 17, wherein the cuneiform attachment feature and the first metatarsal attachment feature each couple to one of the cuneiform cutter guide and the first metatarsal cutter guide by a pair of toolless couplers.

* * * * *